United States Patent
Coronella et al.

(10) Patent No.: US 11,299,547 B2
(45) Date of Patent: Apr. 12, 2022

(54) CMET MONOCLONAL BINDING AGENTS, DRUG CONJUGATES THEREOF AND USES THEREOF

(71) Applicant: MITSUBISHI TANABE PHARMA CORPORATION, Osaka (JP)

(72) Inventors: Julia Coronella, San Diego, CA (US); Vincent Blot, San Francisco, CA (US); Marco Gymnopoulos, San Diego, CA (US); Anjuli Timmer, San Diego, CA (US); Ryo Fujita, Osaka (JP); Roland Newman, San Diego, CA (US)

(73) Assignee: MITSUBISHI TANABE PHARMA CORPORATION, Osaka (JP)

(*) Notice: Subject to any disclaimer, the term of this patent is extended or adjusted under 35 U.S.C. 154(b) by 0 days.

(21) Appl. No.: 16/334,326

(22) PCT Filed: Sep. 28, 2017

(86) PCT No.: PCT/JP2017/035259
§ 371 (c)(1),
(2) Date: Mar. 18, 2019

(87) PCT Pub. No.: WO2018/062402
PCT Pub. Date: Apr. 5, 2018

(65) Prior Publication Data
US 2019/0330354 A1   Oct. 31, 2019

Related U.S. Application Data

(60) Provisional application No. 62/401,428, filed on Sep. 29, 2016.

(51) Int. Cl.
*C07K 16/28* (2006.01)
*A61P 35/00* (2006.01)

(52) U.S. Cl.
CPC .......... *C07K 16/2863* (2013.01); *A61P 35/00* (2018.01); *C07K 2317/24* (2013.01); *C07K 2317/33* (2013.01); *C07K 2317/565* (2013.01); *C07K 2317/567* (2013.01); *C07K 2317/73* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| | | |
|---|---|---|
| 2009/0285807 A1 | 11/2009 | Comoglio et al. |
| 2009/0298079 A1 | 12/2009 | Basilico et al. |
| 2013/0089542 A1 | 4/2013 | Lee et al. |
| 2013/0164281 A1 | 6/2013 | Cheong et al. |
| 2013/0216548 A1 | 8/2013 | Neijssen et al. |
| 2014/0294814 A1 | 10/2014 | Lee et al. |
| 2016/0251436 A1 | 9/2016 | Amirina et al. |

FOREIGN PATENT DOCUMENTS

| | | |
|---|---|---|
| AU | 2011203499 A1 | 7/2011 |
| CN | 103003307 A | 3/2013 |
| EP | 2192188 A1 | 6/2010 |
| EP | 2829552 A1 | 1/2015 |
| EP | 2963058 A1 | 1/2016 |
| WO | 2007/090807 A1 | 8/2007 |
| WO | 2014/085821 A2 | 6/2014 |
| WO | 2016/042412 A1 | 3/2016 |
| WO | 2016/106159 A1 | 6/2016 |
| WO | WO 2016/106159  * | 6/2016 |
| WO | 2016/149265 A1 | 9/2016 |

OTHER PUBLICATIONS

Prat et al. (Journal of Cell Science, 1998, 111, 237-247).*
Greenall et al (PLoS ONE, 2012, 7:e34658, internet pp. 1-10).*
European Patent Office, Extended European Search Report for EP Application No. 17856351.6, dated Feb. 26, 2020, pp. 1-11.
Patent Cooperation Treaty, International Preliminary Report on Patentability for PCT/JP2017/035259, dated Dec. 26, 2017, pp. 1-5.
Patent Cooperation Treaty, International Search Report for PCT/JP2017/035259, dated Dec. 26, 2017, pp. 1-4.
China National Intellectual Property Administration, Office Action issued in CN Patent Application No. 201780065437.5, dated Jan. 12, 2022, p. 9.

* cited by examiner

*Primary Examiner* — Laura B Goddard
(74) *Attorney, Agent, or Firm* — Pillsbury Winthrop Shaw Pittman LLP

(57) ABSTRACT

Presented herein, in certain embodiments, are compositions comprising monoclonal binding agents that specifically bind to the extracellular domain of cMET and uses thereof.

20 Claims, 18 Drawing Sheets
Specification includes a Sequence Listing.

FIG. 4

| PLATE 3 | | | |
|---|---|---|---|
| Well name | Description | FACS Geom. Mean | MET BINDING ELISA OD450nm |
| Well_E01.fcs | negative control | 103000 | NA |
| Well_F01.fcs | negative control | 116000 | NA |
| Well_A01.fcs | positive control | 83500 | NA |
| Well_B01.fcs | positive control | 81800 | NA |
| Well_E09.fcs | hybridoma | 61000 | 4.5319 |
| Well_D12.fcs | hybridoma | 67200 | 4.3803 |
| Well_E02.fcs | hybridoma | 69800 | 4.596 |
| Well_F04.fcs | hybridoma | 77300 | 3.0801 |
| Well_B10.fcs | hybridoma | 97200 | 0.0211 |
| Well_H06.fcs | hybridoma | 97600 | 6.1209 |
| Well_F06.fcs | hybridoma | 97800 | -0.0005 |
| Well_G10.fcs | hybridoma | 98800 | 0.0078 |
| Well_E07.fcs | hybridoma | 98900 | 0.0011 |
| Well_H10.fcs | hybridoma | 98900 | 1.7238 |
| Well_E06.fcs | hybridoma | 99300 | 5.2925 |
| Well_F10.fcs | hybridoma | 99700 | 0.0185 |
| Well_F07.fcs | hybridoma | 99800 | 0.235 |

FIG. 8A
Light Chain

Sequences of top 9 murine clones. Two clones were duplicated giving 7 unique sequences

LC F6B1P1E2 = F6BP3E2
LC F6B1P3D12 = F6BP3E9

FIG. 8B
Heavy Chain

HUMANIZED LIGHT CHAIN VARIABLE REGIONS

| | SEQ ID NO: | 1 | 50 |
|---|---|---|---|
| p3D12 VL | 45 (1) | QIVLTQSPAIMSASPGEKVTLTCSASSSVTSNYLYWYQQKPGSSPKLWIY |
| p3D12 VL-ven | 46 (1) | QIVLTQSPAIMSASPGERVTLSCSASSSVTSNYLYWYQQKPGSSPRLWIY |
| p3D12 VL-fra | 47 (1) | QIVLTQSPATLSLSPGERATLSCSASSSVTSNYLYWYQQKPGSSPRLLIY |
| p3D12 VL-abb/sdr | 48 (1) | QIVLTQSPATLSLSPGERATLSCRASQSVTSNYLYWYQQKPGSSPRLLIY |
| p3D12 VL-cdr | 49 (1) | QIVLTQSPATLSLSPGERATLSCSASSSVTSNYLYWYQQKPGSSPRLLIY |

| | | 51 | 100 |
|---|---|---|---|
| p3D12 VL | (51) | STSNLASGVPARFSGSGSGTSYSLTISSMEAEDAASYFCHQWSSYPPTFG |
| p3D12 VL-ven | (51) | STSNLASGVPARFSGSGSGTSYSLTISRMEPEDAASYFCHQWSSYPPTFG |
| p3D12 VL-fra | (51) | STSNLASGVPARFSGSGSGTSYTLTISSLEAEDAASYFCHQWSSYPPTFG |
| p3D12 VL-abb/sdr | (51) | STSNLASGVPARFSGSGSGTDYTLTISRLEPEDFASYFCHQWSSYPPTFG |
| p3D12 VL-cdr | (51) | STSNLASGVPARFSGSGSGTSYTLTISRLEPEDFASYFCHQWSSYPPTFG |

| | | 101 | |
|---|---|---|---|
| p3D12 VL | (101) | SGTKLEIKR |
| p3D12 VL-ven | (101) | SGTKLEIKR |
| p3D12 VL-fra | (101) | SGTKLEIKR |
| p3D12 VL-abb/sdr | (101) | SGTKLEIKR |
| p3D12 VL-cdr | (101) | SGTKLEIKR |

FIG. 14

HUMANIZED HEAVY CHAIN VARIABLE REGIONS

| | SEQ ID NO: | 1 | 50 |
|---|---|---|---|
| P3D12 VH | 104 | (1) | QVQLQQSGAELAKPGASVKMSCKASGYTFTSYWMHWVKQRPGQGLDWIGY |
| P3D12 VH-fra | 105 | (1) | QVQLQQSGAEVKKPGASVKVSCKASGYTFTSYWMHWVKQRPGQGLDWIGY |
| P3D12 VH-ven | 106 | (1) | QVQLVQSGAEVKKPGASVKVSCKASGYTFTSYWMHWVKQAPGQGLDWIGY |
| P3D12 VH-abb/sdr | 107 | (1) | QVQLVQSGAEVKKPGASVKVSCKASGYTFTSYWMHWVKQAPGQGLDWMGY |
| P3D12 VH-cdr | 108 | (1) | QVQLVQSGAEVKKPGASVKVSCKASGYTFTSYWMHWVKQAPGQGLDWIGY |

| | | 51 | 100 |
|---|---|---|---|
| P3D12 VH | | (51) | IKPSTDNTEYNQKFKDKATLTADKSSSTAYMQLSSLTSEDSAVYYCARSY |
| P3D12 VH-fra | | (51) | IKPSTDNTEYNQKFKDRVTLTADKSTSTAYMQLSNLISEDTAVYYCARSY |
| P3D12 VH-ven | | (51) | IKPSTDNTEYNQKFKDRATLTADKSTSTAYMQLSSLRSEDTAVYYCARSY |
| P3D12 VH-abb/sdr | | (51) | IKPSTDNTEYAQKFQGRVTLTADKSTSTAYMELSSLRSEDTAVYYCARSY |
| P3D12 VH-cdr | | (51) | IKPSTDNTEYNQKFKDRATLTADKSTSTAYMELSSLRSEDTAVYYCARSY |

| | | 101 | 119 |
|---|---|---|---|
| P3D12 VH | | (101) | GNYPLMDYWGQGTSVTVSS |
| P3D12 VH-fra | | (101) | GNYPLMDYWGQGTSVTVSS |
| P3D12 VH-ven | | (101) | GNYPLMDYWGQGTTVTVSS |
| P3D12 VH-abb/sdr | | (101) | GNYPLMDYWGQGTTVTVSS |
| P3D12 VH-cdr | | (101) | GNYPLMDYWGQGTTVTVSS |

US 11,299,547 B2

SEQUENCE LISTING

```
<160> NUMBER OF SEQ ID NOS: 113

<210> SEQ ID NO 1
<211> LENGTH: 16
<212> TYPE: PRT
<213> ORGANISM: Mus musculus

<400> SEQUENCE: 1

Arg Ser Ser Gln Thr Ile Val His Gly Thr Gly Asn Thr Tyr Leu Glu
1               5                   10                  15

<210> SEQ ID NO 2
<211> LENGTH: 11
<212> TYPE: PRT
<213> ORGANISM: Mus musculus

<400> SEQUENCE: 2

Gln Thr Ile Val His Gly Thr Gly Asn Thr Tyr
1               5                   10

<210> SEQ ID NO 3
<211> LENGTH: 11
<212> TYPE: PRT
<213> ORGANISM: Mus musculus

<400> SEQUENCE: 3
```

Lys Ala Ser Glu Asn Val Gly Thr Tyr Val Ser
1               5                   10

<210> SEQ ID NO 4
<211> LENGTH: 6
<212> TYPE: PRT
<213> ORGANISM: Mus musculus

<400> SEQUENCE: 4

Glu Asn Val Gly Thr Tyr
1               5

<210> SEQ ID NO 5
<211> LENGTH: 17
<212> TYPE: PRT
<213> ORGANISM: Mus musculus

<400> SEQUENCE: 5

Arg Ser Ser Gln Ser Leu Leu Tyr Ser Ile Asn Gln Lys Asn Tyr Leu
1               5                   10                  15

Ala

<210> SEQ ID NO 6
<211> LENGTH: 12
<212> TYPE: PRT
<213> ORGANISM: Mus musculus

<400> SEQUENCE: 6

Gln Ser Leu Leu Tyr Ser Ile Asn Gln Lys Asn Tyr
1               5                   10

<210> SEQ ID NO 7
<211> LENGTH: 11
<212> TYPE: PRT
<213> ORGANISM: Mus musculus

<400> SEQUENCE: 7

Arg Ala Ser Glu Asn Ile Tyr Asn Thr Leu Ala
1               5                   10

<210> SEQ ID NO 8
<211> LENGTH: 6
<212> TYPE: PRT
<213> ORGANISM: Mus musculus

<400> SEQUENCE: 8

Glu Asn Ile Tyr Asn Thr
1               5

<210> SEQ ID NO 9
<211> LENGTH: 12
<212> TYPE: PRT
<213> ORGANISM: Mus musculus

<400> SEQUENCE: 9

Ser Ala Ser Ser Ser Val Thr Ser Asn Tyr Leu Tyr
1               5                   10

<210> SEQ ID NO 10
<211> LENGTH: 7
<212> TYPE: PRT
<213> ORGANISM: Mus musculus

<400> SEQUENCE: 10

```
Ser Ser Val Thr Ser Asn Tyr
1               5

<210> SEQ ID NO 11
<211> LENGTH: 12
<212> TYPE: PRT
<213> ORGANISM: Mus musculus

<400> SEQUENCE: 11

Ser Ala Ser Ser Ser Val Ser Ser Asn Tyr Leu Tyr
1               5                   10

<210> SEQ ID NO 12
<211> LENGTH: 7
<212> TYPE: PRT
<213> ORGANISM: Mus musculus

<400> SEQUENCE: 12

Ser Ser Val Ser Ser Asn Tyr
1               5

<210> SEQ ID NO 13
<211> LENGTH: 12
<212> TYPE: PRT
<213> ORGANISM: Mus musculus
<220> FEATURE:
<221> NAME/KEY: MOD_RES
<222> LOCATION: (7)..(7)
<223> OTHER INFORMATION: S or T

<400> SEQUENCE: 13

Ser Ala Ser Ser Ser Val Xaa Ser Asn Tyr Leu Tyr
1               5                   10

<210> SEQ ID NO 14
<211> LENGTH: 7
<212> TYPE: PRT
<213> ORGANISM: Mus musculus

<400> SEQUENCE: 14

Gln Ser Val Thr Ser Asn Tyr
1               5

<210> SEQ ID NO 15
<211> LENGTH: 12
<212> TYPE: PRT
<213> ORGANISM: Mus musculus

<400> SEQUENCE: 15

Arg Ala Ser Gln Ser Val Thr Ser Asn Tyr Leu Tyr
1               5                   10

<210> SEQ ID NO 16
<211> LENGTH: 7
<212> TYPE: PRT
<213> ORGANISM: Mus musculus

<400> SEQUENCE: 16

Lys Val Ser Asn Arg Phe Ser
1               5

<210> SEQ ID NO 17
<211> LENGTH: 3
<212> TYPE: PRT
<213> ORGANISM: Mus musculus
```

```
<400> SEQUENCE: 17

Lys Val Ser
1

<210> SEQ ID NO 18
<211> LENGTH: 7
<212> TYPE: PRT
<213> ORGANISM: Mus musculus

<400> SEQUENCE: 18

Gly Ala Ser Asn Arg Tyr Thr
1               5

<210> SEQ ID NO 19
<211> LENGTH: 3
<212> TYPE: PRT
<213> ORGANISM: Mus musculus

<400> SEQUENCE: 19

Gly Ala Ser
1

<210> SEQ ID NO 20
<211> LENGTH: 7
<212> TYPE: PRT
<213> ORGANISM: Mus musculus

<400> SEQUENCE: 20

Trp Ala Ser Thr Arg Glu Ser
1               5

<210> SEQ ID NO 21
<211> LENGTH: 3
<212> TYPE: PRT
<213> ORGANISM: Mus musculus

<400> SEQUENCE: 21

Trp Ala Ser
1

<210> SEQ ID NO 22
<211> LENGTH: 7
<212> TYPE: PRT
<213> ORGANISM: Mus musculus

<400> SEQUENCE: 22

Ala Ala Thr Asn Leu Ala Asp
1               5

<210> SEQ ID NO 23
<211> LENGTH: 3
<212> TYPE: PRT
<213> ORGANISM: Mus musculus

<400> SEQUENCE: 23

Ala Ala Thr
1

<210> SEQ ID NO 24
<211> LENGTH: 7
<212> TYPE: PRT
<213> ORGANISM: Mus musculus

<400> SEQUENCE: 24
```

Ser Thr Ser Asn Leu Ala Ser
1               5

<210> SEQ ID NO 25
<211> LENGTH: 3
<212> TYPE: PRT
<213> ORGANISM: Mus musculus

<400> SEQUENCE: 25

Ser Thr Ser
1

<210> SEQ ID NO 26
<211> LENGTH: 20
<212> TYPE: PRT
<213> ORGANISM: Mus musculus

<400> SEQUENCE: 26

Phe Gln Gly Ser His Val Pro Tyr Thr Phe Gly Gly Gly Thr Lys Leu
1               5                   10                  15

Glu Ile Lys Arg
            20

<210> SEQ ID NO 27
<211> LENGTH: 9
<212> TYPE: PRT
<213> ORGANISM: Mus musculus

<400> SEQUENCE: 27

Phe Gln Gly Ser His Val Pro Tyr Thr
1               5

<210> SEQ ID NO 28
<211> LENGTH: 20
<212> TYPE: PRT
<213> ORGANISM: Mus musculus

<400> SEQUENCE: 28

Gly Gln Ser Tyr Ser Tyr Pro Leu Thr Phe Gly Ala Gly Thr Lys Leu
1               5                   10                  15

Glu Leu Lys Arg
            20

<210> SEQ ID NO 29
<211> LENGTH: 9
<212> TYPE: PRT
<213> ORGANISM: Mus musculus

<400> SEQUENCE: 29

Gly Gln Ser Tyr Ser Tyr Pro Leu Thr
1               5

<210> SEQ ID NO 30
<211> LENGTH: 19
<212> TYPE: PRT
<213> ORGANISM: Mus musculus

<400> SEQUENCE: 30

Gln Gln Tyr Tyr Thr Tyr Pro Leu Thr Phe Gly Ala Gly Thr Lys Leu
1               5                   10                  15

Glu Leu Lys

<210> SEQ ID NO 31

```
<211> LENGTH: 9
<212> TYPE: PRT
<213> ORGANISM: Mus musculus

<400> SEQUENCE: 31

Gln Gln Tyr Tyr Thr Tyr Pro Leu Thr
1               5

<210> SEQ ID NO 32
<211> LENGTH: 19
<212> TYPE: PRT
<213> ORGANISM: Mus musculus

<400> SEQUENCE: 32

Gln His Phe Trp Gly Thr Pro Tyr Thr Phe Gly Gly Gly Thr Lys Leu
1               5                   10                  15

Glu Ile Lys

<210> SEQ ID NO 33
<211> LENGTH: 9
<212> TYPE: PRT
<213> ORGANISM: Mus musculus

<400> SEQUENCE: 33

Gln His Phe Trp Gly Thr Pro Tyr Thr
1               5

<210> SEQ ID NO 34
<211> LENGTH: 19
<212> TYPE: PRT
<213> ORGANISM: Mus musculus

<400> SEQUENCE: 34

His Gln Trp Ser Ser Tyr Pro Pro Thr Phe Gly Ser Gly Thr Lys Leu
1               5                   10                  15

Glu Ile Lys

<210> SEQ ID NO 35
<211> LENGTH: 9
<212> TYPE: PRT
<213> ORGANISM: Mus musculus

<400> SEQUENCE: 35

His Gln Trp Ser Ser Tyr Pro Pro Thr
1               5

<210> SEQ ID NO 36
<211> LENGTH: 9
<212> TYPE: PRT
<213> ORGANISM: Mus musculus
<220> FEATURE:
<221> NAME/KEY: MOD_RES
<222> LOCATION: (1)..(1)
<223> OTHER INFORMATION: H, Q or G
<220> FEATURE:
<221> NAME/KEY: MOD_RES
<222> LOCATION: (3)..(3)
<223> OTHER INFORMATION: W, S or Y
<220> FEATURE:
<221> NAME/KEY: MOD_RES
<222> LOCATION: (4)..(4)
<223> OTHER INFORMATION: S or Y
<220> FEATURE:
<221> NAME/KEY: MOD_RES
<222> LOCATION: (5)..(5)
<223> OTHER INFORMATION: S or T
<220> FEATURE:
```

```
<221> NAME/KEY: MOD_RES
<222> LOCATION: (8)..(8)
<223> OTHER INFORMATION: P or L

<400> SEQUENCE: 36

Xaa Gln Xaa Xaa Xaa Tyr Pro Xaa Thr
1               5

<210> SEQ ID NO 37
<211> LENGTH: 113
<212> TYPE: PRT
<213> ORGANISM: Mus musculus

<400> SEQUENCE: 37

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Thr Ile Val His Gly
                20                  25                  30

Thr Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

Arg

<210> SEQ ID NO 38
<211> LENGTH: 108
<212> TYPE: PRT
<213> ORGANISM: Mus musculus

<400> SEQUENCE: 38

Asp Ile Val Met Thr Gln Ser Pro Lys Ser Met Ser Met Ser Val Gly
1               5                   10                  15

Glu Arg Val Thr Leu Ser Cys Lys Ala Ser Glu Asn Val Gly Thr Tyr
                20                  25                  30

Val Ser Trp Tyr Gln Gln Lys Pro Asp Gln Ser Pro Lys Leu Leu Ile
            35                  40                  45

Tyr Gly Ala Ser Asn Arg Tyr Thr Gly Val Pro Asp Arg Phe Thr Gly
        50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Ser Tyr Ser Tyr Pro Leu
                85                  90                  95

Thr Phe Gly Ala Gly Thr Lys Leu Glu Leu Lys Arg
            100                 105

<210> SEQ ID NO 39
<211> LENGTH: 114
<212> TYPE: PRT
<213> ORGANISM: Mus musculus

<400> SEQUENCE: 39

Asp Ile Val Met Ser Gln Ser Pro Ser Ser Leu Ala Val Ser Val Gly
1               5                   10                  15
```

Glu Lys Val Thr Met Ser Cys Arg Ser Ser Gln Ser Leu Leu Tyr Ser
            20                  25                  30

Ile Asn Gln Lys Asn Tyr Leu Ala Trp Tyr Gln Gln Ile Pro Gly Gln
                35                  40                  45

Ser Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
65                   70                  75                  80

Ile Ser Arg Val Lys Ala Glu Asp Leu Ala Leu Tyr Tyr Cys Gln Gln
                85                  90                  95

Tyr Tyr Thr Tyr Pro Leu Thr Phe Gly Ala Gly Thr Lys Leu Glu Leu
            100                 105                 110

Lys Arg

<210> SEQ ID NO 40
<211> LENGTH: 110
<212> TYPE: PRT
<213> ORGANISM: Mus musculus

<400> SEQUENCE: 40

Arg Cys Asp Ile Gln Met Thr Gln Ser Pro Ala Ser Leu Ser Val Ser
1               5                   10                  15

Val Gly Glu Thr Val Thr Ile Thr Cys Arg Ala Ser Glu Asn Ile Tyr
            20                  25                  30

Asn Thr Leu Ala Trp Tyr Leu Gln Lys Gln Gly Lys Ser Pro Gln Leu
                35                  40                  45

Leu Val Tyr Ala Ala Thr Asn Leu Ala Asp Gly Val Pro Ser Arg Phe
 50                  55                  60

Ser Gly Ser Gly Ser Gly Thr Gln Tyr Ser Leu Lys Ile Asn Ser Leu
65                   70                  75                  80

Gln Ser Glu Asp Phe Gly Ser Tyr Tyr Cys Gln His Phe Trp Gly Thr
                85                  90                  95

Pro Tyr Thr Phe Gly Gly Gly Thr Lys Leu Glu Ile Lys Arg
            100                 105                 110

<210> SEQ ID NO 41
<211> LENGTH: 109
<212> TYPE: PRT
<213> ORGANISM: Mus musculus

<400> SEQUENCE: 41

Gln Ile Val Leu Thr Gln Ser Pro Ala Ile Met Ser Ala Ser Pro Gly
1               5                   10                  15

Glu Lys Val Thr Leu Thr Cys Ser Ala Ser Ser Ser Val Thr Ser Asn
            20                  25                  30

Tyr Leu Tyr Trp Tyr Gln Gln Lys Pro Gly Ser Ser Pro Lys Leu Trp
                35                  40                  45

Ile Tyr Ser Thr Ser Asn Leu Ala Ser Gly Val Pro Ala Arg Phe Ser
 50                  55                  60

Gly Ser Gly Ser Gly Thr Ser Tyr Ser Leu Thr Ile Ser Ser Met Glu
65                   70                  75                  80

Ala Glu Asp Ala Ala Ser Tyr Phe Cys His Gln Trp Ser Ser Tyr Pro
                85                  90                  95

Pro Thr Phe Gly Ser Gly Thr Lys Leu Glu Ile Lys Arg
            100                 105

<210> SEQ ID NO 42
<211> LENGTH: 109
<212> TYPE: PRT
<213> ORGANISM: Mus musculus

<400> SEQUENCE: 42

Gln Ile Val Leu Thr Gln Ser Pro Ala Ile Met Ser Ala Ser Pro Gly
1               5                   10                  15

Glu Lys Val Thr Leu Thr Cys Ser Ala Ser Ser Val Ser Ser Asn
            20                  25                  30

Tyr Leu Tyr Trp Tyr Gln Gln Lys Pro Gly Ser Ser Pro Lys Leu Trp
            35                  40                  45

Ile Tyr Ser Thr Ser Asn Leu Ala Ser Gly Val Pro Val Arg Phe Ser
        50                  55                  60

Gly Ser Gly Ser Gly Thr Ser Tyr Ser Leu Thr Ile Ser Ser Met Glu
65                  70                  75                  80

Ala Glu Asp Ala Ala Ser Tyr Phe Cys His Gln Trp Ser Ser Tyr Pro
                85                  90                  95

Pro Thr Phe Gly Ser Gly Thr Lys Leu Glu Ile Lys Arg
            100                 105

<210> SEQ ID NO 43
<211> LENGTH: 109
<212> TYPE: PRT
<213> ORGANISM: Mus musculus

<400> SEQUENCE: 43

Gln Ile Val Leu Thr Gln Ser Pro Ala Ile Met Ser Ala Ser Pro Gly
1               5                   10                  15

Glu Lys Val Thr Leu Thr Cys Ser Ala Ser Ser Val Ser Ser Asn
            20                  25                  30

Tyr Leu Tyr Trp Tyr His Gln Lys Pro Gly Ser Ser Pro Lys Leu Trp
            35                  40                  45

Ile Tyr Ser Thr Ser Asn Leu Ala Ser Gly Val Pro Val Arg Phe Ser
        50                  55                  60

Gly Ser Gly Ser Gly Thr Ser Tyr Ser Leu Thr Ile Ser Ser Met Glu
65                  70                  75                  80

Ala Glu Asp Ala Ala Ser Tyr Phe Cys His Gln Trp Ser Ser Tyr Pro
                85                  90                  95

Pro Thr Phe Gly Ser Gly Thr Lys Leu Glu Ile Lys Arg
            100                 105

<210> SEQ ID NO 44
<211> LENGTH: 108
<212> TYPE: PRT
<213> ORGANISM: Mus musculus
<220> FEATURE:
<221> NAME/KEY: MOD_RES
<222> LOCATION: (38)..(38)
<223> OTHER INFORMATION: H or Q
<220> FEATURE:
<221> NAME/KEY: MOD_RES
<222> LOCATION: (61)..(61)
<223> OTHER INFORMATION: A or R

<400> SEQUENCE: 44

Gln Ile Val Leu Thr Gln Ser Pro Ala Ile Met Ser Ala Ser Pro Gly
1               5                   10                  15

Glu Lys Val Thr Leu Thr Cys Ser Ala Ser Ser Val Ser Ser Asn
            20                  25                  30

```
Tyr Leu Tyr Trp Tyr Xaa Gln Lys Pro Gly Ser Ser Pro Lys Leu Trp
        35                  40                  45

Ile Tyr Ser Thr Ser Asn Leu Ala Ser Gly Val Pro Xaa Phe Ser Gly
 50                  55                  60

Ser Gly Ser Gly Thr Ser Tyr Ser Leu Thr Ile Ser Ser Met Glu Ala
 65                  70                  75                  80

Glu Asp Ala Ala Ser Tyr Phe Cys His Gln Trp Ser Ser Tyr Pro Pro
                 85                  90                  95

Thr Phe Gly Ser Gly Thr Lys Leu Glu Ile Lys Arg
            100                 105

<210> SEQ ID NO 45
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Humanized Light Chain

<400> SEQUENCE: 45

Gln Ile Val Leu Thr Gln Ser Pro Ala Ile Met Ser Ala Ser Pro Gly
 1               5                  10                  15

Glu Lys Val Thr Leu Thr Cys Ser Ala Ser Ser Ser Val Thr Ser Asn
                 20                  25                  30

Tyr Leu Tyr Trp Tyr Gln Gln Lys Pro Gly Ser Ser Pro Lys Leu Trp
            35                  40                  45

Ile Tyr Ser Thr Ser Asn Leu Ala Ser Gly Val Pro Ala Arg Phe Ser
 50                  55                  60

Gly Ser Gly Ser Gly Thr Ser Tyr Ser Leu Thr Ile Ser Ser Met Glu
 65                  70                  75                  80

Ala Glu Asp Ala Ala Ser Tyr Phe Cys His Gln Trp Ser Ser Tyr Pro
                 85                  90                  95

Pro Thr Phe Gly Ser Gly Thr Lys Leu Glu Ile Lys Arg
            100                 105

<210> SEQ ID NO 46
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Humanized Light Chain

<400> SEQUENCE: 46

Gln Ile Val Leu Thr Gln Ser Pro Ala Thr Met Ser Ala Ser Pro Gly
 1               5                  10                  15

Glu Arg Val Thr Leu Ser Cys Ser Ala Ser Ser Ser Val Thr Ser Asn
                 20                  25                  30

Tyr Leu Tyr Trp Tyr Gln Gln Lys Pro Gly Ser Ser Pro Arg Leu Trp
            35                  40                  45

Ile Tyr Ser Thr Ser Asn Leu Ala Ser Gly Val Pro Ala Arg Phe Ser
 50                  55                  60

Gly Ser Gly Ser Gly Thr Ser Tyr Thr Leu Thr Ile Ser Arg Met Glu
 65                  70                  75                  80

Pro Glu Asp Ala Ala Ser Tyr Phe Cys His Gln Trp Ser Ser Tyr Pro
```

Pro Thr Phe Gly Ser Gly Thr Lys Leu Glu Ile Lys Arg
            100                 105

<210> SEQ ID NO 47
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Humanized Light Chain

<400> SEQUENCE: 47

Gln Ile Val Leu Thr Gln Ser Pro Ala Ile Leu Ser Leu Ser Pro Gly
1               5                   10                  15

Glu Arg Ala Thr Leu Ser Cys Ser Ala Ser Ser Ser Val Thr Ser Asn
            20                  25                  30

Tyr Leu Tyr Trp Tyr Gln Gln Lys Pro Gly Ser Ser Pro Lys Leu Leu
        35                  40                  45

Ile Tyr Ser Thr Ser Asn Leu Ala Ser Gly Val Pro Ala Arg Phe Ser
50                  55                  60

Gly Ser Gly Ser Gly Thr Ser Tyr Thr Leu Thr Ile Ser Ser Leu Glu
65                  70                  75                  80

Ala Glu Asp Ala Ala Ser Tyr Phe Cys His Gln Trp Ser Ser Tyr Pro
                85                  90                  95

Pro Thr Phe Gly Ser Gly Thr Lys Leu Glu Ile Lys Arg
            100                 105

<210> SEQ ID NO 48
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Humanized Light Chain

<400> SEQUENCE: 48

Gln Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Thr Ser Asn
            20                  25                  30

Tyr Leu Tyr Trp Tyr Gln Gln Lys Pro Gly Ser Ser Pro Arg Leu Leu
        35                  40                  45

Ile Tyr Ser Thr Ser Asn Leu Ala Ser Gly Val Pro Ala Arg Phe Ser
50                  55                  60

Gly Ser Gly Ser Gly Thr Asp Tyr Thr Leu Thr Ile Ser Arg Leu Glu
65                  70                  75                  80

Pro Glu Asp Phe Ala Ser Tyr Phe Cys His Gln Trp Ser Ser Tyr Pro
                85                  90                  95

Pro Thr Phe Gly Ser Gly Thr Lys Leu Glu Ile Lys Arg
            100                 105

<210> SEQ ID NO 49
<211> LENGTH: 109
<212> TYPE: PRT
<213> ORGANISM: Artificial Sequence
<220> FEATURE:

<223> OTHER INFORMATION: Description of Artificial Sequence: Synthetic
      polypeptide
<220> FEATURE:
<223> OTHER INFORMATION: Humanized Light Chain

<400> SEQUENCE: 49

Gln Ile Val Leu Thr Gln Ser Pro Ala Thr Leu Ser Leu Ser Pro Gly
1               5                   10                  15

Glu Arg Ala Thr Leu Ser Cys Ser Ala Ser Ser Val Thr Ser Asn
            20                  25                  30

Tyr Leu Tyr Trp Tyr Gln Gln Lys Pro Gly Ser Ser Pro Arg Leu Leu
        35                  40                  45

Ile Tyr Ser Thr Ser Asn Leu Ala Ser Gly Val Pro Ala Arg Phe Ser
50                  55                  60

Gly Ser Gly Ser Gly Thr Ser Tyr Thr Leu Thr Ile Ser Arg Leu Glu
65                  70                  75                  80

Pro Glu Asp Phe Ala Ser Tyr Phe Cys His Gln Trp Ser Ser Tyr Pro
                85                  90                  95

Pro Thr Phe Gly Ser Gly Thr Lys Leu Glu Ile Lys Arg
            100                 105

<210> SEQ ID NO 50
<211> LENGTH: 10
<212> TYPE: PRT
<213> ORGANISM: Mus musculus

<400> SEQUENCE: 50

Gly Phe Ser Leu Thr Asn Tyr Gly Val Asn
1               5                   10

<210> SEQ ID NO 51
<211> LENGTH: 8
<212> TYPE: PRT
<213> ORGANISM: Mus musculus

<400> SEQUENCE: 51

Gly Phe Ser Leu Thr Asn Tyr Gly
1               5

<210> SEQ ID NO 52
<211> LENGTH: 10
<212> TYPE: PRT
<213> ORGANISM: Mus musculus

<400> SEQUENCE: 52

Gly Phe Asn Ile Asn Asp Tyr Phe Met His
1               5                   10

<210> SEQ ID NO 53
<211> LENGTH: 7
<212> TYPE: PRT
<213> ORGANISM: Mus musculus

<400> SEQUENCE: 53

Phe Asn Ile Asn Asp Tyr Phe
1               5

<210> SEQ ID NO 54
<211> LENGTH: 10
<212> TYPE: PRT
<213> ORGANISM: Mus musculus

<400> SEQUENCE: 54

```
Gly Phe Thr Phe Thr Asp Tyr Tyr Met Ser
1               5                   10
```

<210> SEQ ID NO 55
<211> LENGTH: 8
<212> TYPE: PRT
<213> ORGANISM: Mus musculus

<400> SEQUENCE: 55

```
Gly Phe Thr Phe Thr Asp Tyr Tyr
1               5
```

<210> SEQ ID NO 56
<211> LENGTH: 10
<212> TYPE: PRT
<213> ORGANISM: Mus musculus

<400> SEQUENCE: 56

```
Gly Tyr Thr Phe Thr Asp Tyr Asn Met Asp
1               5                   10
```

<210> SEQ ID NO 57
<211> LENGTH: 7
<212> TYPE: PRT
<213> ORGANISM: Mus musculus

<400> SEQUENCE: 57

```
Tyr Thr Phe Thr Asp Tyr Asn
1               5
```

<210> SEQ ID NO 58
<211> LENGTH: 10
<212> TYPE: PRT
<213> ORGANISM: Mus musculus

<400> SEQUENCE: 58

```
Gly Tyr Thr Phe Thr Ser Tyr Trp Met His
1               5                   10
```

<210> SEQ ID NO 59
<211> LENGTH: 7
<212> TYPE: PRT
<213> ORGANISM: Mus musculus

<400> SEQUENCE: 59

```
Tyr Thr Phe Thr Ser Tyr Trp
1               5
```

<210> SEQ ID NO 60
<211> LENGTH: 8
<212> TYPE: PRT
<213> ORGANISM: Mus musculus
<220> FEATURE:
<221> NAME/KEY: MOD_RES
<222> LOCATION: (6)..(6)
<223> OTHER INFORMATION: D or S
<220> FEATURE:
<221> NAME/KEY: MOD_RES
<222> LOCATION: (8)..(8)
<223> OTHER INFORMATION: N or W

<400> SEQUENCE: 60

```
Gly Tyr Thr Phe Thr Xaa Tyr Xaa
1               5
```

```
<210> SEQ ID NO 61
<211> LENGTH: 10
<212> TYPE: PRT
<213> ORGANISM: Mus musculus
<220> FEATURE:
<221> NAME/KEY: MOD_RES
<222> LOCATION: (2)..(2)
<223> OTHER INFORMATION: Y or F
<220> FEATURE:
<221> NAME/KEY: MOD_RES
<222> LOCATION: (6)..(6)
<223> OTHER INFORMATION: D or S
<220> FEATURE:
<221> NAME/KEY: MOD_RES
<222> LOCATION: (8)..(8)
<223> OTHER INFORMATION: N, W or Y
<220> FEATURE:
<221> NAME/KEY: MOD_RES
<222> LOCATION: (10)..(10)
<223> OTHER INFORMATION: H or S

<400> SEQUENCE: 61

Gly Xaa Thr Phe Thr Xaa Tyr Xaa Met Xaa
1               5                   10

<210> SEQ ID NO 62
<211> LENGTH: 16
<212> TYPE: PRT
<213> ORGANISM: Mus musculus

<400> SEQUENCE: 62

Leu Ile Trp Gly Gly Gly Asp Thr Asp Tyr Asn Ser Ala Leu Lys Ser
1               5                   10                  15

<210> SEQ ID NO 63
<211> LENGTH: 7
<212> TYPE: PRT
<213> ORGANISM: Mus musculus

<400> SEQUENCE: 63

Ile Trp Gly Gly Gly Asp Thr
1               5

<210> SEQ ID NO 64
<211> LENGTH: 17
<212> TYPE: PRT
<213> ORGANISM: Mus musculus

<400> SEQUENCE: 64

Trp Ile Asp Pro Glu Asn Gly Asn Thr Ile Tyr Asp Pro Lys Phe Gln
1               5                   10                  15
Gly

<210> SEQ ID NO 65
<211> LENGTH: 8
<212> TYPE: PRT
<213> ORGANISM: Mus musculus

<400> SEQUENCE: 65

Ile Asp Pro Glu Asn Gly Asn Thr
1               5

<210> SEQ ID NO 66
<211> LENGTH: 19
<212> TYPE: PRT
<213> ORGANISM: Mus musculus

<400> SEQUENCE: 66
```

Phe Ile Arg Asn Lys Ala Asn Gly Tyr Thr Thr Lys Tyr Ser Ala Ser
1               5                   10                  15

Val Lys Gly

<210> SEQ ID NO 67
<211> LENGTH: 10
<212> TYPE: PRT
<213> ORGANISM: Mus musculus

<400> SEQUENCE: 67

Ile Arg Asn Lys Ala Asn Gly Tyr Thr Thr
1               5                   10

<210> SEQ ID NO 68
<211> LENGTH: 17
<212> TYPE: PRT
<213> ORGANISM: Mus musculus

<400> SEQUENCE: 68

Asp Ile Asn Pro Asn Asn Gly Gly Thr Ile Tyr Asn Gln Lys Phe Lys
1               5                   10                  15

Gly

<210> SEQ ID NO 69
<211> LENGTH: 8
<212> TYPE: PRT
<213> ORGANISM: Mus musculus

<400> SEQUENCE: 69

Ile Asn Pro Asn Asn Gly Gly Thr
1               5

<210> SEQ ID NO 70
<211> LENGTH: 17
<212> TYPE: PRT
<213> ORGANISM: Mus musculus

<400> SEQUENCE: 70

Tyr Ile Lys Pro Ser Thr Asp Asn Thr Glu Tyr Asn Gln Lys Phe Lys
1               5                   10                  15

Asp

<210> SEQ ID NO 71
<211> LENGTH: 8
<212> TYPE: PRT
<213> ORGANISM: Mus musculus

<400> SEQUENCE: 71

Ile Lys Pro Ser Thr Asp Asn Thr
1               5

<210> SEQ ID NO 72
<211> LENGTH: 17
<212> TYPE: PRT
<213> ORGANISM: Mus musculus

<400> SEQUENCE: 72

Tyr Ile Asn Pro Ser Thr Asp Tyr Thr Glu Tyr Asn Gln Lys Phe Lys
1               5                   10                  15

Asp

```
<210> SEQ ID NO 73
<211> LENGTH: 8
<212> TYPE: PRT
<213> ORGANISM: Mus musculus

<400> SEQUENCE: 73

Ile Asn Pro Ser Thr Asp Tyr Thr
1               5

<210> SEQ ID NO 74
<211> LENGTH: 17
<212> TYPE: PRT
<213> ORGANISM: Mus musculus

<400> SEQUENCE: 74

Tyr Ile Asn Pro Ser Thr Asp Tyr Ile Glu Tyr Asn Gln Lys Phe Lys
1               5                   10                  15

Asp

<210> SEQ ID NO 75
<211> LENGTH: 8
<212> TYPE: PRT
<213> ORGANISM: Mus musculus

<400> SEQUENCE: 75

Ile Asn Pro Ser Thr Asp Tyr Ile
1               5

<210> SEQ ID NO 76
<211> LENGTH: 8
<212> TYPE: PRT
<213> ORGANISM: Mus musculus
<220> FEATURE:
<221> NAME/KEY: MOD_RES
<222> LOCATION: (8)..(8)
<223> OTHER INFORMATION: I or T

<400> SEQUENCE: 76

Ile Asn Pro Ser Thr Asp Tyr Xaa
1               5

<210> SEQ ID NO 77
<211> LENGTH: 17
<212> TYPE: PRT
<213> ORGANISM: Mus musculus
<220> FEATURE:
<221> NAME/KEY: MOD_RES
<222> LOCATION: (1)..(1)
<223> OTHER INFORMATION: Y or D
<220> FEATURE:
<221> NAME/KEY: MOD_RES
<222> LOCATION: (3)..(3)
<223> OTHER INFORMATION: K or N
<220> FEATURE:
<221> NAME/KEY: MOD_RES
<222> LOCATION: (8)..(8)
<223> OTHER INFORMATION: N or Y
<220> FEATURE:
<221> NAME/KEY: MOD_RES
<222> LOCATION: (9)..(9)
<223> OTHER INFORMATION: T or I
<220> FEATURE:
<221> NAME/KEY: MOD_RES
<222> LOCATION: (12)..(12)
<223> OTHER INFORMATION: A or N
<220> FEATURE:
<221> NAME/KEY: MOD_RES
<222> LOCATION: (16)..(16)
<223> OTHER INFORMATION: Q or K
<220> FEATURE:
```

```
<221> NAME/KEY: MOD_RES
<222> LOCATION: (17)..(17)
<223> OTHER INFORMATION: G or D

<400> SEQUENCE: 77

Xaa Ile Xaa Pro Ser Thr Asp Xaa Xaa Glu Tyr Xaa Gln Lys Phe Xaa
1               5                   10                  15

Xaa

<210> SEQ ID NO 78
<211> LENGTH: 17
<212> TYPE: PRT
<213> ORGANISM: Mus musculus

<400> SEQUENCE: 78

Tyr Ile Lys Pro Ser Thr Asp Asn Thr Glu Tyr Ala Gln Lys Phe Gln
1               5                   10                  15

Gly

<210> SEQ ID NO 79
<211> LENGTH: 10
<212> TYPE: PRT
<213> ORGANISM: Mus musculus

<400> SEQUENCE: 79

Cys Ala Arg Asp Tyr Tyr Gly Phe Asp Tyr
1               5                   10

<210> SEQ ID NO 80
<211> LENGTH: 7
<212> TYPE: PRT
<213> ORGANISM: Mus musculus

<400> SEQUENCE: 80

Asp Tyr Tyr Gly Phe Asp Tyr
1               5

<210> SEQ ID NO 81
<211> LENGTH: 18
<212> TYPE: PRT
<213> ORGANISM: Mus musculus

<400> SEQUENCE: 81

Cys Ala Arg Gly Gly Asn Tyr Leu Arg Glu Ser Tyr Tyr Tyr Ala Met
1               5                   10                  15

Asp Tyr

<210> SEQ ID NO 82
<211> LENGTH: 16
<212> TYPE: PRT
<213> ORGANISM: Mus musculus

<400> SEQUENCE: 82

Arg Gly Gly Asn Tyr Leu Arg Glu Ser Tyr Tyr Tyr Ala Met Asp Tyr
1               5                   10                  15

<210> SEQ ID NO 83
<211> LENGTH: 10
<212> TYPE: PRT
<213> ORGANISM: Mus musculus

<400> SEQUENCE: 83

Cys Ser Lys Asp Arg Gly Tyr Phe Asp Tyr
```

```
<210> SEQ ID NO 84
<211> LENGTH: 7
<212> TYPE: PRT
<213> ORGANISM: Mus musculus

<400> SEQUENCE: 84

Asp Arg Gly Tyr Phe Asp Tyr
1               5

<210> SEQ ID NO 85
<211> LENGTH: 18
<212> TYPE: PRT
<213> ORGANISM: Mus musculus

<400> SEQUENCE: 85

Arg Ala Arg Gly Asp Tyr Tyr Gly Ser Ser Arg Tyr Tyr Tyr Ala Met
1               5                   10                  15

Asp Tyr

<210> SEQ ID NO 86
<211> LENGTH: 16
<212> TYPE: PRT
<213> ORGANISM: Mus musculus

<400> SEQUENCE: 86

Arg Gly Asp Tyr Tyr Gly Ser Ser Arg Tyr Tyr Tyr Ala Met Asp Tyr
1               5                   10                  15

<210> SEQ ID NO 87
<211> LENGTH: 13
<212> TYPE: PRT
<213> ORGANISM: Mus musculus

<400> SEQUENCE: 87

Cys Ala Arg Ser Tyr Gly Asn Tyr Pro Leu Met Asp Tyr
1               5                   10

<210> SEQ ID NO 88
<211> LENGTH: 10
<212> TYPE: PRT
<213> ORGANISM: Mus musculus

<400> SEQUENCE: 88

Ser Tyr Gly Asn Tyr Pro Leu Met Asp Tyr
1               5                   10

<210> SEQ ID NO 89
<211> LENGTH: 13
<212> TYPE: PRT
<213> ORGANISM: Mus musculus

<400> SEQUENCE: 89

Cys Val Arg Ser Tyr Gly Asn Tyr Pro Leu Met Asp Tyr
1               5                   10

<210> SEQ ID NO 90
<211> LENGTH: 13
<212> TYPE: PRT
<213> ORGANISM: Mus musculus

<400> SEQUENCE: 90

Cys Ala Arg Ser Tyr Gly Asn Phe Pro Leu Met Asp Tyr
```

```
<210> SEQ ID NO 91
<211> LENGTH: 11
<212> TYPE: PRT
<213> ORGANISM: Mus musculus

<400> SEQUENCE: 91

Arg Ser Tyr Gly Asn Phe Pro Leu Met Asp Tyr
1               5                   10

<210> SEQ ID NO 92
<211> LENGTH: 13
<212> TYPE: PRT
<213> ORGANISM: Mus musculus
<220> FEATURE:
<221> NAME/KEY: MOD_RES
<222> LOCATION: (2)..(2)
<223> OTHER INFORMATION: A or V
<220> FEATURE:
<221> NAME/KEY: MOD_RES
<222> LOCATION: (8)..(8)
<223> OTHER INFORMATION: F or Y

<400> SEQUENCE: 92

Cys Xaa Arg Ser Tyr Gly Asn Xaa Pro Leu Met Asp Tyr
1               5                   10

<210> SEQ ID NO 93
<211> LENGTH: 11
<212> TYPE: PRT
<213> ORGANISM: Mus musculus
<220> FEATURE:
<221> NAME/KEY: MOD_RES
<222> LOCATION: (6)..(6)
<223> OTHER INFORMATION: F or Y

<400> SEQUENCE: 93

Arg Ser Tyr Gly Asn Xaa Pro Leu Met Asp Tyr
1               5                   10

<210> SEQ ID NO 94
<211> LENGTH: 117
<212> TYPE: PRT
<213> ORGANISM: Mus musculus

<400> SEQUENCE: 94

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Asn Tyr
                20                  25                  30

Gly Val Asn Trp Val Arg Gln Pro Pro Gly Lys Gly Leu Glu Trp Leu
            35                  40                  45

Gly Leu Ile Trp Gly Gly Gly Asp Thr Asp Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Glu Thr Asn Ser Leu Gln Thr Asp Asp Thr Ala Arg Tyr Tyr
                85                  90                  95

Cys Ala Arg Asp Tyr Tyr Gly Phe Asp Tyr Trp Gly Gln Gly Thr Thr
            100                 105                 110

Leu Thr Val Ser Ser
        115
```

<210> SEQ ID NO 95
<211> LENGTH: 118
<212> TYPE: PRT
<213> ORGANISM: Mus musculus

<400> SEQUENCE: 95

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Ala Leu Glu Trp Leu
        35                  40                  45

Gly Phe Ile Arg Asn Lys Ala Asn Gly Tyr Thr Thr Lys Tyr Ser Ala
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Ala Glu Asp Ser Ala Thr Tyr
                85                  90                  95

Tyr Cys Ser Lys Asp Arg Gly Tyr Phe Asp Tyr Trp Gly Gln Gly Thr
            100                 105                 110

Thr Leu Thr Val Ser Ser
        115

<210> SEQ ID NO 96
<211> LENGTH: 127
<212> TYPE: PRT
<213> ORGANISM: Mus musculus

<400> SEQUENCE: 96

Val Asn Ser Glu Val Gln Leu Gln Gln Ser Gly Ala Glu Leu Val Arg
1               5                   10                  15

Pro Gly Ala Leu Val Lys Leu Ser Cys Lys Ala Ser Gly Phe Asn Ile
            20                  25                  30

Asn Asp Tyr Phe Met His Trp Val Lys Gln Arg Pro Glu Gln Gly Leu
        35                  40                  45

Glu Trp Ile Gly Trp Ile Asp Pro Glu Asn Gly Asn Thr Ile Tyr Asp
    50                  55                  60

Pro Lys Phe Gln Gly Lys Ala Ser Ile Thr Ala Asp Thr Ser Ser Asn
65                  70                  75                  80

Thr Ala Tyr Leu Gln Leu Ser Ser Leu Thr Ser Glu Asp Thr Ala Val
                85                  90                  95

Tyr Tyr Cys Ala Arg Gly Gly Asn Tyr Leu Arg Glu Ser Tyr Tyr Tyr
            100                 105                 110

Ala Met Asp Tyr Trp Gly Gln Gly Thr Ser Val Thr Val Ser Ser
        115                 120                 125

<210> SEQ ID NO 97
<211> LENGTH: 127
<212> TYPE: PRT
<213> ORGANISM: Mus musculus

<400> SEQUENCE: 97

Val Leu Ser Glu Val Leu Leu Gln Gln Ser Gly Pro Glu Leu Val Lys
1               5                   10                  15

Pro Gly Ala Ser Val Lys Ile Pro Cys Lys Ala Ser Gly Tyr Thr Phe
            20                  25                  30

Thr Asp Tyr Asn Met Asp Trp Val Lys Gln Ser His Gly Lys Ser Leu

```
                35                  40                  45
Glu Trp Ile Gly Asp Ile Asn Pro Asn Asn Gly Thr Ile Tyr Asn
 50                  55                  60

Gln Lys Phe Lys Gly Lys Ala Thr Leu Thr Val Asp Lys Ser Ser Ser
 65                  70                  75                  80

Thr Ala Tyr Met Glu Leu Arg Ser Leu Thr Ser Glu Asp Thr Ala Val
                 85                  90                  95

Tyr Tyr Arg Ala Arg Gly Asp Tyr Tyr Gly Ser Ser Tyr Tyr Tyr
                100                 105                 110

Ala Met Asp Tyr Trp Gly Gln Gly Thr Ser Val Thr Val Ser Ser
                115                 120                 125

<210> SEQ ID NO 98
<211> LENGTH: 119
<212> TYPE: PRT
<213> ORGANISM: Mus musculus

<400> SEQUENCE: 98

Gln Val Gln Leu Gln Gln Ser Gly Ala Glu Leu Ala Lys Pro Gly Ala
 1               5                  10                  15

Ser Val Lys Met Ser Cys Arg Ala Ser Gly Tyr Thr Phe Thr Ser Tyr
                 20                  25                  30

Trp Met His Trp Val Lys Gln Arg Pro Gly Gln Gly Leu Asp Trp Ile
                 35                  40                  45

Gly Tyr Ile Lys Pro Ser Thr Asp Asn Thr Glu Tyr Asn Gln Lys Phe
 50                  55                  60

Lys Asp Lys Ala Thr Leu Thr Ala Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Ser Tyr Gly Asn Tyr Pro Leu Met Asp Tyr Trp Gly Gln Gly
                100                 105                 110

Thr Ser Val Thr Val Ser Ser
                115

<210> SEQ ID NO 99
<211> LENGTH: 119
<212> TYPE: PRT
<213> ORGANISM: Mus musculus

<400> SEQUENCE: 99

Gln Val Gln Leu Gln Gln Ser Gly Ala Glu Leu Ala Lys Pro Gly Ala
 1               5                  10                  15

Ser Val Lys Met Ser Cys Arg Ala Ser Gly Tyr Thr Phe Thr Ser Tyr
                 20                  25                  30

Trp Met His Trp Val Lys Gln Arg Pro Gly Gln Gly Leu Asp Trp Ile
                 35                  40                  45

Gly Tyr Ile Lys Pro Ser Thr Asp Asn Thr Glu Tyr Asn Gln Lys Phe
 50                  55                  60

Lys Asp Lys Ala Thr Leu Thr Ala Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Ser Tyr Gly Asn Tyr Pro Leu Met Asp Tyr Trp Gly Gln Gly
                100                 105                 110

Thr Ser Val Thr Val Ser Ser
```

-continued

115

<210> SEQ ID NO 100
<211> LENGTH: 119
<212> TYPE: PRT
<213> ORGANISM: Mus musculus

<400> SEQUENCE: 100

Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Tyr Ile Asn Pro Ser Thr Asp Tyr Thr Glu Tyr Asn Gln Lys Phe
    50                  55                  60

Lys Asp Lys Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Tyr Cys
                85                  90                  95

Val Arg Ser Tyr Gly Asn Tyr Pro Leu Met Asp Tyr Trp Gly Gln Gly
            100                 105                 110

Thr Ser Val Thr Val Ser Ser
        115

<210> SEQ ID NO 101
<211> LENGTH: 119
<212> TYPE: PRT
<213> ORGANISM: Mus musculus

<400> SEQUENCE: 101

Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Tyr Ile Asn Pro Ser Thr Asp Tyr Thr Glu Tyr Asn Gln Lys Phe
    50                  55                  60

Lys Asp Lys Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Tyr Cys
                85                  90                  95

Val Arg Ser Tyr Gly Asn Tyr Pro Leu Met Asp Tyr Trp Gly Gln Gly
            100                 105                 110

Thr Ser Val Thr Val Ser Ser
        115

<210> SEQ ID NO 102
<211> LENGTH: 119
<212> TYPE: PRT
<213> ORGANISM: Mus musculus

<400> SEQUENCE: 102

Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Tyr Ile Asn Pro Ser Thr Asp Tyr Ile Glu Tyr Asn Gln Lys Phe
    50                  55                  60

Lys Asp Lys Ala Thr Leu Thr Ala Gly Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Tyr Gly Asn Phe Pro Leu Met Asp Tyr Trp Gly Gln Gly
                100                 105                 110

Thr Ser Val Thr Val Ser Ser
        115

<210> SEQ ID NO 103
<211> LENGTH: 119
<212> TYPE: PRT
<213> ORGANISM: Mus musculus
<220> FEATURE:
<221> NAME/KEY: MOD_RES
<222> LOCATION: (23)..(23)
<223> OTHER INFORMATION: K or R
<220> FEATURE:
<221> NAME/KEY: MOD_RES
<222> LOCATION: (46)..(46)
<223> OTHER INFORMATION: E or D
<220> FEATURE:
<221> NAME/KEY: MOD_RES
<222> LOCATION: (52)..(52)
<223> OTHER INFORMATION: K or N
<220> FEATURE:
<221> NAME/KEY: MOD_RES
<222> LOCATION: (57)..(57)
<223> OTHER INFORMATION: Y or N
<220> FEATURE:
<221> NAME/KEY: MOD_RES
<222> LOCATION: (58)..(58)
<223> OTHER INFORMATION: T or I
<220> FEATURE:
<221> NAME/KEY: MOD_RES
<222> LOCATION: (77)..(77)
<223> OTHER INFORMATION: S or T
<220> FEATURE:
<221> NAME/KEY: MOD_RES
<222> LOCATION: (97)..(97)
<223> OTHER INFORMATION: A or V
<220> FEATURE:
<221> NAME/KEY: MOD_RES
<222> LOCATION: (103)..(103)
<223> OTHER INFORMATION: Y or F

<400> SEQUENCE: 103

Gln Val Gln Leu Gln Gln Ser Gly Ala Glu Leu Ala Lys Pro Gly Ala
1               5                   10                  15

Ser Val Lys Met Ser Cys Xaa Ala Ser Gly Tyr Thr Phe Thr Ser Tyr
            20                  25                  30

Trp Met His Trp Val Lys Gln Arg Pro Gly Gln Gly Leu Xaa Trp Ile
        35                  40                  45

Gly Tyr Ile Xaa Pro Ser Thr Asp Xaa Xaa Glu Tyr Asn Gln Lys Phe
    50                  55                  60

Lys Asp Lys Ala Thr Leu Thr Ala Asp Lys Ser Ser Xaa Thr Ala Tyr
65                  70                  75                  80

Met Gln Leu Ser Ser Leu Thr Ser Glu Asp Ser Ala Val Tyr Tyr Cys
                85                  90                  95

Xaa Arg Ser Tyr Gly Asn Xaa Pro Leu Met Asp Tyr Trp Gly Gln Gly
                100                 105                 110

Thr Ser Val Thr Val Ser Ser
        115

<210> SEQ ID NO 104
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Humanized Heavy Chain

<400> SEQUENCE: 104

Gln Val Gln Leu Gln Gln Ser Gly Ala Glu Leu Ala Lys Pro Gly Ala
1               5                   10                  15

Ser Val Lys Met Ser Cys Arg Ala Ser Gly Tyr Thr Phe Thr Ser Tyr
            20                  25                  30

Trp Met His Trp Val Lys Gln Arg Pro Gly Gln Gly Leu Asp Trp Ile
        35                  40                  45

Gly Tyr Ile Lys Pro Ser Thr Asp Asn Thr Glu Tyr Asn Gln Lys Phe
    50                  55                  60

Lys Asp Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Tyr Gly Asn Tyr Pro Leu Met Asp Tyr Trp Gly Gln Gly
            100                 105                 110

Thr Ser Val Thr Val Ser Ser
        115

<210> SEQ ID NO 105
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Humanized Heavy Chain

<400> SEQUENCE: 105

Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Lys Gln Arg Pro Gly Gln Gly Leu Asp Trp Ile
        35                  40                  45

Gly Tyr Ile Lys Pro Ser Thr Asp Asn Thr Glu Tyr Asn Gln Lys Phe
    50                  55                  60

Lys Asp Arg Val Thr Leu Thr Ala Asp Lys Ser Thr Ser Thr Ala Tyr
65                  70                  75                  80

Met Gln Leu Ser Asn Leu Ile Ser Glu Asp Thr Ala Val Tyr Tyr Cys
                85                  90                  95

Ala Arg Ser Tyr Gly Asn Tyr Pro Leu Met Asp Tyr Trp Gly Gln Gly
            100                 105                 110

Thr Ser Val Thr Val Ser Ser
        115

-continued

```
<210> SEQ ID NO 106
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Humanized Heavy Chain

<400> SEQUENCE: 106

Gln Val Gln Leu Val Gln Ser Gly Ala Glu Val Ala Lys Pro Gly Ala
1               5                   10                  15

Ser Val Lys Met Ser Cys Lys Ala Ser Gly Tyr Thr Phe Thr Ser Tyr
            20                  25                  30

Trp Met His Trp Val Lys Gln Ala Pro Gly Gln Gly Leu Asp Trp Ile
        35                  40                  45

Gly Tyr Ile Lys Pro Ser Thr Asp Asn Thr Glu Tyr Asn Gln Lys Phe
    50                  55                  60

Lys Asp Lys Ala Thr Leu Thr Ala Asp Lys Ser Thr Ser Thr Ala Tyr
65                  70                  75                  80

Met Gln Leu Ser Ser Leu Arg Ser Glu Asp Thr Ala Val Tyr Tyr Cys
                85                  90                  95

Ala Arg Ser Tyr Gly Asn Tyr Pro Leu Met Asp Tyr Trp Gly Gln Gly
            100                 105                 110

Thr Thr Val Thr Val Ser Ser
        115

<210> SEQ ID NO 107
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Humanized Heavy Chain

<400> SEQUENCE: 107

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Lys Gln Ala Pro Gly Gln Gly Leu Asp Trp Met
        35                  40                  45

Gly Tyr Ile Lys Pro Ser Thr Asp Asn Thr Glu Tyr Ala Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Tyr Gly Asn Tyr Pro Leu Met Asp Tyr Trp Gly Gln Gly
            100                 105                 110

Thr Thr Val Thr Val Ser Ser
        115

<210> SEQ ID NO 108
<211> LENGTH: 119
<212> TYPE: PRT
<213> ORGANISM: Artificial Sequence
<220> FEATURE:
```

<223> OTHER INFORMATION: Description of Artificial Sequence: Synthetic
polypeptide
<220> FEATURE:
<223> OTHER INFORMATION: Humanized Heavy Chain

<400> SEQUENCE: 108

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Lys Gln Ala Pro Gly Gln Gly Leu Asp Trp Ile
        35                  40                  45

Gly Tyr Ile Lys Pro Ser Thr Asp Asn Thr Glu Tyr Asn Gln Lys Phe
    50                  55                  60

Lys Asp Lys Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Tyr Gly Asn Tyr Pro Leu Met Asp Tyr Trp Gly Gln Gly
            100                 105                 110

Thr Thr Val Thr Val Ser Ser
        115

<210> SEQ ID NO 109
<211> LENGTH: 1390
<212> TYPE: PRT
<213> ORGANISM: Homo sapiens

<400> SEQUENCE: 109

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp

```
              210                 215                 220
Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
                260                 265                 270

Thr Phe His Thr Arg Ile Ile Arg Phe Cys Ser Ile Asn Ser Gly Leu
                275                 280                 285

His Ser Tyr Met Glu Met Pro Leu Glu Cys Ile Leu Thr Glu Lys Arg
            290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
                340                 345                 350

Ser Ala Glu Pro Met Asp Arg Ser Ala Met Cys Ala Phe Pro Ile Lys
            355                 360                 365

Tyr Val Asn Asp Phe Phe Asn Lys Ile Val Asn Lys Asn Asn Val Arg
            370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
                420                 425                 430

Gln Phe Ser Glu Val Leu Leu Thr Ser Ile Ser Thr Phe Ile Lys Gly
            435                 440                 445

Asp Leu Thr Ile Ala Asn Leu Gly Thr Ser Glu Gly Arg Phe Met Gln
450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
                500                 505                 510

Ile Pro Leu Asn Gly Leu Gly Cys Arg His Phe Gln Ser Cys Ser Gln
            515                 520                 525

Cys Leu Ser Ala Pro Pro Phe Val Gln Cys Gly Trp Cys His Asp Lys
530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
                580                 585                 590

Asn Asn Lys Phe Asp Leu Lys Lys Thr Arg Val Leu Leu Gly Asn Glu
                595                 600                 605

Ser Cys Thr Leu Thr Leu Ser Glu Ser Thr Met Asn Thr Leu Lys Cys
            610                 615                 620

Thr Val Gly Pro Ala Met Asn Lys His Phe Asn Met Ser Ile Ile Ile
625                 630                 635                 640
```

-continued

```
Ser Asn Gly His Gly Thr Thr Gln Tyr Ser Thr Phe Ser Tyr Val Asp
                645                 650                 655

Pro Val Ile Thr Ser Ile Ser Pro Lys Tyr Gly Pro Met Ala Gly Gly
                660                 665                 670

Thr Leu Leu Thr Leu Thr Gly Asn Tyr Leu Asn Ser Gly Asn Ser Arg
                675                 680                 685

His Ile Ser Ile Gly Gly Lys Thr Cys Thr Leu Lys Ser Val Ser Asn
            690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
                740                 745                 750

Phe Ile Ser Gly Gly Ser Thr Ile Thr Gly Val Gly Lys Asn Leu Asn
                755                 760                 765

Ser Val Ser Val Pro Arg Met Val Ile Asn Val His Glu Ala Gly Arg
            770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
                805                 810                 815

Thr Lys Ala Phe Phe Met Leu Asp Gly Ile Leu Ser Lys Tyr Phe Asp
                820                 825                 830

Leu Ile Tyr Val His Asn Pro Val Phe Lys Pro Phe Glu Lys Pro Val
                835                 840                 845

Met Ile Ser Met Gly Asn Glu Asn Val Leu Glu Ile Lys Gly Asn Asp
            850                 855                 860

Ile Asp Pro Glu Ala Val Lys Gly Glu Val Leu Lys Val Gly Asn Lys
865                 870                 875                 880

Ser Cys Glu Asn Ile His Leu His Ser Glu Ala Val Leu Cys Thr Val
                885                 890                 895

Pro Asn Asp Leu Leu Lys Leu Asn Ser Glu Leu Asn Ile Glu Trp Lys
                900                 905                 910

Gln Ala Ile Ser Ser Thr Val Leu Gly Lys Val Ile Val Gln Pro Asp
                915                 920                 925

Gln Asn Phe Thr Gly Leu Ile Ala Gly Val Val Ser Ile Ser Thr Ala
            930                 935                 940

Leu Leu Leu Leu Leu Gly Phe Phe Leu Trp Leu Lys Lys Arg Lys Gln
945                 950                 955                 960

Ile Lys Asp Leu Gly Ser Glu Leu Val Arg Tyr Asp Ala Arg Val His
                965                 970                 975

Thr Pro His Leu Asp Arg Leu Val Ser Ala Arg Ser Val Ser Pro Thr
                980                 985                 990

Thr Glu Met Val Ser Asn Glu Ser Val Asp Tyr Arg Ala Thr Phe Pro
                995                1000                1005

Glu Asp Gln Phe Pro Asn Ser Ser Gln Asn Gly Ser Cys Arg Gln
            1010                1015                1020

Val Gln Tyr Pro Leu Thr Asp Met Ser Pro Ile Leu Thr Ser Gly
            1025                1030                1035

Asp Ser Asp Ile Ser Ser Pro Leu Leu Gln Asn Thr Val His Ile
            1040                1045                1050
```

Asp Leu Ser Ala Leu Asn Pro Glu Leu Val Gln Ala Val Gln His
    1055                1060                1065

Val Val Ile Gly Pro Ser Ser Leu Ile Val His Phe Asn Glu Val
    1070                1075                1080

Ile Gly Arg Gly His Phe Gly Cys Val Tyr His Gly Thr Leu Leu
    1085                1090                1095

Asp Asn Asp Gly Lys Lys Ile His Cys Ala Val Lys Ser Leu Asn
    1100                1105                1110

Arg Ile Thr Asp Ile Gly Glu Val Ser Gln Phe Leu Thr Glu Gly
    1115                1120                1125

Ile Ile Met Lys Asp Phe Ser His Pro Asn Val Leu Ser Leu Leu
    1130                1135                1140

Gly Ile Cys Leu Arg Ser Glu Gly Ser Pro Leu Val Val Leu Pro
    1145                1150                1155

Tyr Met Lys His Gly Asp Leu Arg Asn Phe Ile Arg Asn Glu Thr
    1160                1165                1170

His Asn Pro Thr Val Lys Asp Leu Ile Gly Phe Gly Leu Gln Val
    1175                1180                1185

Ala Lys Gly Met Lys Tyr Leu Ala Ser Lys Lys Phe Val His Arg
    1190                1195                1200

Asp Leu Ala Ala Arg Asn Cys Met Leu Asp Glu Lys Phe Thr Val
    1205                1210                1215

Lys Val Ala Asp Phe Gly Leu Ala Arg Asp Met Tyr Asp Lys Glu
    1220                1225                1230

Tyr Tyr Ser Val His Asn Lys Thr Gly Ala Lys Leu Pro Val Lys
    1235                1240                1245

Trp Met Ala Leu Glu Ser Leu Gln Thr Gln Lys Phe Thr Thr Lys
    1250                1255                1260

Ser Asp Val Trp Ser Phe Gly Val Leu Leu Trp Glu Leu Met Thr
    1265                1270                1275

Arg Gly Ala Pro Pro Tyr Pro Asp Val Asn Thr Phe Asp Ile Thr
    1280                1285                1290

Val Tyr Leu Leu Gln Gly Arg Arg Leu Leu Gln Pro Glu Tyr Cys
    1295                1300                1305

Pro Asp Pro Leu Tyr Glu Val Met Leu Lys Cys Trp His Pro Lys
    1310                1315                1320

Ala Glu Met Arg Pro Ser Phe Ser Glu Leu Val Ser Arg Ile Ser
    1325                1330                1335

Ala Ile Phe Ser Thr Phe Ile Gly Glu His Tyr Val His Val Asn
    1340                1345                1350

Ala Thr Tyr Val Asn Val Lys Cys Val Ala Pro Tyr Pro Ser Leu
    1355                1360                1365

Leu Ser Ser Glu Asp Asn Ala Asp Asp Glu Val Asp Thr Arg Pro
    1370                1375                1380

Ala Ser Phe Trp Glu Thr Ser
    1385                1390

<210> SEQ ID NO 110
<211> LENGTH: 1382
<212> TYPE: PRT
<213> ORGANISM: Rattus norvegicus

<400> SEQUENCE: 110

Met Lys Ala Pro Thr Ala Leu Ala Pro Gly Ile Leu Leu Leu Leu
1               5                   10                  15

```
Thr Leu Ala Gln Arg Ser His Gly Glu Cys Lys Glu Ala Leu Val Lys
            20                  25                  30

Ser Glu Met Asn Val Asn Met Lys Tyr Gln Leu Pro Asn Phe Thr Ala
        35                  40                  45

Glu Thr Pro Ile His Asn Val Val Leu Pro Gly His His Ile Tyr Leu
50                  55                  60

Gly Ala Thr Asn Tyr Ile Tyr Val Leu Asn Asp Lys Asp Leu Gln Lys
65                  70                  75                  80

Val Ser Glu Phe Lys Thr Gly Pro Val Val Glu His Pro Asp Cys Phe
                85                  90                  95

Pro Cys Gln Asp Cys Ser Ser Lys Ala Asn Val Ser Gly Gly Val Trp
            100                 105                 110

Lys Asp Asn Val Asn Met Ala Leu Leu Val Asp Thr Tyr Tyr Asp Asp
        115                 120                 125

Gln Leu Ile Ser Cys Gly Ser Val Asn Arg Gly Thr Cys Gln Arg His
130                 135                 140

Val Leu Pro Pro Asp Asn Ala Ala Asp Ile Gln Ser Glu Val His Cys
145                 150                 155                 160

Met Phe Ser Pro Leu Ala Glu Glu Ser Gly Gln Cys Pro Asp Cys
                165                 170                 175

Val Val Ser Ala Leu Gly Ala Lys Val Leu Leu Ser Glu Lys Asp Arg
            180                 185                 190

Phe Ile Asn Phe Phe Val Gly Asn Thr Ile Asn Ser Ser Tyr Pro Pro
        195                 200                 205

Asp Tyr Ser Leu His Ser Ile Ser Val Arg Arg Leu Lys Glu Thr Gln
210                 215                 220

Asp Gly Phe Lys Phe Leu Thr Asp Gln Ser Tyr Ile Asp Val Leu Pro
225                 230                 235                 240

Glu Phe Arg Asp Ser Tyr Pro Ile Lys Tyr Ile His Ala Phe Glu Ser
                245                 250                 255

Asn His Phe Ile Tyr Phe Leu Thr Val Gln Lys Glu Thr Leu Asp Ala
            260                 265                 270

Gln Thr Phe His Thr Arg Ile Ile Arg Phe Cys Ser Val Asp Ser Gly
        275                 280                 285

Leu His Ser Tyr Met Glu Met Pro Leu Glu Cys Ile Leu Thr Glu Lys
290                 295                 300

Arg Arg Lys Arg Ser Thr Arg Glu Glu Val Phe Asn Ile Leu Gln Ala
305                 310                 315                 320

Ala Tyr Val Ser Lys Pro Gly Ala Asn Leu Ala Lys Gln Ile Gly Ala
                325                 330                 335

Ser Pro Tyr Asp Asp Ile Leu Tyr Gly Val Phe Ala Gln Ser Lys Pro
            340                 345                 350

Asp Ser Ala Glu Pro Met Asn Arg Ser Ala Val Cys Ala Phe Pro Ile
        355                 360                 365

Lys Tyr Val Asn Asp Phe Phe Asn Lys Ile Val Asn Lys Asn Asn Val
            370                 375                 380

Arg Cys Leu Gln His Phe Tyr Gly Pro Asn His Glu His Cys Phe Asn
385                 390                 395                 400

Arg Thr Leu Leu Arg Asn Ser Ser Gly Cys Glu Val Arg Ser Asp Glu
                405                 410                 415

Tyr Arg Thr Glu Phe Thr Thr Ala Leu Gln Arg Val Asp Leu Phe Met
            420                 425                 430
```

```
Gly Arg Leu Asn His Val Leu Leu Thr Ser Ile Ser Thr Phe Ile Lys
            435                 440                 445

Gly Asp Leu Thr Ile Ala Asn Leu Gly Thr Ser Glu Gly Arg Phe Met
450                 455                 460

Gln Val Val Leu Ser Arg Thr Ala His Phe Thr Pro His Val Asn Phe
465                 470                 475                 480

Leu Leu Asp Ser Tyr Pro Val Ser Pro Glu Val Ile Val Glu His Pro
                485                 490                 495

Ser Asn Gln Asn Gly Tyr Thr Leu Val Val Thr Gly Lys Lys Ile Thr
            500                 505                 510

Lys Ile Pro Leu Asn Gly Leu Gly Cys Gly His Phe Gln Ser Cys Ser
        515                 520                 525

Gln Cys Leu Ser Pro Pro Tyr Phe Ile Gln Cys Gly Trp Cys His Asn
    530                 535                 540

Arg Cys Val His Ser Asn Glu Cys Pro Ser Gly Thr Trp Thr Gln Glu
545                 550                 555                 560

Ile Cys Leu Pro Ala Val Tyr Lys Val Phe Pro Thr Ser Ala Pro Leu
                565                 570                 575

Glu Gly Gly Thr Met Leu Thr Ile Cys Gly Trp Asp Phe Gly Phe Lys
            580                 585                 590

Lys Asn Asn Lys Phe Asp Leu Arg Lys Thr Lys Val Leu Leu Gly Asn
        595                 600                 605

Glu Ser Cys Thr Leu Thr Leu Ser Glu Ser Thr Thr Asn Thr Leu Lys
    610                 615                 620

Cys Thr Val Gly Pro Ala Met Ser Glu His Phe Asn Val Ser Val Ile
625                 630                 635                 640

Val Ser Asn Ser Arg Glu Thr Thr Gln Tyr Ser Ala Phe Ser Tyr Val
                645                 650                 655

Asp Pro Val Ile Thr Ser Ile Ser Pro Arg Tyr Gly Pro His Ala Gly
            660                 665                 670

Gly Thr Leu Leu Thr Leu Thr Gly Lys Tyr Leu Asn Ser Gly Asn Ser
        675                 680                 685

Arg His Ile Ser Ile Gly Gly Lys Thr Cys Thr Leu Lys Ser Val Ser
    690                 695                 700

Asp Ser Ile Leu Glu Cys Tyr Thr Pro Gly His Thr Val Ser Ala Glu
705                 710                 715                 720

Phe Pro Val Lys Leu Lys Ile Asp Leu Ala Asp Arg Val Thr Ser Ser
                725                 730                 735

Phe Ser Tyr Arg Glu Asp Pro Val Val Ser Glu Ile His Pro Thr Lys
            740                 745                 750

Ser Phe Ile Ser Gly Gly Ser Thr Ile Thr Gly Ile Gly Lys Asn Leu
        755                 760                 765

Asn Ser Val Ser Thr Pro Lys Leu Val Ile Glu Val His Asp Val Gly
    770                 775                 780

Val Asn Tyr Thr Val Ala Cys Gln His Arg Ser Ser Ser Glu Ile Ile
785                 790                 795                 800

Cys Cys Thr Thr Pro Ser Leu Arg Gln Leu Asp Leu Gln Leu Pro Leu
                805                 810                 815

Lys Thr Lys Ala Phe Phe Leu Leu Asp Gly Ile Leu Ser Lys His Phe
            820                 825                 830

Asp Leu Thr Tyr Val His Asp Pro Met Phe Lys Pro Phe Glu Lys Pro
        835                 840                 845

Val Met Ile Ser Met Gly Asn Glu Asn Val Val Glu Ile Lys Gly Asp
```

-continued

```
            850                 855                 860
Asp Ile Asp Pro Glu Ala Val Lys Gly Glu Val Leu Lys Val Gly Asn
865                 870                 875                 880

Lys Ser Cys Glu Asn Leu His Trp His Ser Glu Ala Leu Leu Cys Thr
                    885                 890                 895

Val Pro Ser Asp Leu Leu Lys Leu Asn Gly Gly Glu Leu Asn Ile Glu
                900                 905                 910

Trp Lys Gln Ala Val Ser Ser Thr Val Leu Gly Lys Val Ile Val Gln
            915                 920                 925

Pro Asp Gln Asn Phe Ala Gly Leu Ile Ile Gly Ala Val Ser Ile Ser
        930                 935                 940

Val Val Val Leu Leu Val Ser Gly Leu Phe Leu Trp Leu Arg Lys Arg
945                 950                 955                 960

Lys His Lys Asp Leu Gly Ser Glu Leu Val Arg Tyr Asp Ala Arg Val
                    965                 970                 975

His Thr Pro His Leu Asp Arg Leu Val Ser Ala Arg Ser Val Ser Pro
                980                 985                 990

Thr Thr Glu Met Val Ser Asn Glu Ser Val Asp Tyr Arg Ala Thr Phe
            995                 1000                1005

Pro Glu Asp Gln Phe Pro Asn Ser Ser Gln Asn Gly Ala Cys Arg
        1010                1015                1020

Gln Val Gln Tyr Leu Leu Thr Asp Leu Ser Pro Ile Leu Thr Ser
        1025                1030                1035

Gly Asp Ser Asp Ile Ser Ser Pro Leu Leu Gln Asn Thr Val His
        1040                1045                1050

Ile Asp Leu Ser Ala Leu Asn Pro Glu Leu Val Gln Ala Val Pro
        1055                1060                1065

His Val Val Ile Gly Pro Ser Ser Leu Ile Val His Phe Asn Glu
        1070                1075                1080

Val Ile Gly Arg Gly His Phe Gly Cys Val Tyr His Gly Thr Leu
        1085                1090                1095

Leu Asp Ser Asp Gly Lys Lys Ile His Cys Ala Val Lys Ser Leu
        1100                1105                1110

Asn Arg Ile Thr Asp Ile Glu Glu Val Ser Gln Phe Leu Thr Glu
        1115                1120                1125

Gly Ile Ile Met Lys Asp Phe Ser His Pro Asn Val Leu Ser Leu
        1130                1135                1140

Leu Gly Ile Cys Leu Arg Ser Glu Gly Ser Pro Leu Val Val Leu
        1145                1150                1155

Pro Tyr Met Lys His Gly Asp Leu Arg Asn Phe Ile Arg Asn Glu
        1160                1165                1170

Thr His Asn Pro Thr Val Lys Asp Leu Ile Gly Phe Gly Leu Gln
        1175                1180                1185

Val Ala Lys Gly Met Lys Tyr Leu Val Ser Lys Lys Phe Val His
        1190                1195                1200

Arg Asp Leu Ala Ala Arg Asn Cys Met Leu Asp Glu Lys Phe Thr
        1205                1210                1215

Val Lys Val Ala Asp Phe Gly Leu Ala Arg Asp Met Tyr Asp Lys
        1220                1225                1230

Glu Tyr Tyr Ser Val His Asn Lys Thr Gly Ala Lys Leu Pro Val
        1235                1240                1245

Lys Trp Met Ala Leu Glu Ser Leu Gln Thr Gln Lys Phe Thr Thr
        1250                1255                1260
```

Lys Ser Asp Val Trp Ser Phe Gly Val Leu Leu Trp Glu Leu Met
1265              1270              1275

Thr Arg Gly Ala Pro Pro Tyr Pro Asp Val Asn Thr Phe Asp Ile
1280              1285              1290

Thr Ile Tyr Leu Leu Gln Gly Arg Arg Leu Leu Gln Pro Glu Tyr
1295              1300              1305

Cys Pro Asp Ala Leu Tyr Glu Val Met Leu Lys Cys Trp His Pro
1310              1315              1320

Lys Ala Glu Met Arg Pro Ser Val Ser Glu Leu Val Ser Arg Ile
1325              1330              1335

Ser Ser Ile Phe Ser Thr Phe Ile Gly Glu His Tyr Val His Val
1340              1345              1350

Asn Ala Thr Tyr Val Asn Val Lys Cys Val Ala Pro Tyr Pro Ser
1355              1360              1365

Leu Leu Pro Ser Gln Asp Asn Ile Asp Gly Glu Ala Asn Thr
1370              1375              1380

<210> SEQ ID NO 111
<211> LENGTH: 1379
<212> TYPE: PRT
<213> ORGANISM: Mus musculus

<400> SEQUENCE: 111

Met Lys Ala Pro Thr Val Leu Ala Pro Gly Ile Leu Val Leu Leu
1               5                   10                  15

Ser Leu Val Gln Arg Ser His Gly Glu Cys Lys Glu Ala Leu Val Lys
        20                  25                  30

Ser Glu Met Asn Val Asn Met Lys Tyr Gln Leu Pro Asn Phe Thr Ala
        35                  40                  45

Glu Thr Pro Ile Gln Asn Val Val Leu His Gly His His Ile Tyr Leu
    50                  55                  60

Gly Ala Thr Asn Tyr Ile Tyr Val Leu Asn Asp Lys Asp Leu Gln Lys
65                  70                  75                  80

Val Ser Glu Phe Lys Thr Gly Pro Val Leu Glu His Pro Asp Cys Leu
                85                  90                  95

Pro Cys Arg Asp Cys Ser Ser Lys Ala Asn Ser Ser Gly Gly Val Trp
            100                 105                 110

Lys Asp Asn Ile Asn Met Ala Leu Leu Val Asp Thr Tyr Tyr Asp Asp
        115                 120                 125

Gln Leu Ile Ser Cys Gly Ser Val Asn Arg Gly Thr Cys Gln Arg His
        130                 135                 140

Val Leu Pro Pro Asp Asn Ser Ala Asp Ile Gln Ser Glu Val His Cys
145                 150                 155                 160

Met Phe Ser Pro Glu Glu Ser Gly Gln Cys Pro Asp Cys Val Val
                165                 170                 175

Ser Ala Leu Gly Ala Lys Val Leu Leu Ser Glu Lys Asp Arg Phe Ile
            180                 185                 190

Asn Phe Phe Val Gly Asn Thr Ile Asn Ser Ser Tyr Pro Pro Gly Tyr
        195                 200                 205

Ser Leu His Ser Ile Ser Val Arg Arg Leu Lys Glu Thr Gln Asp Gly
        210                 215                 220

Phe Lys Phe Leu Thr Asp Gln Ser Tyr Ile Asp Val Leu Pro Glu Phe
225                 230                 235                 240

Leu Asp Ser Tyr Pro Ile Lys Tyr Ile His Ala Phe Glu Ser Asn His

```
                      245                 250                 255
        Phe Ile Tyr Phe Leu Thr Val Gln Lys Glu Thr Leu Asp Ala Gln Thr
                        260                 265                 270

Phe His Thr Arg Ile Ile Arg Phe Cys Ser Val Asp Ser Gly Leu His
                        275                 280                 285

Ser Tyr Met Glu Met Pro Leu Glu Cys Ile Leu Thr Glu Lys Arg Arg
                        290                 295                 300

Lys Arg Ser Thr Arg Glu Glu Val Phe Asn Ile Leu Gln Ala Ala Tyr
        305                 310                 315                 320

Val Ser Lys Pro Gly Ala Asn Leu Ala Lys Gln Ile Gly Ala Ser Pro
                        325                 330                 335

Ser Asp Asp Ile Leu Phe Gly Val Phe Ala Gln Ser Lys Pro Asp Ser
                        340                 345                 350

Ala Glu Pro Val Asn Arg Ser Ala Val Cys Ala Phe Pro Ile Lys Tyr
                        355                 360                 365

Val Asn Asp Phe Phe Asn Lys Ile Val Asn Lys Asn Asn Val Arg Cys
                        370                 375                 380

Leu Gln His Phe Tyr Gly Pro Asn His Glu His Cys Phe Asn Arg Thr
        385                 390                 395                 400

Leu Leu Arg Asn Ser Ser Gly Cys Glu Ala Arg Ser Asp Glu Tyr Arg
                        405                 410                 415

Thr Glu Phe Thr Thr Ala Leu Gln Arg Val Asp Leu Phe Met Gly Arg
                        420                 425                 430

Leu Asn Gln Val Leu Leu Thr Ser Ile Ser Thr Phe Ile Lys Gly Asp
                        435                 440                 445

Leu Thr Ile Ala Asn Leu Gly Thr Ser Glu Gly Arg Phe Met Gln Val
        450                 455                 460

Val Leu Ser Arg Thr Ala His Leu Thr Pro His Val Asn Phe Leu Leu
        465                 470                 475                 480

Asp Ser His Pro Val Ser Pro Glu Val Ile Val Glu His Pro Ser Asn
                        485                 490                 495

Gln Asn Gly Tyr Thr Leu Val Val Thr Gly Lys Lys Ile Thr Lys Ile
                        500                 505                 510

Pro Leu Asn Gly Leu Gly Cys Gly His Phe Gln Ser Cys Ser Gln Cys
                        515                 520                 525

Leu Ser Ala Pro Tyr Phe Ile Gln Cys Gly Trp Cys His Asn Gln Cys
                        530                 535                 540

Val Arg Phe Asp Glu Cys Pro Ser Gly Thr Trp Thr Gln Glu Ile Cys
        545                 550                 555                 560

Leu Pro Ala Val Tyr Lys Val Phe Pro Thr Ser Ala Pro Leu Glu Gly
                        565                 570                 575

Gly Thr Val Leu Thr Ile Cys Gly Trp Asp Phe Gly Phe Arg Lys Asn
                        580                 585                 590

Asn Lys Phe Asp Leu Arg Lys Thr Lys Val Leu Leu Gly Asn Glu Ser
                        595                 600                 605

Cys Thr Leu Thr Leu Ser Glu Ser Thr Thr Asn Thr Leu Lys Cys Thr
        610                 615                 620

Val Gly Pro Ala Met Ser Glu His Phe Asn Val Ser Val Ile Ile Ser
        625                 630                 635                 640

Asn Ser Arg Glu Thr Thr Gln Tyr Ser Ala Phe Ser Tyr Val Asp Pro
                        645                 650                 655

Val Ile Thr Ser Ile Ser Pro Arg Tyr Gly Pro Gln Ala Gly Gly Thr
                        660                 665                 670
```

```
Leu Leu Thr Leu Thr Gly Lys Tyr Leu Asn Ser Gly Asn Ser Arg His
        675                 680                 685

Ile Ser Ile Gly Gly Lys Thr Cys Thr Leu Lys Ser Val Ser Asp Ser
690                 695                 700

Ile Leu Glu Cys Tyr Thr Pro Ala Gln Thr Thr Ser Asp Glu Phe Pro
705                 710                 715                 720

Val Lys Leu Lys Ile Asp Leu Ala Asn Arg Glu Thr Ser Ser Phe Ser
                725                 730                 735

Tyr Arg Glu Asp Pro Val Val Tyr Glu Ile His Pro Thr Lys Ser Phe
                740                 745                 750

Ile Ser Gly Gly Ser Thr Ile Thr Gly Ile Gly Lys Thr Leu Asn Ser
                755                 760                 765

Val Ser Leu Pro Lys Leu Val Ile Asp Val His Glu Val Gly Val Asn
770                 775                 780

Tyr Thr Val Ala Cys Gln His Arg Ser Asn Ser Glu Ile Ile Cys Cys
785                 790                 795                 800

Thr Thr Pro Ser Leu Lys Gln Leu Gly Leu Gln Leu Pro Leu Lys Thr
                805                 810                 815

Lys Ala Phe Phe Leu Leu Asp Gly Ile Leu Ser Lys His Phe Asp Leu
                820                 825                 830

Thr Tyr Val His Asn Pro Val Phe Glu Pro Phe Glu Lys Pro Val Met
                835                 840                 845

Ile Ser Met Gly Asn Glu Asn Val Val Glu Ile Lys Gly Asn Asn Ile
                850                 855                 860

Asp Pro Glu Ala Val Lys Gly Glu Val Leu Lys Val Gly Asn Gln Ser
865                 870                 875                 880

Cys Glu Ser Leu His Trp His Ser Gly Ala Val Leu Cys Thr Val Pro
                885                 890                 895

Ser Asp Leu Leu Lys Leu Asn Ser Glu Leu Asn Ile Glu Trp Lys Gln
                900                 905                 910

Ala Val Ser Ser Thr Val Leu Gly Lys Val Ile Val Gln Pro Asp Gln
                915                 920                 925

Asn Phe Ala Gly Leu Ile Ile Gly Ala Val Ser Ile Ser Val Val Val
                930                 935                 940

Leu Leu Leu Ser Gly Leu Phe Leu Trp Met Arg Lys Arg Lys His Lys
945                 950                 955                 960

Asp Leu Gly Ser Glu Leu Val Arg Tyr Asp Ala Arg Val His Thr Pro
                965                 970                 975

His Leu Asp Arg Leu Val Ser Ala Arg Ser Val Ser Pro Thr Thr Glu
                980                 985                 990

Met Val Ser Asn Glu Ser Val Asp Tyr Arg Ala Thr Phe Pro Glu Asp
                995                1000                1005

Gln Phe Pro Asn Ser Ser Gln Asn Gly Ala Cys Arg Gln Val Gln
        1010                1015                1020

Tyr Pro Leu Thr Asp Leu Ser Pro Ile Leu Thr Ser Gly Asp Ser
        1025                1030                1035

Asp Ile Ser Ser Pro Leu Leu Gln Asn Thr Val His Ile Asp Leu
        1040                1045                1050

Ser Ala Leu Asn Pro Glu Leu Val Gln Ala Val Gln His Val Val
        1055                1060                1065

Ile Gly Pro Ser Ser Leu Ile Val His Phe Asn Glu Val Ile Gly
        1070                1075                1080
```

Arg Gly His Phe Gly Cys Val Tyr His Gly Thr Leu Leu Asp Asn
    1085                1090                1095

Asp Gly Lys Lys Ile His Cys Ala Val Lys Ser Leu Asn Arg Ile
    1100                1105                1110

Thr Asp Ile Glu Glu Val Ser Gln Phe Leu Thr Glu Gly Ile Ile
    1115                1120                1125

Met Lys Asp Phe Ser His Pro Asn Val Leu Ser Leu Leu Gly Ile
    1130                1135                1140

Cys Leu Arg Ser Glu Gly Ser Pro Leu Val Val Leu Pro Tyr Met
    1145                1150                1155

Lys His Gly Asp Leu Arg Asn Phe Ile Arg Asn Glu Thr His Asn
    1160                1165                1170

Pro Thr Val Lys Asp Leu Ile Gly Phe Gly Leu Gln Val Ala Lys
    1175                1180                1185

Gly Met Lys Tyr Leu Ala Ser Lys Lys Phe Val His Arg Asp Leu
    1190                1195                1200

Ala Ala Arg Asn Cys Met Leu Asp Glu Lys Phe Thr Val Lys Val
    1205                1210                1215

Ala Asp Phe Gly Leu Ala Arg Asp Met Tyr Asp Lys Glu Tyr Tyr
    1220                1225                1230

Ser Val His Asn Lys Thr Gly Ala Lys Leu Pro Val Lys Trp Met
    1235                1240                1245

Ala Leu Glu Ser Leu Gln Thr Gln Lys Phe Thr Thr Lys Ser Asp
    1250                1255                1260

Val Trp Ser Phe Gly Val Leu Leu Trp Glu Leu Met Thr Arg Gly
    1265                1270                1275

Ala Pro Pro Tyr Pro Asp Val Asn Thr Phe Asp Ile Thr Ile Tyr
    1280                1285                1290

Leu Leu Gln Gly Arg Arg Leu Leu Gln Pro Glu Tyr Cys Pro Asp
    1295                1300                1305

Ala Leu Tyr Glu Val Met Leu Lys Cys Trp His Pro Lys Ala Glu
    1310                1315                1320

Met Arg Pro Ser Phe Ser Glu Leu Val Ser Arg Ile Ser Ser Ile
    1325                1330                1335

Phe Ser Thr Phe Ile Gly Glu His Tyr Val His Val Asn Ala Thr
    1340                1345                1350

Tyr Val Asn Val Lys Cys Val Ala Pro Tyr Pro Ser Leu Leu Pro
    1355                1360                1365

Ser Gln Asp Asn Ile Asp Gly Glu Gly Asn Thr
    1370                1375

<210> SEQ ID NO 112
<211> LENGTH: 1382
<212> TYPE: PRT
<213> ORGANISM: Canis familiaris

<400> SEQUENCE: 112

Met Lys Ala Pro Ala Val Leu Ala Pro Gly Ile Leu Val Leu Leu Phe
1               5                   10                  15

Thr Leu Val Gln Lys Ser Tyr Gly Glu Cys Lys Glu Ala Leu Val Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Val Leu His Lys His His Ile Tyr Leu
    50                  55                  60

```
Gly Ala Val Asn Tyr Ile Tyr Val Leu Asn Asp Lys Asp Leu Gln Lys
 65                  70                  75                  80

Val Ala Glu Tyr Lys Thr Gly Pro Val Leu Glu His Pro Asp Cys Ser
                 85                  90                  95

Pro Cys Gln Asp Cys Ser His Lys Ala Asn Leu Ser Gly Gly Val Trp
            100                 105                 110

Glu Asp Asn Ile Asn Met Ala Leu Leu Val Asp Thr Tyr Tyr Asp Asp
        115                 120                 125

Gln Leu Ile Ser Cys Gly Ser Val His Arg Gly Thr Cys Gln Arg His
            130                 135                 140

Ile Leu Pro Pro Ser Asn Ile Ala Asp Ile Gln Ser Glu Val His Cys
145                 150                 155                 160

Met Tyr Ser Ser Gln Ala Asp Glu Pro Ser Gln Cys Pro Asp Cys
                165                 170                 175

Val Val Ser Ala Leu Gly Thr Lys Val Leu Ile Ser Glu Lys Asp Arg
                180                 185                 190

Phe Ile Asn Phe Phe Val Gly Asn Thr Ile Asn Ser Ser Asp His Pro
                195                 200                 205

Asp His Ser Leu His Ser Ile Ser Val Arg Arg Leu Lys Glu Thr Gln
        210                 215                 220

Asp Gly Phe Lys Phe Leu Thr Asp Gln Ser Tyr Ile Asp Val Leu Pro
225                 230                 235                 240

Glu Phe Arg Asp Ser Tyr Pro Ile Lys Tyr Val His Ala Phe Glu Ser
                245                 250                 255

Asn His Phe Ile Tyr Phe Leu Thr Val Gln Arg Glu Thr Leu Asp Ala
                260                 265                 270

Gln Thr Phe His Thr Arg Ile Ile Arg Phe Cys Ser Val Asp Ser Gly
        275                 280                 285

Leu His Ser Tyr Met Glu Met Pro Leu Glu Cys Ile Leu Thr Glu Lys
        290                 295                 300

Arg Arg Lys Arg Ser Thr Arg Glu Glu Val Phe Asn Ile Leu Gln Ala
305                 310                 315                 320

Ala Tyr Val Ser Lys Pro Gly Ala His Leu Ala Lys Gln Ile Gly Ala
                325                 330                 335

Asn Leu Asn Asp Asp Ile Leu Tyr Gly Val Phe Ala Gln Ser Lys Pro
                340                 345                 350

Asp Ser Ala Glu Pro Met Asn Arg Ser Ala Val Cys Ala Phe Pro Ile
        355                 360                 365

Lys Tyr Val Asn Glu Phe Phe Asn Lys Ile Val Asn Lys Asn Asn Val
        370                 375                 380

Arg Cys Leu Gln His Phe Tyr Gly Pro Asn His Glu His Cys Phe Asn
385                 390                 395                 400

Arg Thr Leu Leu Arg Asn Ser Ser Gly Cys Glu Ala Arg Asn Asp Glu
                405                 410                 415

Tyr Arg Thr Glu Phe Thr Thr Ala Leu Gln Arg Val Asp Leu Phe Met
                420                 425                 430

Gly Gln Phe Asn Gln Val Leu Leu Thr Ser Ile Ser Thr Phe Ile Lys
            435                 440                 445

Gly Asp Leu Thr Ile Ala Asn Leu Gly Thr Ser Glu Gly Arg Phe Met
        450                 455                 460

Gln Val Val Val Ser Arg Ser Gly Leu Ser Thr Pro His Val Asn Phe
465                 470                 475                 480
```

```
Arg Leu Asp Ser His Pro Val Ser Pro Glu Ala Ile Val Glu His Pro
                485                 490                 495

Leu Asn Gln Asn Gly Tyr Thr Leu Val Val Thr Gly Lys Lys Ile Thr
        500                 505                 510

Arg Ile Pro Leu Asn Gly Leu Gly Cys Glu His Phe Gln Ser Cys Ser
    515                 520                 525

Gln Cys Leu Ser Ala Pro Pro Phe Val Gln Cys Gly Trp Cys His Asp
530                 535                 540

Arg Cys Val His Leu Glu Glu Cys Pro Thr Gly Ala Trp Thr Gln Glu
545                 550                 555                 560

Val Cys Leu Pro Ala Ile Tyr Glu Val Phe Pro Thr Ser Ala Pro Leu
                565                 570                 575

Glu Gly Gly Thr Val Leu Thr Val Cys Gly Trp Asp Phe Gly Phe Arg
            580                 585                 590

Arg Asn Asn Lys Phe Asp Leu Lys Lys Thr Lys Val Phe Leu Gly Asn
    595                 600                 605

Glu Ser Cys Thr Leu Thr Leu Ser Glu Ser Thr Thr Asn Met Leu Lys
        610                 615                 620

Cys Thr Val Gly Pro Ala Val Asn Glu His Phe Asn Ile Ser Ile Ile
625                 630                 635                 640

Ile Ser Asn Gly Arg Gly Thr Ala Gln Tyr Ser Thr Phe Ser Tyr Val
                645                 650                 655

Asp Pro Ile Ile Thr Ser Ile Ser Pro Ser Tyr Gly Pro Lys Asn Gly
            660                 665                 670

Gly Thr Leu Leu Thr Leu Thr Gly Lys Tyr Leu Asn Ser Gly Asn Ser
        675                 680                 685

Arg His Ile Ser Met Gly Gly Lys Thr Cys Thr Leu Lys Ser Val Ser
    690                 695                 700

Asp Ser Ile Leu Glu Cys Tyr Thr Pro Ala Gln Ala Thr Ala Thr Glu
705                 710                 715                 720

Phe Pro Ile Lys Leu Lys Ile Asp Leu Ala Asn Arg Glu Met Asn Ser
                725                 730                 735

Phe Ser Tyr Gln Glu Asp Pro Ile Val Tyr Ala Ile His Pro Thr Lys
            740                 745                 750

Ser Phe Ile Ser Gly Gly Ser Thr Ile Thr Ala Val Gly Lys Asn Leu
        755                 760                 765

Asn Ser Val Ser Val Leu Arg Met Val Ile Asp Val His Glu Thr Arg
    770                 775                 780

Arg Asn Phe Thr Val Ala Cys Gln His Arg Ser Asn Ser Glu Ile Ile
785                 790                 795                 800

Cys Cys Thr Thr Pro Ser Leu Gln Gln Leu Asn Leu Gln Leu Pro Leu
                805                 810                 815

Lys Thr Lys Ala Phe Phe Met Leu Asp Gly Ile His Ser Lys Tyr Phe
            820                 825                 830

Asp Leu Ile Tyr Val His Asn Pro Val Phe Lys Pro Phe Glu Lys Pro
        835                 840                 845

Val Met Ile Ser Ile Gly Asn Glu Asn Val Leu Glu Ile Lys Gly Asn
    850                 855                 860

Asp Ile Asp Pro Glu Ala Val Lys Gly Glu Val Leu Lys Val Gly Asn
865                 870                 875                 880

Lys Ser Cys Glu Thr Ile Tyr Ser Asp Ser Lys Ala Val Leu Cys Lys
                885                 890                 895

Val Pro Asn Asp Leu Leu Lys Leu Asn Asn Glu Leu Asn Ile Glu Trp
```

```
                900            905             910
Lys Gln Ala Val Ser Thr Val Leu Gly Lys Val Ile Val Gln Pro
        915                 920                 925
Asp Gln Asn Phe Thr Gly Leu Ile Ala Gly Val Ile Ser Ile Ser Thr
        930                 935                 940
Ile Val Leu Leu Leu Leu Gly Leu Phe Leu Trp Leu Arg Lys Lys
945                 950                 955                 960
Gln Ile Lys Asp Leu Gly Ser Glu Leu Val Arg Tyr Asp Ala Arg Val
            965                 970                 975
His Thr Pro His Leu Asp Arg Leu Val Ser Ala Arg Ser Val Ser Pro
            980                 985                 990
Thr Thr Glu Met Val Ser Asn Glu Ser Val Asp Tyr Arg Ala Thr Phe
        995                 1000                1005
Pro Glu Asp Gln Phe Pro Asn Ser Ser Gln Asn Gly Ser Cys Arg
    1010                1015                1020
Gln Val Gln Tyr Pro Leu Thr Asp Leu Ser Pro Met Leu Thr Ser
    1025                1030                1035
Gly Asp Ser Asp Ile Ser Ser Pro Leu Leu Gln Asn Thr Val His
    1040                1045                1050
Ile Asp Leu Ser Ala Leu Asn Pro Glu Leu Val Gln Ala Val Gln
    1055                1060                1065
His Val Val Ile Gly Pro Ser Ser Leu Ile Val His Phe Asn Glu
    1070                1075                1080
Val Ile Gly Arg Gly His Phe Gly Cys Val Tyr His Gly Thr Leu
    1085                1090                1095
Leu Asp Asn Asp Asp Lys Lys Ile His Cys Ala Val Lys Ser Leu
    1100                1105                1110
Asn Arg Ile Thr Asp Ile Gly Glu Val Ser Gln Phe Leu Thr Glu
    1115                1120                1125
Gly Ile Ile Met Lys Asp Phe Ser His Pro Asn Val Leu Ser Leu
    1130                1135                1140
Leu Gly Ile Cys Leu Arg Ser Glu Gly Ser Pro Leu Val Val Leu
    1145                1150                1155
Pro Tyr Met Lys His Gly Asp Leu Arg Asn Phe Ile Arg Asn Glu
    1160                1165                1170
Thr His Asn Pro Thr Val Lys Asp Leu Ile Gly Phe Gly Leu Gln
    1175                1180                1185
Val Ala Lys Gly Met Lys Tyr Leu Ala Ser Lys Lys Phe Val His
    1190                1195                1200
Arg Asp Leu Ala Ala Arg Asn Cys Met Leu Asp Glu Lys Phe Thr
    1205                1210                1215
Val Lys Val Ala Asp Phe Gly Leu Ala Arg Asp Met Tyr Asp Lys
    1220                1225                1230
Glu Tyr Tyr Ser Val His Asn Lys Thr Gly Ala Lys Leu Pro Val
    1235                1240                1245
Lys Trp Met Ala Leu Glu Ser Leu Gln Thr Gln Lys Phe Thr Thr
    1250                1255                1260
Lys Ser Asp Val Trp Ser Phe Gly Val Leu Leu Trp Glu Leu Met
    1265                1270                1275
Thr Arg Gly Ala Pro Pro Tyr Pro Asp Val Asn Thr Phe Asp Ile
    1280                1285                1290
Thr Val Tyr Leu Leu Gln Gly Arg Arg Leu Leu Gln Pro Glu Tyr
    1295                1300                1305
```

-continued

Cys Pro Asp Pro Leu Tyr Glu Val Met Leu Lys Cys Trp His Pro
1310                1315                1320

Arg Ala Glu Leu Arg Pro Ser Phe Ser Glu Leu Val Ser Arg Ile
1325                1330                1335

Ser Ala Ile Phe Ser Thr Phe Ile Gly Glu His Tyr Val His Val
1340                1345                1350

Asn Ala Thr Tyr Val Asn Val Lys Cys Val Ala Pro Tyr Pro Ser
1355                1360                1365

Leu Leu Ser Ser Gln Asp Asn Ile Asp Gly Glu Gly Asp Thr
         1370                1375                1380

<210> SEQ ID NO 113
<211> LENGTH: 1381
<212> TYPE: PRT
<213> ORGANISM: Macaca mulatta

<400> SEQUENCE: 113

Met Lys Ala Pro Ala Val Leu Val Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Ala Ile Gln Asn Val Ile Leu His Glu His His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Asn Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro His
        195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Ile His Ala Phe Glu Ser Asn
                245                 250                 255

Asn Phe Ile Tyr Phe Leu Thr Val Gln Arg Glu Thr Leu Asn Ala Gln
            260                 265                 270

Thr Phe His Thr Arg Ile Ile Arg Phe Cys Ser Leu Asn Ser Gly Leu
        275                 280                 285

His Ser Tyr Met Glu Met Pro Leu Glu Cys Ile Leu Thr Glu Lys Arg

-continued

```
            290                 295                 300
Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
                340                 345                 350

Ser Ala Glu Pro Met Asp Arg Ser Ala Met Cys Ala Phe Pro Ile Lys
                355                 360                 365

Tyr Val Asn Asp Phe Phe Asn Lys Ile Val Asn Lys Asn Asn Val Arg
                370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Ala Glu Phe Thr Thr Ala Leu Gln Arg Val Asp Leu Phe Met Gly
                420                 425                 430

Gln Phe Ser Glu Val Leu Leu Thr Ser Ile Ser Thr Phe Val Lys Gly
                435                 440                 445

Asp Leu Thr Ile Ala Asn Leu Gly Thr Ser Glu Gly Arg Phe Met Gln
                450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Pro Leu
                485                 490                 495

Asn Gln Asn Gly Tyr Thr Leu Val Val Thr Gly Lys Lys Ile Thr Lys
                500                 505                 510

Ile Pro Leu Asn Gly Leu Gly Cys Arg His Phe Gln Ser Cys Ser Gln
                515                 520                 525

Cys Leu Ser Ala Pro Pro Phe Val Gln Cys Gly Trp Cys His Asp Lys
530                 535                 540

Cys Val Arg Ser Glu Glu Cys Pro Ser Gly Thr Trp Thr Gln Gln Ile
545                 550                 555                 560

Cys Leu Pro Ala Ile Tyr Lys Val Phe Pro Thr Ser Ala Pro Leu Glu
                565                 570                 575

Gly Gly Thr Arg Leu Thr Ile Cys Gly Trp Asp Phe Gly Phe Arg Arg
                580                 585                 590

Asn Asn Lys Phe Asp Leu Lys Lys Thr Arg Val Leu Leu Gly Asn Glu
                595                 600                 605

Ser Cys Thr Leu Thr Leu Ser Glu Ser Thr Met Asn Thr Leu Lys Cys
                610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Ile Ile Thr Ser Ile Ser Pro Lys Tyr Gly Pro Met Ala Gly Gly
                660                 665                 670

Thr Leu Leu Thr Leu Thr Gly Asn Tyr Leu Asn Ser Gly Asn Ser Arg
                675                 680                 685

His Ile Ser Ile Gly Gly Lys Thr Cys Thr Leu Lys Ser Val Ser Asn
                690                 695                 700

Ser Ile Leu Glu Cys Tyr Thr Pro Ala Gln Thr Ile Ser Thr Glu Phe
705                 710                 715                 720
```

```
Ala Val Lys Leu Lys Ile Asp Leu Ala Asn Arg Glu Thr Ser Ile Phe
            725                 730                 735
Ser Tyr Arg Glu Asp Pro Ile Val Tyr Glu Ile His Pro Thr Lys Ser
            740                 745                 750
Phe Ile Ser Gly Gly Ser Thr Ile Thr Gly Val Gly Lys Asn Leu His
            755                 760                 765
Ser Val Ser Val Pro Arg Met Val Ile Asn Val His Glu Ala Gly Arg
    770                 775                 780
Asn Phe Thr Val Ala Cys Gln His Arg Ser Asn Ser Glu Ile Ile Cys
785                 790                 795                 800
Cys Thr Thr Pro Ser Leu Gln Gln Leu Asn Leu Gln Leu Pro Leu Lys
                805                 810                 815
Thr Lys Ala Phe Phe Met Leu Asp Gly Ile Leu Ser Lys Tyr Phe Asp
                820                 825                 830
Leu Ile Tyr Val His Asn Pro Val Phe Lys Pro Phe Glu Lys Pro Val
            835                 840                 845
Met Ile Ser Met Gly Asn Glu Asn Val Leu Glu Ile Lys Gly Asn Asp
    850                 855                 860
Ile Asp Pro Glu Ala Val Lys Gly Glu Val Leu Lys Val Gly Asn Lys
865                 870                 875                 880
Ser Cys Glu Asn Ile His Leu His Ser Glu Ala Val Leu Cys Thr Val
                885                 890                 895
Pro Asn Asp Leu Leu Lys Leu Asn Ser Glu Leu Asn Ile Glu Trp Lys
                900                 905                 910
Gln Ala Ile Ser Ser Thr Val Leu Gly Lys Val Ile Val Gln Pro Asp
            915                 920                 925
Gln Asn Phe Thr Gly Leu Ile Ala Gly Val Val Ser Ile Ser Ile Ala
    930                 935                 940
Leu Leu Leu Leu Leu Gly Leu Phe Leu Trp Leu Lys Lys Arg Lys Gln
945                 950                 955                 960
Ile Lys Asp Leu Gly Ser Glu Leu Val Arg Tyr Asp Ala Arg Val His
                965                 970                 975
Thr Pro His Leu Asp Arg Leu Val Ser Ala Arg Ser Val Ser Pro Thr
            980                 985                 990
Thr Glu Met Val Ser Asn Glu Ser  Val Asp Tyr Arg Ala  Thr Phe Pro
    995                 1000                1005
Glu Asp Gln Phe Pro Asn Ser  Ser Gln Asn Gly Ser  Cys Arg Gln
    1010                1015                1020
Val Gln Tyr Pro Leu Thr Asp  Met Ser Pro Ile Leu  Thr Ser Gly
    1025                1030                1035
Asp Ser Asp Ile Ser Ser Pro  Leu Leu Gln Asn Thr  Val His Ile
    1040                1045                1050
Asp Leu Ser Ala Leu Asn Pro  Glu Leu Val Gln Ala  Val Gln His
    1055                1060                1065
Val Val Ile Gly Pro Ser Ser  Leu Ile Val His Phe  Asn Glu Val
    1070                1075                1080
Ile Gly Arg Gly His Phe Gly  Cys Val Tyr His Gly  Thr Leu Leu
    1085                1090                1095
Asp Asn Asp Gly Lys Lys Ile  His Cys Ala Val Lys  Ser Leu Asn
    1100                1105                1110
Arg Ile Thr Asp Ile Gly Glu  Val Ser Gln Phe Leu  Thr Glu Gly
    1115                1120                1125
```

```
Ile Ile Met Lys Asp Phe Ser His Pro Asn Val Leu Ser Leu Leu
1130                    1135              1140

Gly Ile Cys Leu Arg Ser Glu Gly Ser Pro Leu Val Val Leu Pro
1145                    1150              1155

Tyr Met Lys His Gly Asp Leu Arg Asn Phe Ile Arg Asn Glu Thr
1160                    1165              1170

His Asn Pro Thr Val Lys Asp Leu Ile Gly Phe Gly Leu Gln Val
1175                    1180              1185

Ala Lys Gly Met Lys Tyr Leu Ala Ser Lys Lys Phe Val His Arg
1190                    1195              1200

Asp Leu Ala Ala Arg Asn Cys Met Leu Asp Glu Lys Phe Thr Val
1205                    1210              1215

Lys Val Ala Asp Phe Gly Leu Ala Arg Asp Met Tyr Asp Lys Glu
1220                    1225              1230

Tyr Tyr Ser Val His Asn Lys Thr Gly Ala Lys Leu Pro Val Lys
1235                    1240              1245

Trp Met Ala Leu Glu Ser Leu Gln Thr Gln Lys Phe Thr Thr Lys
1250                    1255              1260

Ser Asp Val Trp Ser Phe Gly Val Leu Leu Trp Glu Leu Met Thr
1265                    1270              1275

Arg Gly Ala Pro Pro Tyr Pro Asp Val Asn Thr Phe Asp Ile Thr
1280                    1285              1290

Val Tyr Leu Leu Gln Gly Arg Arg Leu Leu Gln Pro Glu Tyr Cys
1295                    1300              1305

Pro Asp Pro Leu Tyr Glu Val Met Leu Lys Cys Trp His Pro Lys
1310                    1315              1320

Ala Glu Met Arg Pro Ser Phe Ser Glu Leu Val Ser Arg Ile Ser
1325                    1330              1335

Ala Ile Phe Ser Thr Phe Ile Gly Glu His Tyr Val His Val Asn
1340                    1345              1350

Ala Thr Tyr Val Asn Val Lys Cys Val Ala Pro Tyr Pro Ser Leu
1355                    1360              1365

Leu Ser Ser Glu Asp Asn Ala Asp Asp Glu Val Asp Thr
1370                    1375              1380
```

CMET MONOCLONAL BINDING AGENTS, DRUG CONJUGATES THEREOF AND USES THEREOF

RELATED PATENT APPLICATIONS

This patent application is a national phase filing of, and claims the benefit of, International Patent Application No. PCT/JP2017/035259 filed on Sep. 28, 2017, entitled CMET MONOCLONAL BINDING AGENTS, DRUG CONJUGATES THEREOF AND USES THEREOF, and naming Julia Coronella, Vincent Blot, Marco Gymnopoulos, Anjuli Timmer, Ryo Fujita and Roland Newman as an inventors, which claims the benefit of U.S. Provisional Patent Application No. 62/401,428, filed on Sep. 29, 2016, entitled CMET MONOCLONAL BINDING AGENTS, DRUG CONJUGATES THEREOF AND USES THEREOF, naming Julia Coronella, Vincent Blot, Marco Gymnopoulos, Anjuli Timmer, Ryo Fujita and Roland Newman as an inventors, and designated by attorney docket no. 057774-0445245. The entire content of the foregoing patent applications is hereby incorporated by reference, including all text, tables and drawings.

SEQUENCE LISTING

The present application is being filed with a Sequence Listing. The Sequence Listing is submitted electronically in ASCII format via EFS-Web in the form of a text file. Said ASCII copy, created on Mar. 12, 2021, is named 057774-0503143_SL.txt and is 105,451 bytes in size, the contents of which are incorporated herein by reference in their entirety.

TECHNICAL FIELD

Embodiments of the invention relate to compositions comprising binding agents that specifically bind to cMET, and uses thereof.

BACKGROUND ART

The protein cMET, sometimes called MET or hepatocyte growth factor receptor (HGFR), is a protein that in humans is encoded by the MET gene (MET proto-oncogene, receptor tyrosine kinase). cMET is a single-pass cell surface receptor that possesses tyrosine kinase activity. The primary single chain precursor protein of the MET translation product is post-translationally cleaved to produce an alpha and a beta subunit, which are disulfide linked to form a mature cell surface cMET receptor. cMET is expressed on cells of epithelial origin, as well as stem cells, progenitor cells and other cell types. Hepatocyte growth factor/Scatter Factor (HGF/SF) and its splicing isoforms (NK1, NK2) have been identified as ligands of cMET.

cMET is thought to be essential for normal embryonic development, organogenesis and wound healing. Abnormal cMET expression and/or activity is associated with certain neoplastic disorders and cancers (e.g., cancers of kidney, liver, stomach, breast, and brain) where cMET is implicated in tumor growth, angiogenesis, and metastasis. The overexpression of cMET as well as its autocrine activation by co-expression of its ligand are also implicated in oncogenesis.

SUMMARY OF INVENTION

Presented herein are novel binding agents, monoclonal antibodies and binding portions thereof, that bind specifically to cMET, pharmaceutical compositions thereof and methods of using the same.

In some aspects, presented herein is a binding agent that specifically binds to cMET, an extracellular domain of cMET or a portion thereof. In some embodiments a binding agent described herein binds specifically to a protein or polypeptide that comprises cMET, an extracellular domain of cMET or a portion thereof. In certain embodiments, a binding agent binds specifically to one or more mammalian cMETs selected from a human cMET, non-human primate cMET (e.g., a monkey cMET), a rat cMET, and a mouse cMET. In certain embodiments, a binding agent specifically binds to a variant of human cMET and/or to an extracellular domain of a human cMET comprising one or more naturally occurring variants. In certain embodiments, a binding agent specifically binds to a human cMET variant comprising an E168D and/or an N375S variant.

In some aspects, a binding agent that specifically binds to cMET comprises a CDR-L1, a CDR-L2 and/or a CDR-L3 which are three polypeptide sequences of a light chain complementarity determining region (CDR-L), where the CDR-L1 is selected from Table 1, the CDR-L2 is selected from Table 2 and the CDR-L3 is selected from Table 3. In some aspects, a binding agent that specifically binds to cMET comprises a CDR-H1, a CDR-H2 and/or a CDR-H3 which are three polypeptide sequences of a heavy chain complementarity determining region (CDR-H), where the CDR-H1 is selected from Table 6, the CDR-H2 is selected from Table 7 and the CDR-H3 is selected from Table 8. In some aspects, a binding agent that specifically binds to cMET comprises a CDR-L1 selected from Table 1, a CDR-L2 selected from Table 2, a CDR-L3 selected from Table 3, a CDR-H1 selected from Table 6, a CDR-H2 selected from Table 7, and a CDR-H3 selected from Table 8. In some embodiments, a CDR-L1 is selected from SEQ ID NOs 2, 4, 6, 8, 10, 12 and 14. In some embodiments, a CDR-L2 is selected from SEQ ID NOs 17, 19, 21, 23 and 25. In some embodiments, a CDR-L3 is selected from SEQ ID NOs 27, 29, 31, 33 and 35. In some embodiments, a CDR-H1 is selected from SEQ ID NOs 51, 53, 55, 57 and 59. In some embodiments, a CDR-H2 selected from SEQ ID NOs 63, 65, 67, 69, 73 and 75. In some embodiments, a CDR-H3 is selected from Table 8 is selected from SEQ ID NOs 80, 82, 84, 86, 88, 91 and 93. In some embodiments, the binding agent is an antibody, or a cMET binding fragment thereof.

In certain embodiments a binding agent comprises a variable light chain region having an amino acid sequence selected from Table 4 or 5, and/or a variable heavy chain region having an amino acid sequence selected from Table 9 or 10. A variable light chain of Table 4 or 5, or a variable heavy chain of Table 9 or 10, may comprise one to twenty, or in some embodiments, one to ten amino acid modifications selected from an amino acid addition, an amino acid deletion and an amino acid substitution, where the binding agent retains specific binding to cMET.

In certain embodiments, a binding agent is a monoclonal antibody, or cMET binding fragment thereof. In some embodiments, the binding agent comprises a constant region of an IgG1, IgG2, IgG3, or IgG4. In some embodiments, the binding agent comprises a constant region of an IgD, IgE, IgA or IgM. In certain embodiments a binding agent is humanized and/or comprises at least one to four humanized or human framework regions. In certain embodiments, a binding agent comprises at least one to four mouse framework regions. In some embodiments, a binding agent is a Fab, Fab', F(ab')2, Fv or scFV fragment of an antibody.

In some aspects a binding agent described herein has one or more functional properties. In certain embodiments, a binding agent induces or promotes internalization of cMET on a human cancer cell. In some embodiments, a binding agent induces or promotes degradation of cMET on a human cancer cell. In some embodiments, a binding agent does not have detectable cMET agonist activity. In some embodiments, a binding agent induces or promotes death of a cell to which it binds. In certain embodiments a binding agent is conjugated to an anti-neoplastic agent.

In some aspects, a binding agent described herein specifically binds to cMET, or a portion thereof. In some aspects, a binding agent described herein specifically binds to cMET, or a portion thereof with a KD of 10 nM or less, or 1 nM or less. In some aspects, an affinity of a binding agent for cMET, or a portion thereof, comprises a KD of 10 nM or less, or 1 nM or less In some embodiments, a binding agent that specifically binds to cMET further comprises a second antigen binding portion that specifically binds to another antigen (e.g., an antigen that is not cMET, or a portion thereof). For example, in some embodiments, a binding agent comprises a first antigen binding domain that specifically binds to cMET and a second antigen binding domain that specifically binds to another polypeptide.

In certain aspects, presented herein are methods of treating a subject having or suspected of having a neoplastic disorder or cancer. In one embodiment, a method includes administering a therapeutically effective amount of a binding agent described herein to a subject. In some embodiments, a method comprises contacting a cell of the subject (e.g., a neoplastic or cancerous cell) with the binding agent. In certain embodiments, the binding agent is configured to specifically bind to the extracellular domain of cMET expressed on one or more cells of the subject. In certain embodiments, the binding agent decreases, inhibits or reduces mitosis of, and/or promotes or induces death of the one or more cells expressing cMET. In certain embodiments, the neoplastic disorder or cancer comprises a lung carcinoma, breast carcinoma, ovarian carcinoma, kidney carcinoma, colorectal carcinoma, gastric carcinoma, thyroid carcinoma, pancreas carcinoma, neuroblastoma, or a squamous cell carcinoma of the head and neck, cervical cancer, hepatocellular cancer, sarcomas, mesothelioma, glioblastoma, multiple myeloma, melanoma, prostate and esophageal carcinoma.

In some embodiments, a pharmaceutical composition which comprises the binding agent is provided. In some embodiments, a pharmaceutical composition comprises, in addition to the binding agent, a pharmaceutically acceptable excipient, diluent, additive and/or carrier. In some embodiments, a pharmaceutical composition is formulated as a sterile, lyophilized powder, that upon reconstitution, is suitable for intravenous administration to a mammal.

Certain aspects of the technology are described further in the following description, examples, claims and drawings.

The drawings illustrate embodiments of the technology and are not limiting. For clarity and ease of illustration, the drawings are not made to scale and, in some instances, various aspects may be shown exaggerated or enlarged to facilitate an understanding of particular embodiments.

BRIEF DESCRIPTION OF DRAWINGS

FIG. 4 shows characterization results from an exemplary fusion (FUSION 6B1, plate 3). Anti-cMet hybridomas were selected, in part, for the presence of specific binding to cMet as assayed by ELISA (see column labeled "MET Binding ELISA OD450 nm") and for ability to induce internalization of cMET on human cancer cell lines as measured by flow cytometry (see column labeled "FACS Geom. Mean"). A FACS Geo Mean value lower than a negative control indicates internalization of cMet. The arrow indicates a lead hybridoma F6B1P3D12.

FIG. 8A shows an alignment of the amino acid sequences of the light chain variable regions of nine mouse monoclonal anti-cMET antibodies, the names of which are indicated to the left of each sequence. SEQ ID NOs are indicated to the right of each sequence. Amino acid sequences of the light chain variable regions of LC F6B1P1E2 and F6BP3E2 are 100% identical. Also, amino acid sequences of the light chain variable regions of LC F6B1P3D12 and F6B1P3E9 are 100% identical.

FIG. 8B shows an alignment of the amino acid sequences of the heavy chain variable regions of nine mouse monoclonal anti-cMET antibodies, the names of which are indicated to the left of each sequence. SEQ ID NOs are indicated to the right of each sequence. Amino acid sequences of the heavy chain variable regions of F6B1P3D12H7913 and F6B1P3E9 are 100% identical. Also, amino acid sequences of the heavy chain variable regions of F6B1P1E2H7819 and F6BP3E2 are 100% identical.

FIG. 13 shows an alignment of five humanized light chain variable regions of humanized versions of the murine anti-cMET clone P3D12, the names and SEQ ID NOs of which are indicated to the left of each sequence. Five independent methods were used to humanize the murine anti-cMET mAbs. Two of the methods gave the same result, therefore there are 4 different light chains shown.

FIG. 14 shows an alignment of five humanized heavy chain variable regions of humanized versions of the murine clone P3D12, the names and SEQ ID NOs of which are indicated to the left of each sequence. Five independent methods were used to humanize the murine anti-cMET mAb. Two of the methods gave the same result, therefore there are 4 different light chains (see FIG. 13) and 4 different heavy chains which can make a combination of 16 different binding agents.

DESCRIPTION OF EMBODIMENTS

Figure 1:
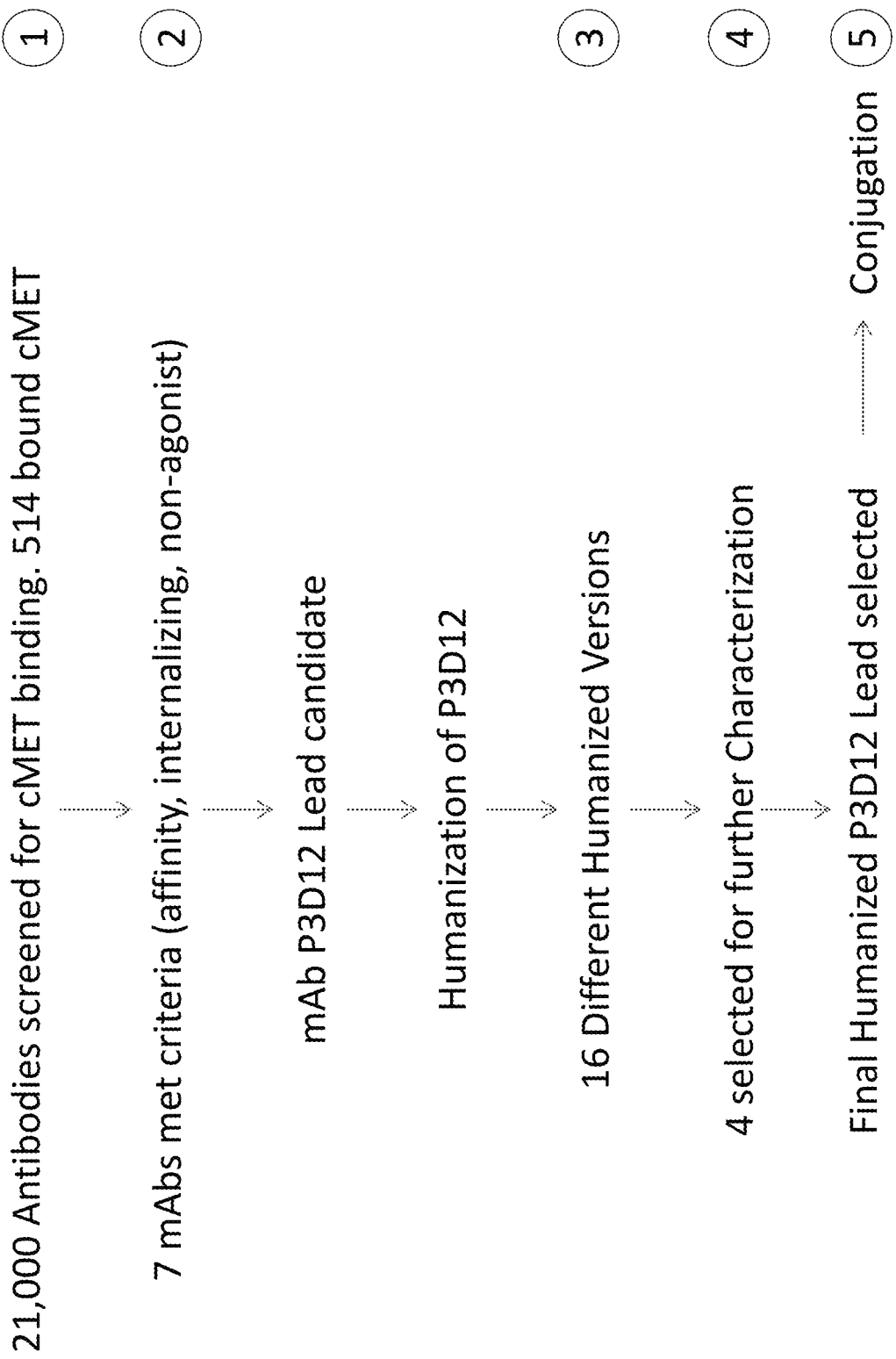
FIG. 1 shows a summary of the work flow used for generation of monoclonal antibodies (exemplary binding agents) that bind specifically to cMET. The lead monoclonal Ab P3D12 was generated from a mouse immunized with recombinant intact extracellular domain of cMET fused to human Fc.

Presented herein, in some embodiments, are monoclonal binding agents that bind cMET, or a portion thereof, as well as compositions and uses thereof. The proto-oncogene MET translation product comprises the mesenchymal epithelial transition factor (MET). MET is used synonymously herein with the term "cMET". cMET is also known as hepatocyte growth factor receptor (HGFR). Human cMET (e.g., SEQ ID NO: 109) comprises an immature polypeptide sequence of 1390 amino acids and includes an N-terminal single sequence from amino acids 1-24, an extracellular domain of human cMET from about amino acid 24-932, a transmembrane domain from about amino acid 933 to 955 and a cytoplasmic domain at about amino acid 956 to 1390, numbered from the N-terminus to the C-terminus. Methods of identifying leader sequences, extracellular domains, transmembrane domains, and cytoplasmic domains of a cMET receptor are known and any suitable method can be used to identify such domains or regions within a cMET polypeptide sequence derived from a suitable mammalian species. A human cMET polypeptide may comprise several known variants (e.g., see URL:http://www.uniprot.org/uniprot/P08581, as accessed on May 5, 2016, which cMET variants and alternative sequences disclosed therein are incorporated herein by reference). Non-limiting examples of naturally occurring variants of a human cMET include amino acid substitutions at 143, 150, 156, 168, 238, 316, 320, 375, 385, 773, 970, 991, and/or 992 of human cMET (SEQ ID NO: 109). In some embodiments cMET or a cMET extracellular domain comprises an E to D substitution at position 168 of human cMET, referred to herein as E168D. In some embodiments cMET or a cMET extracellular domain comprises an N to S substitution at position 375 of human cMET, referred to herein as N375S.

In some embodiments cMET is a mammalian cMET. In some embodiments cMET is a primate cMET. In some embodiments cMET is a human cMET. In some embodiments cMET is a monkey cMET. In some embodiments cMET is a rodent cMET (e.g., rat and/or mouse). In some embodiments cMET is a canine cMET (e.g., a dog cMET). Non-limiting examples of a mammalian cMET are provided in Example 5 and/or in a sequence listing of this application. In certain embodiments, an extracellular domain of cMET comprises an N-terminal portion of a cMET polypeptide that is typically expressed on the cell surface of an intact mammalian cell. An extracellular domain of cMET may comprise two or more polypeptide chains derived from a MET translation product. In certain embodiments an extracellular domain of cMET can be expressed in a soluble and/or a non-membrane bound form that lacks a cytoplasmic and/or transmembrane domain. In certain embodiments an extracellular domain of cMET is expressed, isolated and/or purified as a fusion protein. For example, the extracellular domain of a mammalian cMET can be engineered and expressed as a fusion protein comprising an Fc portion of an immunoglobulin (e.g., cMET-Fc). In certain embodiments cMET and/or the extracellular domain of cMET comprises one or more amino acid additions, deletions or substitutions. A cMET polypeptide may be at least 80%, at least 85%, at least 90% or at least 95% to a cMET polypeptide disclosed herein. In certain embodiments, a cMET polypeptide comprises a portion of (e.g., a sub-sequence of) a cMET protein. In some embodiments a portion of a cMET comprises an extracellular domain of cMET, or a portion thereof.

Presented herein, in some embodiments, are compositions (e.g., pharmaceutical compositions) comprising one or more binding agents that bind specifically to cMET or a portion thereof. In some embodiments a binding agent presented herein is used for the treatment, prevention and/or diagnosis of a neoplastic disorder and/or a cancer in a subject.

The term "subject" refers to a mammal. Any suitable mammal can be treated by a method or composition described herein. Non-limiting examples of mammals include humans, non-human primates (e.g., apes, gibbons, chimpanzees, orangutans, monkeys, macaques, and the like), domestic animals (e.g., dogs and cats), farm animals (e.g., horses, cows, goats, sheep, pigs) and experimental animals (e.g., mouse, rat, rabbit, guinea pig). In some embodiments a mammal is a human. A mammal can be any age or at any stage of development (e.g., an adult, teen, child, infant, or a mammal in utero). A mammal can be male or female. A mammal can be a pregnant female.

In some embodiments a subject is in need of a treatment or composition described herein. In certain embodiments a subject has or is suspected of having a neoplastic disorder or a cancer. In some embodiments a subject in need of a treatment or composition described herein has or is suspected of having a neoplastic disorder or a cancer. In certain embodiments a binding agent or composition described herein is used to treat a subject having, or suspected of having, a neoplastic disorder or cancer.

In certain embodiments, a binding agent comprises or consists of one or more polypeptides or one or more proteins that bind specifically to at least one antigen (e.g., cMET or a portion thereof). A binding agent often comprises at least one antigen binding portion (i.e. a binding portion). An antigen binding portion of a binding agent is that portion that binds specifically to an antigen. In certain embodiments a binding portion of a binding agent comprises or consists of a single polypeptide (e.g., single chain antibody). In some embodiments a binding portion of a binding agent comprises or consists of two polypeptides. In some embodiments a binding portion of a binding agent comprises or consists of 2, 3, 4 or more polypeptides. In some embodiments a binding agent comprises one or more structural portions (e.g., scaffolds, structural polypeptides, constant regions and/or framework regions). In some embodiments a binding agent, or binding portion thereof is attached to a substrate (e.g., a polymer, a non-organic material, silicon, a bead, and the like).

A binding agent may comprise one antigen binding portion or multiple antigen binding portions. For example, a binding agent that comprises one binding portion is sometimes referred to as monovalent. A binding agent that comprises two binding portions is sometimes referred as divalent. In some embodiments a binding agent comprises 1, 2, 3, 4, 5, 6, 7, 8, 9, or 10 or more binding portions. In certain embodiments, all of the binding portions of a multivalent binding agent bind to the same antigen. In certain embodiments, all of the binding portions of a multivalent binding agent comprise one or more polypeptide sequences that are at least 90%, at least 95%, at least 99% or 100% identical.

In certain embodiments, two or more binding portions of a binding agent bind to different antigens. Such binding agents are sometimes referred to as bi-specific or multi-specific binding agents (e.g., antibodies). Thus, in certain embodiments a binding agent comprises a first antigen binding portion that specifically binds cMET, or a portion thereof, and a second antigen binding portion that specifically binds another antigen (e.g., a polypeptide that is not cMET, or a portion thereof). A binding agent that specifically binds cMET, in some embodiments, is covalently or non-covalently attached to another binding agent that does not bind specifically to cMET, or a portion thereof. In certain embodiments, a binding agent that specifically binds cMET comprises a second binding agent the specifically binds to another antigen.

In some embodiments a binding agent comprises an antibody, or a portion thereof (e.g., a binding portion thereof). In certain embodiments, a binding agent comprises or consists of a suitable antibody, an antibody fragment and/or an antigen binding portion of an antibody (e.g., a binding fragment, i.e., a binding portion thereof). In some embodiments a binding agent is an antibody (e.g., a monoclonal antibody and/or a recombinant antibody). A binding agent or antibody can be generated, manufactured or produced by a suitable method. In some embodiments a binding agent is monoclonal. In some embodiments a binding agent is a monoclonal antibody derived from a suitable species. Certain non-limiting examples of a binding agent include monoclonal antibodies, chimeric antibodies, antibody binding fragments (e.g., an antigen binding portion of an antibody), a CDR-grafted antibody, a humanized antibody, a human antibody, or portions thereof. Human antibodies can be obtained by any suitable method. For example, human antibodies can be obtained from trans-chromosomal animals engineered to produce fully human antibodies. In certain embodiments, a binding agent is not polyclonal, is not a polyclonal antibody and the term "binding agent" does not refer to polyclonal antibodies.

In some embodiments a binding agent is derived, produced, obtained, isolated, and/or purified from a suitable species. In some embodiments a binding agent is derived, produced, obtained, isolated, and/or purified from a rabbit, goat, horse, cow, rat, mouse, fish, bird, or llama, for example. In some embodiments a binding agent is derived, produced, obtained, isolated, and/or purified from a bird (e.g., a chicken, or a bird egg). In some embodiments a binding agent is derived, produced, obtained, isolated, and/or purified from a plant (e.g., a recombinant binding agent produced by a genetically engineered plant). In some embodiments a binding agent is derived, produced, obtained, isolated, and/or purified from a suitable mammal. In certain embodiments a suitable mammal is a genetically altered mammal (e.g., a trans-chromosomal or transgenic mammal) engineered to produce antibodies comprising human heavy chains and/or human light chains or portions thereof. In some embodiments a binding agent is produced, obtained, isolated, or purified from a prokaryotic or eukaryotic cell (e.g., a recombinant binding agent produced by a genetically engineered cell). In some embodiments a binding agent is produced, obtained, isolated, or purified from a virus (e.g., a recombinant binding agent produced by a genetically engineered virus). A binding agent can be expressed, isolated from and/or purified from a suitable expression system non-limiting examples of which include a suitable bacteria, phage, insect, virus, plant or mammalian expression system. For example, a nucleic acid encoding a binding agent can be introduced into a suitable mammalian cell line that expresses and secretes the binding agent into the cell culture media.

In certain embodiments, a binding agent is not found in nature and is not naturally occurring. For example, in certain embodiments, a binding agent is generated artificially in an animal by administering an emulsified cocktail that includes a foreign recombinant antigen, a powerful adjuvant, and often a mineral oil and/or a detergent, thereby inducing an artificial immune response to the foreign recombinant antigen (e.g., cMET, cMET-Fc).

In certain embodiments, a monoclonal antibody or a monoclonal binding agent is a substantially homogeneous population of binding agents, or binding fragments thereof, where each individual binding agent in the population is substantially identical and/or binds to the same epitope, with the exception of possible variants that may arise during production of a monoclonal binding agent. In some embodiments such variants generally are absent or may be present in minor amounts. In contrast to polyclonal antibody preparations which typically include a population of different antibodies directed against different determinants (epitopes), each binding agent of a population of monoclonal binding agents often binds to a single determinant of an antigen. Monoclonal binding agents are often not contaminated by other immunoglobulins. One or more different monoclonal binding agents may be purposely added to a composition to form a mixture.

The modifier "monoclonal" is not to be construed as requiring production of a binding agent by any particular method. A monoclonal binding agent can be produced by any suitable method. For example, in certain embodiments, a monoclonal antibody is made by the hybridoma method (e.g., as described by Kohler et al, Nature, 256:495 (1975)), or a variation thereof. In some embodiments a monoclonal binding agent is made by a recombinant DNA method. For example, a monoclonal binding agent can be made by screening a recombinant library using a suitable expression system (e.g., a phage display expression system). In some embodiments a monoclonal binding agent is isolated from a phage library of binding agents, for example by using a technique described in Clackson et al, Nature, 352:624-628 (1991) and/or Marks et al, J. Mol Biol, 222:581-597 (1991), or a variation thereof.

In certain embodiments, a binding agent comprises one or more structural or backbone portions, sometimes referred to as scaffolds. A binding agent may comprise a scaffold, non-limiting examples of which include a scaffold derived from an antibody, a Z domain of Protein A, gamma-B crystalline, ubiquitin, cystatin, Sac7d, a triple helix coiled coil, a lipocalin, an ankyrin repeat motif, an SH3 domain of Fyn, a Kunitz domain of a suitable protease inhibitor, a fibronectin domain, a nucleic acid polymer, and the like, portions thereof or combinations thereof. In some embodiments a binding agent does not comprise a scaffold. In certain embodiments, a binding agent comprises one or more structural portions of a mammalian antibody.

In certain embodiments a binding agent comprises one or more constant regions (e.g., constant regions derived from an antibody, e.g., a mammalian antibody). In certain embodiments a binding agent comprises a constant region of an antibody light chain and/or a constant region of an antibody heavy chain. In a mammalian antibody at least two types of immunoglobulin light chains exist which are referred to as lambda (l) and kappa (κ). A binding agent may comprise any suitable constant region of an antibody, or one or more portions thereof. In some embodiments a binding agent comprises a lambda light chain constant region or a portion thereof. In some embodiments a binding agent comprises a kappa light chain constant region or a portion thereof. In some embodiments a binding agent comprises a polypeptide that is at least 75%, at least 80%, at least 85%, at least 90%, at least 95% or at least 99% identical to a polypeptide sequence of a constant region, or portion thereof, of a light chain of a mammalian antibody. In some embodiments a binding agent comprises a polypeptide that is at least 75%, at least 80%, at least 85%, at least 90%, at least 95% or at least 99% identical to a polypeptide sequence of a constant region of an antibody light chain of a human antibody. In some embodiments a binding agent does not include a light chain constant region.

In certain embodiments a binding agent comprises a constant region of an antibody heavy chain. In mammals, an antibody can have at least five types/classes of Ig heavy chains denoted as IgA, IgD, IgE, IgG, and IgM, which are determined by the presence of distinct heavy chain constant regions, or portion thereof (e.g., CH1, CL, CH2, CH3 domains). A binding agent can include any suitable heavy chain constant region, or portion thereof. In some embodiments a binding agent comprises a heavy chain constant region of an IgG1, IgG2, IgG3 or IgG4, or one or more portions thereof. In some embodiments a binding agent comprises one or more heavy chain constant regions of an IgM, IgD, IgA, or IgE isotype, or a portion thereof. In some embodiments a binding agent comprises a polypeptide that is at least 75%, at least 80%, at least 85%, at least 90%, at least 95%, at least 99% identical, or 100% identical to a polypeptide sequence of a constant region, or portion thereof, of a heavy chain of a mammalian antibody. In some embodiments a binding agent comprises a polypeptide that is at least 75%, at least 80%, at least 85%, at least 90%, at least 95%, at least 99% identical or 100% identical to a polypeptide sequence of a constant region of an antibody heavy chain of a human antibody. In some embodiments a binding agent comprises one or more additions, deletions and/or modification to a constant region. A binding agent is sometimes modified to change the antibody class, or isotype of a binding agent. In some embodiments a binding agent comprises one or more additions, deletions and/or modification (one or more amino acid substitutions, deletions or additions) to modify one or more functions of a binding agent, for example to abolish, enhance or decrease serum half-life, Fc receptor binding, complement binding (e.g., C1q binding), glycosylation, sialylation, cellular toxicity, antibody-dependent cell-mediated phagocytosis (ADCP), antibody dependent cellular cytotoxicity (ADCC), and the like. In some embodiments a binding agent does not include one or more portions of a heavy chain constant region or light chain constant region. In some embodiments a binding agent does not include a heavy chain constant region.

In some embodiments a binding agent comprises or consists of one or more variable regions of an antibody, or a portion thereof. In some embodiments a binding agent comprises one or more light chain variable regions, or a portion thereof. In some embodiments a binding agent comprises one or more heavy chain variable regions, or a portion thereof. In certain embodiments a binding agent comprises at least one light chain variable region and at least one heavy chain variable region. A light chain variable region and heavy chain variable region can be on the same or different polypeptides. In certain embodiments, an antigen binding portion of a binding agent consists of one or more heavy chain variable regions. In certain embodiments, an antigen binding portion of a binding agent consists of one or more light chain variable regions. In certain embodiments, an antigen binding portion of a binding agent consists of one or more light chain variable regions and one or more heavy chain variable regions.

In some embodiments a binding agent comprises or consists of a Fab, Fab', F(ab')2, Fv fragment, single-chain Fv (scFv), diabody (Dab), synbody, the like and/or a combination or portion thereof. In some embodiments a binding agent is a Fab, Fab', F(ab')2, Fv fragment, single-chain Fv (scFv), diabody (Dab), synbody, the like and/or a combination, or portion thereof (see, e.g., U.S. Pat. Nos. 6,099,842 and 5,990,296). In some embodiments a binding agent comprises a single-chain polypeptide comprising one or more antigen binding portions. For example, a single-chain binding agent can be constructed by joining a heavy chain variable region, or antigen binding portion thereof, with a light chain variable region, or antigen binding portion thereof, with a linker (e.g., an amino acid, a polypeptide linker) using recombinant molecular biology processes. Such single chain binding agents often exhibit specificities and affinities for an antigen similar to a parent two-chain monoclonal binding agent. Binding agents often comprise engineered regions such as CDR-grafted or humanized portions. In certain embodiments a binding agent is an intact two-chain immunoglobulin, and in other embodiments a binding agent is a Fab monomer or a Fab dimer.

Nucleic acids, or portions thereof, that encode a polypeptide of a binding agent may be cloned, subcloned, rearranged or modified for recombinant expression by a suitable cloning procedure and subsequently expressed using a suitable expression system by a method known to those skilled in the art (e.g., see Maniatis et al., Molecular Cloning: A Laboratory Manual, Cold Spring Harbor Laboratory, 1982; Antibody Engineering: Methods and Protocols, Vol. 248 of Methods in molecular biology, edited by Benny K. C. Lo, Springer Science & Business Media, 2004; Antibody Engineering, Vol. 1, Roland E. Kontermann, Stefan Duebel, Edition 2, Publisher Springer Science & Business Media, 2010; Antibody Phage Display: Methods and Protocols, Biomed Protocols, Vol. 178 of Methods in molecular biology, Editors Philippa M. O'Brien, Robert Aitken, Springer Science & Business Media, 2004).

In mammals, the heavy chain variable region and light chain variable region of an antibody each contribute three CDRs (complementarity determining regions) commonly referred to as CDR1, CDR2 and CDR3, that are separated and/or flanked by framework regions (e.g., FR1, FR2, FR3 and FR4). The term "CDR" as used herein refers to an amino acid sequence of a polypeptide identified as a complementarity determining region. In certain embodiments, definitive delineation of a CDR polypeptide sequence and identification of residues comprising the binding site of a binding agent is accomplished by solving the structure of a binding agent and/or solving the structure of a binding agent-antigen complex. In certain embodiments, this can be accomplished by any suitable method, such as X-ray crystallography and/or computer modeling. In certain embodiments, various methods of analysis can be employed to identify or approximate the CDR sequences of a binding agent or antibody. For example, the amino acid sequence and/or location of CDRs in a polypeptide sequence of a binding agent, an antibody, a binding portion thereof or variable region thereof, can be identified using a suitable method, non-limiting examples of which include the Kabat system (e.g., see Kabat, E. A., et al., 1991; Sequences of Proteins of Immunological Interest, Fifth Edition, NIH Publication No. 91-3242, as well as Johnson, G. and Wu, T. T. 2000, Nucleic Acids Research), and/or the Chothia Numbering Scheme (e.g., Chothia & Lesk, (1987) J. Mol. Biol, 196:901-917; Chothia et al, Nature, (1989) 342:878-883; and Al-Lazikani et al., (1997) JMB 273, 927-948). In some embodiments the amino sequence and/or location of CDRs of an antibody can be identified using the AbM method and/or contact method. The "AbM" definition uses an integrated suite of computer programs produced by Oxford Molecular Group that model antibody structure (see e.g., Martin et al, Proc. Natl. Acad. Sci. (USA), 86:9268-9272 (1989); "AbM™, A Computer Program for Modeling Variable Regions of Antibodies," Oxford, UK; Oxford Molecular, Ltd.). The AbM definition models the tertiary structure of an antibody from primary sequence using a combination of knowledge databases and ab initio methods, such as those described by Samudrala et al., "Ab Initio Protein Structure Prediction Using a Combined Hierarchical Approach," in PROTEINS, Structure, Function and Genetics Suppl, 3:194-198 (1999). In certain embodiments, a contact definition is based on an analysis of the available complex crystal structures (see e.g., MacCallum et ah, J. Mol. Biol, 5:732-45 (1996)).

In some embodiments a binding agent and/or an antigen binding portion of a binding agent comprises at least 2, at least 3, at least 4, at least 5 or at least 6 CDRs. In some embodiments a binding agent comprises 3 to 60 CDRs (e.g., for binding agents having multiple antigen binding portions). In some embodiments a binding agent comprises 3 to 12 CDRs. In some embodiments an antigen binding portion of a binding agent comprises 1 to 6 CDR polypeptide sequences.

In certain embodiments, a binding agent and/or an antigen binding portion of a binding agent comprises one, two or three CDRs of a light chain variable region. In some embodiments a light chain variable region of a binding agent comprises one or more CDRs (e.g., one, two, three, or more CDRs). The amino acid sequences representing a CDR in a light chain variable region of an antibody or binding agent is referred to as CDR-L1, CDR-L2, and CDR-L3 which are numbered sequentially (i.e., L1, L2 and L3) in the direction from the amino terminus (N-terminus) to the carboxy terminus (C-terminus) of a light chain variable region. For example, in a polypeptide representing a light chain variable region of a binding agent, CDR-L1, when present, is the most N-terminal light chain CDR; CDR-L3, when present, is the most C-terminal light chain CDR; and CDR-L2, when present, is located (i) between CDR-L1 and CDR-L3, (ii) on the N-terminal side of CDR-L3 or (iii) on the C-terminal side of CDR-L1, of a light chain variable region or binding portion of a binding agent. The terms "CDR-L1", "CDR-L2" and "CDR-L3" refer to, in part, an amino acid sequence of a polypeptide identified as, or disclosed herein as, a complementarity determining region of a binding agent (e.g., a CDR of a light chain variable region). Non-limiting examples of amino acid sequences of a CDR-L1, CDR-L2 and CDR-L3 are provided in Tables 1-3, respectively. A light chain variable region or antigen binding portion of a binding agent described herein may comprise any combination of a CDR-L1, a CDR-L2, and a CDR-L3 disclosed herein, wherein the binding agent retains specific binding to cMET, or a portion thereof. In certain embodiments, a light chain variable region or antigen binding portion of a binding agent described herein comprises a single light chain CDR comprising an amino acid sequence at least 70% identical to a CDR-L3 selected from Table 3. In certain embodiments, a light chain variable region or antigen binding portion of a binding agent described herein comprises an amino acid sequence at least 70% identical to a CDR-L3 selected from Table 3, and any other suitable CDR-L2 and/or CDR-L1 polypeptide sequence, where the binding agent retains specific binding to cMET, or a portion thereof. In certain embodiments, the light chain CDRs of a light chain variable region or antigen binding portion of a binding agent consists of a CDR-L3 and a CDR-L2, where the CDR-L3 comprises an amino acid sequence at least 70% identical to a CDR-L3 selected from Table 3 and the CDR-L2 comprises an amino acid sequence at least 70% identical to a CDR-L2 selected from Table 2. In certain embodiments, a light chain variable region or antigen binding portion of a binding agent described herein comprises an amino acid sequence at least 70% identical to a CDR-L3 selected from Table 3 and an amino acid sequence at least 70% identical to a CDR-L2 selected from Table 2, and any other suitable CDR-L1 polypeptide sequence, where the binding agent retains specific binding to cMET, or a portion thereof. In certain embodiments, a light chain variable region or antigen binding portion of a binding agent described herein comprises three light chain CDRs consisting of an amino acid sequence at least 70% identical to a CDR-L3 selected from Table 3, an amino acid sequence at least 70% identical to a CDR-L2 selected from Table 2 and an amino acid sequence selected at least 70% identical to a CDR-L1 of Table 1. In certain embodiments, a light chain variable region or antigen binding portion of a binding agent described herein comprises an amino acid sequence at least 70% identical to a CDR-L3 selected from Table 3, an amino acid sequence at least 70% identical to a CDR-L2 selected from Table 2 and an amino acid sequence at least 70% identical to a CDR-L1 selected from Table 1, where the binding agent retains specific binding to cMET, or a portion thereof.

In some embodiments a binding agent comprises one or more light chain CDRs that are at least 70%, 75%, 85%, 86%, 87%, 88%, 89%, 90%, 91%, 92%, 93%, 94%, 95%, 96%, 97%, 98%, or at least 99% identical to any one of the CDR sequences listed in Tables 1, 2 or 3. In some embodiments a binding agent or the antigen binding portion of a binding agent comprises a CDR-L1 that is at least 70%, 75%, 85%, 86%, 87%, 88%, 89%, 90%, 91%, 92%, 93%, 94%, 95%, 96%, 97%, 98%, or at least 99% identical to any one of the sequences shown in Table 1. In some embodiments a binding agent or the antigen binding portion of a binding agent comprises a CDR-L1 of any one of the sequences shown in Table 1.

TABLE 1

CDR-L1 Sequences

| ID | Clone | Amino Acid Sequence |
|---|---|---|
| SEQ ID NO: 1 | F5_P5_B9_L | RSSQTIVHGTGNTYLE |
| SEQ ID NO: 2 | F5_P5_B9_L | QTIVHGTGNTY |
| SEQ ID NO: 3 | F6A_P8_E2_L | KASENVGTYVS |
| SEQ ID NO: 4 | F6A_P8_E2_L | ENVGTY |
| SEQ ID NO: 5 | F6AP12F12_L | RSSQSLLYSINQKNYLA |
| SEQ ID NO: 6 | F6AP12F12_L | QSLLYSINQKNY |
| SEQ ID NO: 7 | F6B_P1_H5_L | RASENIYNTLA |
| SEQ ID NO: 8 | F6B_P1_H5_L | ENIYNT |
| SEQ ID NO: 9 | F6B1_P3_D12_L/ F6B1_P3_E9_L | SASSSVTSNYLY |
| SEQ ID NO: 10 | F6B1_P3_D12_L/ F6B1_P3_E9_L | SSVTSNY |
| SEQ ID NO: 11 | F6B_P2_D4_L/ F6B1_P1_E2_L/ F6B_P3_E2_L | SASSSVSSNYLY |
| SEQ ID NO: 12 | F6B_P2_D4_L/ F6B1_P1_E2_L/ F6B_P3_E2_L | SSVSSNY |
| SEQ ID NO: 13 | Consensus | SASSSV(S/T)SNYLY |
| SEQ ID NO: 14 | P3D12 VL-abb/ sdr | QSVTSNY |
| SEQ ID NO: 15 | P3D12 VL-abb/ sdr | RASQSVTSNYLY |

Clone names referenced in Tables 1-10 indicate the Fusion number ("F"), Plate number ("P") and well number (A1 to H12) of a 96-well plate from which the clone was derived. Accordingly, clone F6AP12F12 was derived from Fusion 6A, Plate 12, Well F12, for example. Fusion numbers of each clone correspond to the Fusions indicated in FIG. 2.

In some embodiments a binding agent or the antigen binding portion of a binding agent comprises a CDR-L2 that is at least 70%, 75%, 85%, 86%, 87%, 88%, 89%, 90%, 91%, 92%, 93%, 94%, 95%, 96%, 97%, 98%, or at least 99% identical to any one of the sequences shown in Table 2. In some embodiments a binding agent or the antigen binding portion of a binding agent comprises a CDR-L2 of any one of the sequences shown in Table 2.

TABLE 2

CDR-L2 Sequences

| ID | Clone | Amino Acid Sequence |
|---|---|---|
| SEQ ID NO: 16 | F5_P5_B9_L | KVSNRFS |
| SEQ ID NO: 17 | F5_P5_B9_L | KVS |
| SEQ ID NO: 18 | F6A_P8_E2_L | GASNRYT |
| SEQ ID NO: 19 | F6A_P8_E2_L | GAS |
| SEQ ID NO: 20 | F6AP12F12_L | WASTRES |
| SEQ ID NO: 21 | F6AP12F12_L | WAS |
| SEQ ID NO: 22 | F6B_P1_H5_L | AATNLAD |
| SEQ ID NO: 23 | F6B_P1_H5_L | AAT |

TABLE 2-continued

CDR-L2 Sequences

| ID | Clone | Amino Acid Sequence |
|---|---|---|
| SEQ ID NO: 24 | F6B1_P3_D12_L/ F6B1_P3_E9_L/ F6B_P2_D4_L/ F6B1_P1_E2_L/ F6B_P3_E2_L | STSNLAS |
| SEQ ID NO: 25 | F6B1_P3_D12_L/ F6B1_P3_E9_L/ F6B_P2_D4_L/ F6B1_P1_E2_L/ F6B_P3_E2_L | STS |

In some embodiments a binding agent or the antigen binding portion of a binding agent comprises a CDR-L3 that is at least 70%, 75%, 85%, 86%, 87%, 88%, 89%, 90%, 91%, 92%, 93%, 94%, 95%, 96%, 97%, 98%, or at least 99% identical to any one of the sequences shown in Table 3. In some embodiments a binding agent or the antigen binding portion of a binding agent comprises a CDR-L3 of any one of the sequences shown in Table 3.

TABLE 3

CDR-L3 Sequences

| ID | Clone | Amino Acid Sequence |
|---|---|---|
| SEQ ID NO: 26 | F5_P5_B9_L | FQGSHVPYTFGGGTKLEIKR |
| SEQ ID NO: 27 | F5_P5_B9_L | FQGSHVPYT |
| SEQ ID NO: 28 | F6A_P8_E2_L | GQSYSYPLTFGAGTKLELKR |
| SEQ ID NO: 29 | F6A_P8_E2_L | GQSYSYPLT |
| SEQ ID NO: 30 | F6AP12F12_L | QQYYTYPLTFGAGTKLELK |
| SEQ ID NO: 31 | F6AP12F12_L | QQYYTYPLT |
| SEQ ID NO: 32 | | QHFWGTPYTFGGGTKLEIK |
| SEQ ID NO: 33 | | QHFWGTPYT |
| SEQ ID NO: 34 | F6B_P1_H5_L/ F6B1_P3_D12_L/ F6B1_P3_E9_L/ F6B_P2_D4_L/ F6B1_P1_E2_L/ F6B_P3_E2_L | HQWSSYPPTFGSGTKLEIK |
| SEQ ID NO: 35 | F6B_P1_H5_L/ F6B1_P3_D12_L/ F6B1_P3_E9_L/ F6B_P2_D4_L/ F6B1_P1_E2_L/ F6B_P3_E2_L | HQWSSYPPT |
| SEQ ID NO: 36 | Consensus | $(X_1)Q(X_2)(X_3)(X_4)YP(X_5)T$ where $X_1$ is H, Q, or G; $X_2$ is W, S or Y; $X_3$ is S or Y; $X_4$ is S or T; and $X_5$ is P or L. |

In some embodiments a binding agent or the antigen binding portion of a binding agent comprises a light chain variable region having at least 70%, 75%, 85%, 86%, 87%, 88%, 89%, 90%, 91%, 92%, 93%, 94%, 95%, 96%, 97%, 98%, or at least 99% identity to an amino acid sequence of Table 4. In some embodiments a binding agent or the antigen binding portion of a binding agent comprises a light chain variable region sequence of Table 4.

TABLE 4

VARIABLE LIGHT CHAIN SEQUENCES

| ID | Clone | Amino Acid Sequence |
|---|---|---|
| SEQ ID NO: 37 | F5_P5_B9_L | DVLMTQTPLSLPVSLGDQASISCRSSQTIVHGTGNTYLEWYL QKPGQSPKLLIYKVSNRFSGVPDRFSGSGSGTDFTLKISRVE AEDLGVYYCFQGSHVPYTFGGGTKLEIKR |
| SEQ ID NO: 38 | F6A_P8_E2_L | DIVMTQSPKSMSMSVGERVTLSCKASENVGTYVSWYQQKP DQSPKLLIYGASNRYTGVPDRFTGSGSATDFTLTISSVQAED LADYHCGQSYSYPLTFGAGTKLELKR |
| SEQ ID NO: 39 | F6AP12F12_L | DIVMSQSPSSLAVSVGEKVTMSCRSSQSLLYSINIQKNYLAW YQQIPGQSPKLLIYWASTRESGVPDRFTGSGSGTDFTLTISRV KAEDLALYYCQQYYTYPLTFGAGTKLELKR |
| SEQ ID NO: 40 | F6B_P1_H5_L | RCDIQMTQSPASLSVSVGETVTITCRASENIYNTLAWYLQK QGKSPQLLVYAATNLADGVPSRFSGSGSGTQYSLKINSLQSE DFGSYYCQHFWGTPYTFGGGTKLEIKR |
| SEQ ID NO: 41 | F6B1_P3_D12_L & F6B1_P3_E9_L | QIVLTQSPAIMSASPGEKVTLTCSASSSVTSNYLYWYQQKPG SSPKLWIYSTSNLASGVPARFSGSGSGTSYSLTISSMEAEDA ASYFCHQWSSYPPTFGSGTKLEIKR |
| SEQ ID NO: 42 | F6B_P2_D4_L | QIVLTQSPAIMSASPGEKVTLTCSASSSVSSNYLYWYQQKPG SSPKLWIYSTSNLASGVPVRFSGSGSGTSYSLTISSMEAEDA ASYFCHQWSSYPPTFGSGTKLEIKR |
| SEQ ID NO: 43 | F6B1_P1_E2_L & F6B_P3_E2_L | QIVLTQSPAIMSASPGEKVTLTCSASSSVSSNYLYWYHQKPG SSPKLWIYSTSNLASGVPVRFSGSGSGTSYSLTISSMEAEDA ASYFCHQWSSYPPTFGSGTKLEIKR |
| SEQ ID NO: 44 | Consensus | QIVLTQSPAIMSASPGEKVTLTCSASSSVSSNYLYWY(H/Q)Q KPGSSPKLWIYSTSNLASGVP(A/R)FSGSGSGTSYSLTISSME AEDAASYFCHQWSSYPPTFGSGTKLEIKR |

In some embodiments a binding agent or the antigen binding portion of a binding agent comprises a humanized light chain variable region having at least 70%, 75%, 85%, 86%, 87%, 88%, 89%, 90%, 91%, 92%, 93%, 94%, 95%, 96%, 97%, 98%, or at least 99% identity to a sequence of Table 5. In some embodiments a binding agent or the antigen binding portion of a binding agent comprises a humanized light chain variable region sequence of Table 5.

TABLE 5

Humanized P3D12 Light Chains

| ID | Clone | Amino Acid Sequence |
|---|---|---|
| SEQ ID NO: 45 | P3D12 VL | QIVLTQSPAIMSASPGEKVTLTCSASSSVTSNYLYWYQQKPG SSPKLWIYSTSNLASGVPARFSGSGSGTSYSLTISSMEAEDAA SYFCHQWSSYPPTFGSGTKLEIKR |
| SEQ ID NO: 46 | P3D12 VL-ven | QIVLTQSPATMSASPGERVTLSCSASSSVTSNYLYWYQQKPG SSPRLWIYSTSNLASGVPARFSGSGSGTSYTLTISRMEPEDAA SYFCHQWSSYPPTFGSGTKLEIKR |
| SEQ ID NO: 47 | P3D12 VL-fra | QIVLTQSPAILSLSPGERATLSCSASSSVTSNYLYWYQQKPGS SPKLLIYSTSNLASGVPARFSGSGSGTSYTLTISSLEAEDAASY FCHQWSSYPPTFGSGTKLEIKR |
| SEQ ID NO: 48 | P3D12 VL-abb/sdr | QIVLTQSPATLSLSPGERATLSCRASQSVTSNYLYWYQQKPG SSPRLLIYSTSNLASGVPARFSGSGSGTDYTLTISRLEPEDFAS YFCHQWSSYPPTFGSGTKLEIKR |
| SEQ ID NO: 49 | P3D12 VL-cdr | QIVLTQSPATLSLSPGERATLSCSASSSVTSNYLYWYQQKPGS SPRLLIYSTSNLASGVPARFSGSGSGTSYTLTISRLEPEDFASYF CHQWSSYPPTFGSGTKLEIKR |

In certain embodiments, a binding agent and/or an antigen binding portion of a binding agent comprises one, two or three CDRs of a heavy chain variable region. In some embodiments a heavy chain variable region comprises one or more CDRs (e.g., one, two, three, or more CDRs). The amino acid sequences representing a CDR in a heavy chain variable region of an antibody or binding agent is referred to as CDR-H1, CDR-H2, and CDR-H3, which are numbered sequentially (i.e., H1, H2 and H3) in the direction from the amino terminus (N-terminus) to the carboxy terminus (C-terminus) of a heavy chain variable region. For example, in a polypeptide representing a heavy chain variable region of a binding agent, CDR-H1, when present, is the most N-terminal CDR; CDR-H3, when present, is the most C-terminal CDR; and CDR-H2, when present, is located (i) between CDR-H1 and CDR-H3, (ii) on the N-terminal side of CDR-H3 or (iii) on the C-terminal side of CDR-H, of a heavy chain variable region. The terms "CDR-H1", "CDR-H2" and "CDR-H3" refer to, in part, an amino acid sequence of a polypeptide identified as, or disclosed herein as, a complementarity determining region of a binding agent (e.g., a CDR of a heavy chain variable region of a binding agent). Non-limiting examples of amino acid sequences of a CDR-H1, CDR-H2 and CDR-H3 are provided in Tables 6-8, respectively. A heavy chain variable region or antigen binding portion of a binding agent described herein may comprise any combination of a CDR-H1, a CDR-H2, and a CDR-H3 disclosed herein where the binding agent retains specific binding to cMET, or a portion thereof. In certain embodiments, a heavy chain variable region or antigen binding portion of a binding agent described herein comprises a single heavy chain CDR consisting of an amino acid sequence at least 70% identical to a CDR-H3 selected from Table 8. In certain embodiments, a heavy chain variable region or antigen binding portion of a binding agent described herein comprises an amino acid sequence at least 70% identical to a CDR-H3 selected from Table 8, and any other suitable CDR-H2 and/or CDR-H1 polypeptide sequence, where the binding agent retains specific binding to cMET, or a portion thereof. In certain embodiments, the heavy chain CDRs of a heavy chain variable region or antigen binding portion of a binding agent consists of a CDR-H3 and a CDR-H2, where the CDR-H3 comprises an amino acid sequence at least 70% identical to a CDR-H3 selected from Table 8 and the CDR-H2 comprises an amino acid sequence at least 70% identical to a CDR-H2 selected from Table 7. In certain embodiments, a heavy chain variable region or antigen binding portion of a binding agent described herein comprises an amino acid sequence at least 70% identical to a CDR-H3 selected from Table 8 and an amino acid sequence at least 70% identical to a CDR-H2 selected from Table 7, and any other suitable CDR-H1 polypeptide sequence, where the binding agent retains specific binding to cMET or a portion thereof. In certain embodiments, a heavy chain variable region or antigen binding portion of a binding agent described herein comprises three heavy chain CDRs consisting of an amino acid sequence at least 70% identical to a CDR-H3 selected from Table 8, an amino acid sequence at least 70% identical to a CDR-H2 selected from Table 7 and an amino acid sequence selected at least 70% identical to a CDR-H1 of Table 6. In certain embodiments, a heavy chain variable region or antigen binding portion of a binding agent described herein comprises an amino acid sequence at least 70% identical to a CDR-H3 selected from Table 8, an amino acid sequence at least 70% identical to a CDR-H2 selected from Table 7 and an amino acid sequence at least 70% identical to a CDR-H1 selected from Table 6, where the binding agent retains specific binding to cMET, or a portion thereof.

In some embodiments a binding agent comprises one or more heavy chain CDRs with at least 70%, 75%, 85%, 86%, 87%, 88%, 89%, 90%, 91%, 92%, 93%, 94%, 95%, 96%, 97%, 98%, or at least 99% identity to any one of the CDRs of Tables 6, 7 or 8. In some embodiments a binding agent or the antigen binding portion of a binding agent comprises a CDR-H1 that is at least 70%, 75%, 85%, 86%, 87%, 88%, 89%, 90%, 91%, 92%, 93%, 94%, 95%, 96%, 97%, 98%, or at least 99% identical to any one of the sequences shown in Table 6. In some embodiments a binding agent or the antigen binding portion of a binding agent comprises a CDR-H1 of any one of the sequences shown in Table 6.

TABLE 6

CDR-H1 Sequences

| ID | Clone | Amino Acid Sequence |
|---|---|---|
| SEQ ID NO: 50 | F5_P5_B9_H | GFSLTNYGVN |
| SEQ ID NO: 51 | F5_P5_B9_H | GFSLTNYG |
| SEQ ID NO: 52 | F6A_P8_E2_H | GFNINDYFMH |
| SEQ ID NO: 53 | F6A_P8_E2_H | FNINDYF |
| SEQ ID NO: 54 | F6A_P12_F12_H | GFTFTDYYMS |
| SEQ ID NO: 55 | F6A_P12_F12_H | GFTFTDYY |
| SEQ ID NO: 56 | F6B_P1_H5_H | GYTFTDYNMD |
| SEQ ID NO: 57 | F6B_P1_H5_H | YTFTDYN |
| SEQ ID NO: 58 | F6B1_P3_D12_H/<br>F6B1P3E9_H/<br>F6_B1_P1_E2_H/<br>F6B_P3_E2_H/<br>F6B_P2_D4_H | GYTFTSYWMH |
| SEQ ID NO: 59 | F6B1_P3_D12_H/<br>F6B1P3E9_H/<br>F6_B1_P1_E2_H/<br>F6B_P3_E2_H/<br>F6B_P2_D4_H | YTFTSYW |
| SEQ ID NO: 60 | Consensus | GYTFT(D/S)Y(N/W) |
| SEQ ID NO: 61 | Consensus | G(Y/F)TFT(D/S)Y<br>(N/W/Y)M(H/S) |

In some embodiments a binding agent or the antigen binding portion of a binding agent comprises a CDR-H2 that is at least 70%, 75%, 85%, 86%, 87%, 88%, 89%, 90%, 91%, 92%, 93%, 94%, 95%, 96%, 97%, 98%, or at least 99% identical to any one of the sequences shown in Table 7. In some embodiments a binding agent or the antigen binding portion of a binding agent comprises a CDR-H2 of any one of the sequences shown in Table 7.

TABLE 7

CDR-H2 Sequences

| ID | Clone | Amino Acid Sequence |
|---|---|---|
| SEQ ID NO: 62 | F5_P5_B9_H | LIWGGGDTDYNSALKS |
| SEQ ID NO: 63 | F5_P5_B9_H | IWGGGDT |

TABLE 7-continued

CDR-H2 Sequences

| ID | Clone | Amino Acid Sequence |
|---|---|---|
| SEQ ID NO: 64 | F6A_P8_E2_H | WIDPENGNTIYDPKFQG |
| SEQ ID NO: 65 | F6A_P8_E2_H | IDPENGNT |
| SEQ ID NO: 66 | F6A_P12_F12_H | FIRNKANGYTTKYSASVKG |
| SEQ ID NO: 67 | F6A_P12_F12_H | IRNKANGYTT |
| SEQ ID NO: 68 | F6B_P1_H5_H | DINPNNGGTIYNQKFKG |
| SEQ ID NO: 69 | F6B_P1_H5_H | INPNNGGT |
| SEQ ID NO: 70 | F6B1_P3_D12_H/ F6B1P3E9_H | YIKPSTDNTEYNQKFKD |
| SEQ ID NO: 71 | F6B1_P3_D12_H/ F6B1P3E9_H | IKPSTDNT |
| SEQ ID NO: 72 | F6_B1_P1_E2_H/ F6B_P3_E2_H | YINPSTDYTEYNQKFKD |
| SEQ ID NO: 73 | F6_B1_P1_E2_H/ F6B_P3_E2_H | INPSTDYT |
| SEQ ID NO: 74 | F6B_P2_D4_H | YINPSTDYIEYNQKFKD |
| SEQ ID NO: 75 | F6B_P2_D4_H | INPSTDYI |
| SEQ ID NO: 76 | Consensus | INPSTDY(I/T) |
| SEQ ID NO: 77 | Consensus | (Y/D)I(K/N)PSTD(N/Y)(T/I)EY(A/N)QKF(Q/K)(G/D) |
| SEQ ID NO: 78 | P3D12 VH-abb/ sdr | YIKPSTDNTEYAQKFQG |

TABLE 8

CDR-H3 Sequences

| ID | Clone | Amino Acid Sequence |
|---|---|---|
| SEQ ID NO: 79 | F5_P5_B9_H | CARDYYGFDY |
| SEQ ID NO: 80 | F5_P5_B9_H | DYYGFDY |
| SEQ ID NO: 81 | F6A_P8_E2_H | CARGGNYLRESYYYAMDY |
| SEQ ID NO: 82 | F6A_P8_E2_H | RGGNYLRESYYYAMDY |
| SEQ ID NO: 83 | F6A_P12_F12_H | CSKDRGYFDY |
| SEQ ID NO: 84 | F6A_P12_F12_H | DRGYFDY |
| SEQ ID NO: 85 | F6B_P1_H5_H | RARGDYYGSSRYYYAMDY |
| SEQ ID NO: 86 | F6B_P1_H5_H | RGDYYGSSRYYYAMDY |
| SEQ ID NO: 87 | F6B1_P3_D12_H/ F6B1P3E9_H | CARSYGNYPLMDY |
| SEQ ID NO: 88 | F6B1_P3_D12_H/ F6B1P3E9_H & F6_B1_P1_E2_H/ F6B_P3_E2_H | SYGNYPLMDY |
| SEQ ID NO: 89 | F6_B1_P1_E2_H/ F6B_P3_E2_H | CVRSYGNYPLMDY |
| SEQ ID NO: 90 | F6B_P2_D4_H | CARSYGNFPLMDY |
| SEQ ID NO: 91 | F6B_P2_D4_H | RSYGNFPLMDY |
| SEQ ID NO: 92 | Consensus | C(A/V)RSYGN(F/Y)PLMDY |
| SEQ ID NO: 93 | Consensus | RSYGN(F/Y)PLMDY |

In some embodiments a binding agent or the antigen binding portion of a binding agent comprises a CDR-H3 that is at least 70%, 75%, 85%, 86%, 87%, 88%, 89%, 90%, 91%, 92%, 93%, 94%, 95%, 96%, 97%, 98%, or at least 99% identical to any one of the sequences shown in Table 8. In some embodiments a binding agent or the antigen binding portion of a binding agent comprises a CDR-H3 of any one of the sequences shown in Table 8.

In some embodiments a binding agent or the antigen binding portion of a binding agent comprises a heavy chain variable region having at least 70%, 75%, 85%, 86%, 87%, 88%, 89%, 90%, 91%, 92%, 93%, 94%, 95%, 96%, 97%, 98%, or at least 99% identity to a sequence of Table 9. In some embodiments a binding agent or the antigen binding portion of a binding agent comprises a heavy chain variable region sequence of Table 9.

TABLE 9

VARIABLE HEAVY CHAIN SEQUENCES

| ID | Clone | Amino Acid Sequence |
|---|---|---|
| SEQ ID NO: 94 | F5_P5_B9_H | QVQLKESGPGLVAPSQSLSITCTVSGFSLTNYGVNWVRQPPGKGLEWLGLIWGGGDTDYNSALKSRLSISKDNSKSQVFLKMETNSLQTDDTARYYCARDYYGFDYWGQGTTLTVSS |
| SEQ ID NO: 95 | F6A_P12_F12_H | EVKLVESGGGLVQPGGSLRLSCATSGFTFTDYYMSWVRQPPGKALEWLGFIRNKANGYTTKYSASVKGRFTISRDNSQSILYLQMNTLRAEDSATYYCSKDRGYFDYWGQGTTLTVSS |

TABLE 9-continued

VARIABLE HEAVY CHAIN SEQUENCES

| ID | Clone | Amino Acid Sequence |
|---|---|---|
| SEQ ID NO: 96 | F6A_P8E2_H | VNSEVQLQQSGAELVRPGALVKLSCKASGFNINDYFMH WVKQRPEQGLEWIGWIDPENGNTIYDPKFQGKASITADT SSNTAYLQLSSLTSEDTAVYYCARGGNYLRESYYYAMD YWGQGTSVTVSS |
| SEQ ID NO: 97 | F6B_P1_H5_H | VLSEVLLQQSGPELVKPGASVKIPCKASGYTFTDYNMDW VKQSHGKSLEWIGDINPNNGGTIYNQKFKGKATLTVDKS SSTAYMELRSLTSEDTAVYYRARGDYYGSSRYYYAMDY WGQGTSVTVSS |
| SEQ ID NO: 98 | F6B1_P3_D12_H | QVQLQQSGAELAKPGASVKMSCRASGYTFTSYWMHWV KQRPGQGLDWIGYIKPSTDNTEYNQKFKDKATLTADKSS STAYMQLSSLTSEDSAVYYCARSYGNYPLMDYWGQGTS VTVSS |
| SEQ ID NO: 99 | F6B1P3E9_H | QVQLQQSGAELAKPGASVKMSCRASGYTFTSYWMHWV KQRPGQGLDWIGYIKPSTDNTEYNQKFKDKATLTADKSS STAYMQLSSLTSEDSAVYYCARSYGNYPLMDYWGQGTS VTVSS |
| SEQ ID NO: 100 | F6B_1_P1_E2_H | QVQLQQSGAELAKPGASVKMSCKASGYTFTSYWMHWV KQRPGQGLEWIGYINPSTDYTEYNQKFKDKATLTADKSS TTAYMQLSSLTSEDSAVYYCVRSYGNYPLMDYWGQGTS VTVSS |
| SEQ ID NO: 101 | F6B_P3_E2_H | QVQLQQSGAELAKPGASVKMSCKASGYTFTSYWMHWV KQRPGQGLEWIGYINPSTDYTEYNQKFKDKATLTADKSS TTAYMQLSSLTSEDSAVYYCVRSYGNYPLMDYWGQGTS VTVSS |
| SEQ ID NO: 102 | F6B_P2_D4_H | QVQLQQSGAELAKPGASVKMSCKASGYTFTSYWMHWV KQRPGQGLEWIGYINPSTDYIEYNQKFKDKATLTAGKSS STAYMQLSSLTSEDSAVYYCARSYGNFPLMDYWGQGTS VTVSS |
| SEQ ID NO: 103 | Consensus | QVQLQQSGAELAKPGASVKMSC(K/R)ASGYTFTSYWMH WVKQRPGQGL(E/D)WIGYI(K/N)PSTD(Y/N)(T/I)EYNQKF KDKATLTADKSS(S/T)TAYMQLSSLTSEDSAVYYC(A/V)R SYGN(Y/F)PLMDYWGQGTSVTVSS |

In some embodiments a binding agent or the antigen binding portion of a binding agent comprises a humanized heavy chain variable region having at least 70%, 75%, 85%, 86%, 87%, 88%, 89%, 90%, 91%, 92%, 93%, 94%, 95%, 96%, 97%, 98%, or at least 99% identity to a sequence of Table 10. In some embodiments a binding agent or the antigen binding portion of a binding agent comprises a humanized heavy chain variable region sequence of Table 10.

TABLE 10

Humanized P3D12 Heavy Chains

| ID | Clone | Amino Acid Sequence |
|---|---|---|
| SEQ ID NO: 104 | P3D12 VH | QVQLQQSGAELAKPGASVKMSCRASGYTFTSYWMHWVKQ RPGQGLDWIGYIKPSTDNTEYNQKFKDKATLTADKSSSTAY MQLSSLTSEDSAVYYCARSYGNYPLMDYWGQGTSVTVSS |
| SEQ ID NO: 105 | P3D12 VH-fra | QVQLQQSGAEVKKPGASVKVSCKASGYTFTSYWMHWVKQ RPGQGLDWIGYIKPSTDNTEYNQKFKDRVTLTADKSTSTAY MQLSNLISEDTAVYYCARSYGNYPLMDYWGQGTSVTVSS |
| SEQ ID NO: 106 | P3D12 VH-ven | QVQLVQSGAEVAKPGASVKMSCKASGYTFTSYWMHWVKQ APGQGLDWIGYIKPSTDNTEYNQKFKDKATLTADKSTSTAY MQLSSLRSEDTAVYYCARSYGNYPLMDYWGQGTTVTVSS |
| SEQ ID NO: 107 | P3D12 VH-abb/sdr | QVQLVQSGAEVKKPGASVKVSCKASGYTFTSYWMHWVKQ APGQGLDWMGYIKPSTDNTEYAQKFQGRVTLTADKSTSTAY MELSSLRSEDTAVYYCARSYGNYPLMDYWGQGTTVTVSS |
| SEQ ID NO: 108 | P3D12 VH-cdr | QVQLVQSGAEVKKPGASVKVSCKASGYTFTSYWMHWVKQ APGQGLDWIGYIKPSTDNTEYNQKFKDKATLTADKSTSTAY MELSSLRSEDTAVYYCARSYGNYPLMDYWGQGTTVTVSS |

In some embodiments a binding agent, or an antigen binding portion of a binding agent, comprises a CDR-L3 comprising an amino acid sequence at least 70%, at least 75%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to any one of the amino acid sequences of SEQ ID Nos 26 to 36 (e.g., a CDR-L3 sequence selected from Table 3) and a CDR-H3 comprising an amino acid sequence at least 70%, at least 75%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to any one of the amino acid sequences of SEQ ID Nos 79 to 93 (e.g., a CDR-H3 sequence selected from Table 8). In some embodiments a binding agent, or an antigen binding portion of a binding agent, comprises a CDR-L3 comprising an amino acid sequence at least 70%, at least 90%, at least 95%, at least 98%, at least 99% or 100% identical to the amino acid sequence of SEQ ID NO: 34 or 35, and a CDR-H3 comprising an amino acid sequence at least 70%, at least 90%, at least 95%, at least 98%, at least 99% or 100% identical to the amino acid sequence of SEQ ID NO: 87, 88, 92 or 93

In some embodiments a binding agent, or an antigen binding portion of a binding agent, comprises a CDR-L3 comprising an amino acid sequence at least 70%, at least 90%, or 100% identical to any one of the amino acid sequences of SEQ ID Nos 26 to 36 (e.g., a CDR-L3 sequence selected from Table 3), a CDR-L2 comprising an amino acid sequence at least 70%, at least 90%, or 100% identical to any one of the amino acid sequences of SEQ ID Nos 16 to 25 (e.g., a CDR-L2 sequence selected from Table 2), a CDR-H3 comprising an amino acid sequence at least 70%, at least 90%, or 100% identical to any one of the amino acid sequences of SEQ ID Nos 79 to 93 (e.g., a CDR-H3 sequence selected from Table 8) and a CDR-H2 comprising an amino acid sequence at least 70%, at least 90%, or 100% identical to any one of the amino acid sequences of SEQ ID Nos 62 to 78 (e.g., a CDR-H2 sequence selected from Table 7). In some embodiments a binding agent, or an antigen binding portion of a binding agent, comprises a CDR-L3 comprising an amino acid sequence at least 70%, at least 90%, or 100% identical to the amino acid sequence of SEQ ID NO: 34 or 35, a CDR-L2 comprising an amino acid sequence at least 70%, at least 90%, or 100% identical to the amino acid sequence of SEQ ID NO: 24 or 25, a CDR-H3 comprising an amino acid sequence at least 70%, at least 90%, or 100% identical to the amino acid sequence of SEQ ID NO: 87, 88, 92 or 93 and a CDR-H2 comprising an amino acid sequence at least 70%, at least 90%, or 100% identical to the amino acid sequence of SEQ ID NO: 70, 71 or 78.

In some embodiments a binding agent, or an antigen binding portion of a binding agent, comprises a CDR-L3 comprising an amino acid sequence at least 70%, at least 90%, or 100% identical to any one of the amino acid sequences of SEQ ID Nos 26 to 36 (e.g., a CDR-L3 sequence selected from Table 3), a CDR-L2 comprising an amino acid sequence at least 70%, at least 90%, or 100% identical to any one of the amino acid sequences of SEQ ID Nos 16 to 25 (e.g., a CDR-L2 sequence selected from Table 2), a CDR-L1 comprising an amino acid sequence at least 70%, at least 90%, or 100% identical to any one of the amino acid sequences of SEQ ID Nos 1 to 15 (e.g., a CDR-L1 sequence selected from Table 1), a CDR-H3 comprising an amino acid sequence at least 70%, at least 90%, or 100% identical to any one of the amino acid sequences of SEQ ID Nos 79 to 93 (e.g., a CDR-H3 sequence selected from Table 8), a CDR-H2 comprising an amino acid sequence at least 70%, at least 90%, or 100% identical to any one of the amino acid sequences of SEQ ID Nos 62 to 78 (e.g., a CDR-H2 sequence selected from Table 7), and a CDR-H1 comprising an amino acid sequence at least 70%, at least 90%, or 100% identical to any one of the amino acid sequences of SEQ ID Nos 50 to 61 (e.g., a CDR-H1 sequence selected from Table 6). In some embodiments a binding agent, or an antigen binding portion of a binding agent, comprises a CDR-L3 comprising an amino acid sequence at least 70%, at least 90%, or 100% identical to the amino acid sequence of SEQ ID Nos 34 or 35, a CDR-L2 comprising an amino acid sequence at least 70%, at least 90%, or 100% identical to the amino acid sequence of SEQ ID NO: 24 or 25, a CDR-L1 comprising an amino acid sequence at least 70%, at least 90%, or 100% identical to the amino acid sequence of SEQ ID NO: 9, 10 or 15, a CDR-H3 comprising an amino acid sequence at least 70%, at least 90%, or 100% identical to the amino acid sequence of SEQ ID NO: 87 or 88, a CDR-H2 comprising an amino acid sequence at least 70%, at least 90%, or 100% identical to the amino acid sequence of SEQ ID NO: 70, 71 or 78, and a CDR-H1 comprising an amino acid sequence at least 70%, at least 90%, or 100% identical to the amino acid sequence of SEQ ID NO: 58 or 59.

In some embodiments a binding agent, or an antigen binding portion of a binding agent, comprises a heavy chain variable region comprising an amino acid sequence at least 70%, at least 75%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to any one of the amino acid sequences of SEQ ID Nos 94 to 108 (e.g., a heavy chain variable region selected from Tables 9 and 10), and a light chain variable region comprising an amino acid sequence at least 70%, at least 75%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to any one of the amino acid sequences of SEQ ID Nos 37 to 49 (e.g., a light chain variable region selected from Tables 4 and 5). In some embodiments a binding agent, or an antigen binding portion of a binding agent, comprises a heavy chain variable region comprising an amino acid sequence at least 90% identical to any one of the amino acid sequences of SEQ ID Nos 104 to 108 (e.g., a heavy chain variable region selected from Table 10), and a light chain variable region comprising an amino acid sequence at least 90% identical to any one of the amino acid sequences of SEQ ID Nos 45 to 49 (e.g., a light chain variable region selected from Table 5).

The abbreviations of "abb", "sdr", "fra", "ven." and "cdr" as used herein are explained below. The abbreviation "cdr" or "CDR" refer to a Complementarity-Determining Region. The abbreviation "abb" refers to abbreviated CDR according to Padlan et al. (1995) "Identification of specificity-determining residues in antibodies" FASEB J 9:133-139. In some embodiments, abbreviated CDRs are defined as residues 27D-34, 50-55, and 89-96 in the light chain, and 31-35B, 50-58, and 95-101 in the heavy chain, which are grafted onto an appropriate human scaffold. The critical framework residues are often preserved. The abbreviation "sdr" refers to "specificity determining residues" according to Padlan et al. (1995) which are residues thought to be involved in antigen binding. The abbreviation "fra" refers to the "Frankenstein approach" based on the suggestion of Wu and Kabat (1992) "Possible use of similar framework region amino acid sequences between human and mouse immunoglobulins for humanizing mouse antibodies" Mol Immunol 29:1141-1146. The abbreviation "ven" refers to "Veneering" according to Padlan (1991), "A possible procedure for reducing the immunogenicity of antibody variable domains while preserving their ligand-binding properties" Mol Immunol 28:489-498.

The term "percent identical" or "percent identity" refers to sequence identity between two amino acid sequences. Identity can be determined by comparing a position in each sequence which may be aligned for purposes of comparison. When an equivalent position in the compared sequences is occupied by the same amino acid, then the molecules are identical at that position. When the equivalent site is occupied by the same or a similar amino acid residue (e.g., similar in steric and/or electronic nature), then the molecules can be referred to as homologous (similar) at that position. Expression as a percentage of homology, similarity, or identity refers to a function of the number of identical or similar amino acids at positions shared by the compared sequences. Expression as a percentage of homology, similarity, or identity refers to a function of the number of identical or similar amino acids at positions shared by the compared sequences. Various alignment algorithms and/or programs may be used, including FASTA, BLAST, or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences.

Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. In some embodiments an alignment program that permits gaps in the sequence is utilized to align the sequences. The Smith-Waterman is one type of algorithm that permits gaps in sequence alignments. See Meth. Mol. Biol. 70:173-187 (1997). Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer. This approach improves ability to pick up distantly related matches, and is especially tolerant of small gaps and nucleotide sequence errors. Nucleic acid-encoded amino acid sequences can be used to search both protein and DNA databases.

In some embodiments a binding agent, or antigen binding portion of a binding agent comprises one or more CDRs selected from a light chain variable region of Tables 4 and 5. In some embodiments a binding agent, or antigen binding portion of a binding agent comprises one or more CDRs selected from a heavy chain variable region of Tables 9 and 10. In some embodiments a binding agent, or antigen binding portion of a binding agent comprises one or more CDRs selected from a light chain variable region of Tables 4 and 5 and one or more CDRs selected from a heavy chain variable region of Tables 9 and 10. In certain embodiments, a binding agent, or antigen binding portion of a binding agent, comprises a CDR-L1, a CDR-L2, and a CDR-L3, each selected from any one of the light chain variable regions of Tables 4 and 5, and a CDR-H1, a CDR-H2, and a CDR-H3, each selected from any one of the heavy chain variable regions of Tables 9 and 10. An amino acid sequence of a CDR (e.g., a CDR-L1, CDR-L2, CDR-L3, CDR-H1, CDR-H2, and CDR-H3) can be identified within a heavy chain or light chain variable region disclosed herein by any suitable method described herein or known to those skilled in the art.

In some embodiments a binding agent comprises one or more suitable sequences selected from Tables 1-10 wherein the selected polypeptide sequence comprises 0 to 5, 1 to 5, 0 to 10, 1 to 10, 0 to 15, or 1 to 15 amino acid modifications where an amino acid modification can be an amino acid addition, an amino acid deletion and/or an amino acid substitution. In some embodiments, a binding agent disclosed herein comprises one or more amino acid analogues, non-native amino acids or amino acid derivatives.

In certain embodiments, a binding agent, or antigen binding portion of a binding agent comprises one or more framework regions (FR). Framework regions are often located between CDRs and/or flank CDR sequences of a heavy or light chain variable region of an antibody or binding agent. In mammals, a heavy chain variable region often comprises four framework regions and a light chain variable region often comprises four framework regions. Any suitable method can be used to identify one or more framework regions in an antibody, in a variable region of an antibody or in a binding agent. A binding agent may comprise synthetic or naturally occurring framework regions which are unmodified or modified (e.g., optimized) as discussed below.

In some embodiments a binding agent, or antigen binding portion thereof is chimeric, grafted and/or humanized. Chimeric, grafted and or humanized binding agents often comprise modified or substituted constant regions and/or framework regions while maintaining binding specificity to cMET, or a portion thereof. In some embodiments a binding agent, or antigen binding portion thereof, comprises constant regions, framework regions, or portions thereof, derived from a human antibody. In some embodiments a binding agent, or antigen binding portion thereof, comprises fully synthetic portions, one or more amino acids, or sequences of amino acids that are not found in native antibody molecules.

Naturally occurring framework regions, or portions thereof may be obtained from any suitable species. In certain embodiments the complementarity determining regions (CDRs) of the light and heavy chain variable regions of a binding agent, or an antigen binding portion thereof, is grafted into framework regions from the same, or another, species. For example, one or more framework regions of a binding agent may be derived from a rodent species (e.g., a mouse or rat) or a primate species (e.g., a human).

In certain embodiments, the CDRs of the light and/or heavy chain variable regions of a binding agent, or an antigen binding portion thereof, can be grafted to consensus human framework regions. To create consensus human framework regions, in certain embodiments, framework regions from several human heavy chain or light chain amino acid sequences can be aligned to identify a consensus sequence. In certain embodiments, the heavy chain or light chain framework regions of an antibody or binding agent are replaced with one or more framework regions, or portions thereof, from a different heavy chain or light chain variable region. In some embodiments a binding agent, or antigen binding portion thereof, comprises one or more human framework regions. In certain embodiments a binding agent, or antigen binding portion thereof, comprises at least 1, 2, 3, 4, 5, 6, 7, 8, 9 or 10 human framework regions. In some embodiments a binding agent, or antigen binding portion thereof, comprises one or more mouse framework regions. In certain embodiments a binding agent, or antigen binding portion thereof, comprises at least 1, 2, 3, 4, 5, 6, 7, 8, 9 or 10 mouse framework regions. In certain embodiments a binding agent, or antigen binding portion thereof, comprises one or more human framework regions and one or more mouse framework regions.

Methods of generating chimeric, humanized and/or optimized antibodies or binding agents, for example by modifying, substituting or deleting framework regions, or portions thereof, are known. Non-limiting examples of CDR grafting are described, e.g., in U.S. Pat. Nos. 6,180,370, 6,054,297, 5,693,762, 5,859,205, 5,693,761, 5,565,332, 5,585,089, and 5,530,101, and in Jones et al, Nature, 321: 522-525 (1986); Verhoeyen et al, Science, 239:1534-1536 (1988), and Winter, FEBS Letts., 430:92-94 (1998). Additional non-limiting examples of generating chimeric, grafted and/or humanized binding agents include U.S. Pat. Nos. 5,530,101; 5,707,622; 5,994,524; 6,245,894; Queen et al., (1988) PNAS 86:10029-10033; Riechmann et al., Nature (1988) 332:323-327; Antibody Engineering: Methods and Protocols, Vol. 248 of Methods in molecular biology, edited by Benny K. C. Lo, Springer Science & Business Media, (2004); and Antibody Engineering, Vol. 1, Roland E. Kontermann, Stefan Duebel, Edition 2, Publisher Springer Science & Business Media, (2010). In some embodiments a binding agent can be humanized by exchanging one or more framework regions, or portions thereof (e.g., one or more amino acids), with one or more framework regions, or portions thereof from a human antibody. In certain embodiments, an antibody or binding agent can be humanized or grafted by transferring one or more CDRs (e.g., 1, 2, 3, 4, 5 or all 6 CDRs) from a donor binding agent (e.g., a mouse monoclonal antibody) to an acceptor binding agent (e.g., a human antibody) while retaining the binding specificity of the donor binding agent. In certain embodiments, the process of making a chimeric, grafted or humanized binding agent comprises making one or more amino acid substitutions, additions or deletions in a constant region or framework region of a binding agent. In certain embodiments, techniques such as "reshaping", "hyperchimerization," or "veneering/resurfacing" can be used to produce humanized binding agents. (e.g., see Vaswami et al, Annals of Allergy, Asthma, & Immunol. 81:105 (1998); Roguska et al, Prot. Engin., 9:895-904 (1996); and U.S. Pat. No. 6,072,035). In some aspects, a binding agent is modified by a method discussed above, or by another suitable method, to reduce immunogenicity (e.g., see Gilliland et al, J. Immunol, 62(6): 3663-71 (1999)).

In certain embodiments, an amino acid sequence of a binding agent is modified to optimize binding affinity for a target (e.g., cMET), species cross-reactivity, solubility and/or function (e.g., agonist activity, or lack thereof). In some embodiments a specific combination of CDRs disclosed herein can be optimized for binding to cMET, and/or to optimize a function or characteristic of a binding agent disclosed herein. For example, a characterized light chain variable region disclosed herein (e.g., a light chain variable region of SEQ ID NO:48) can be co-expressed, using a suitable expression system, with a library of heavy chain variable regions comprising a CDR-H1 and CDR-H2 of a characterized heavy chain variable region (e.g., a heavy chain variable region of SEQ ID NO: 107), where the CDR-H3 is replaced with a library of CDR-H3 sequences, which may include one or more CDR-H3 regions of Table 8, for example. The resulting light chain/heavy chain binding agents can be screened for binding to cMET and/or for a specific function. Optimized binding agents can be identified and the amino acid sequence of the CDR-H3 can be identified by a suitable method. The above screening method can be used to identify binding agents comprising specific combinations of CDRs, or specific optimized CDR sequences (e.g., CDR sequences comprising amino acid substitutions, additions or deletions) that provide a binding agent with improved binding specificity, binding affinity and/or function. Such methods of screening and optimizing binding agents are known (e.g., see Portolano et al., (1993) Journal of Immunology 150:880-887; and Clarkson et al., (1991) Nature 352:624-628). Such references teach methods of producing antibodies that bind a specific antigen by using known variable light chain, known variable heavy chains, or portion thereof (e.g., CDRs thereof) by screening a library of complementary variable regions.

In certain embodiments, a binding agent is modified to eliminate or add glycosylation sites in order to optimize affinity and/or function of a binding agent (e.g., see Co et al, Mol. Immunol, 30:1361-1367 (1993)). In some embodiments the number and/or type of glycosylation sites in a binding agent is modified or altered. An N-linked glycosylation site is often characterized by the sequence Asn-X-Ser or Asn-X-Thr, where the amino acid residue designated as X can be any amino acid residue except proline. The substitution of amino acid residues to create this sequence provides a potential new site for the addition of an N-linked carbohydrate chain. Alternatively, substitutions which eliminate this sequence will remove an existing N-linked carbohydrate chain. Also provided in certain embodiments is a rearrangement of N-linked carbohydrate chains where one or more N-linked glycosylation sites (typically those that are naturally occurring) are eliminated and one or more new N-linked sites are created. In some embodiments a binding agent is modified by deleting one or more cysteine residues or substituting one or more cysteine residues for another amino acid (e.g., serine) as compared to an unmodified binding agent. In certain embodiments cysteine variants can be useful for optimizing expression, secretion, and/or solubility.

In certain embodiments a binding agent is modified to include certain amino acid additions, substitutions, or deletions designed or intended, for example, to reduce susceptibility of a binding agent to proteolysis, reduce susceptibility of a binding agent to oxidation, increase serum half-life and/or confer or modify other physicochemical, pharmacokinetic or functional properties of a binding agent.

In some embodiments a binding agent specifically binds to a mammalian cMET, or portion thereof. In some embodiments a binding agent specifically binds to an extracellular domain or extracellular regions of a mammalian cMET, or a portion thereof. In certain aspects, a binding agent specifically binds to a wild-type cMET produced by a cell of an unaltered (non-genetically modified) mammal found in nature. In certain aspects a binding agent specifically binds to a naturally occurring cMET variant. In certain aspects a binding agent specifically binds to a cMET comprising one or more amino acid substitutions, additions or deletions. In certain embodiments a binding agent specifically binds to a cMET produced and/or expressed on the surface of a cell of a human, non-human primate, dog, cat, or rodent (e.g., a mouse or rat). In certain embodiments, a binding agent specifically binds to one or more cMET polypeptides, or a portion thereof, having an amino acid sequence of any one of SEQ ID Nos 109 to 113. In certain embodiments, a binding agent specifically binds to a human cMET. In certain embodiments, a binding agent specifically binds to an extracellular domain of human cMET. In certain embodiments, a binding agent specifically binds to a human cMET, and/or an extracellular domain thereof, wherein the human cMET comprises an E168 to D168 substitution (i.e., an E168D variant of cMET). In certain embodiments, a binding agent specifically binds to a human cMET, and/or an extracellular domain thereof, wherein the human cMET comprises an N375 to S375 substitution (i.e., an N375S variant of human cMET).

The term "specifically binds" refers to a binding agent that binds a target peptide in preference to binding other molecules or other peptides as determined by, for example, as determined by a suitable in vitro assay (e.g., an Elisa, Immunoblot, Flow cytometry, and the like). A specific binding interaction discriminates over non-specific binding interactions by about 2-fold or more, often about 10-fold or more, and sometimes about 100-fold or more, 1000-fold or more, 10,000-fold or more, 100,000-fold or more, or 1,000,000-fold or more.

In some embodiments a binding agent that specifically binds to cMET, or a portion thereof, is a binding agent that binds cMET, or a portion thereof (e.g., an extracellular domain of cMET), with a binding affinity constant (KD) equal to or less than 100 nM, equal to or less than 50 nM, equal to or less than 25 nM, equal to or less than 10 nM, equal to or less than 5 nM, equal to or less than 1 nM, equal to or less than 900 pM, equal to or less than 800 pM, equal to or less than 750 pM, equal to or less than 700 pM, equal to or less than 600 pM, equal to or less than 500 pM, equal to or less than 400 pM, equal to or less than 300 pM, equal to or less than 200 pM, or equal to or less than 100 pM. In some embodiments a binding agent that specifically binds to cMET, or a portion thereof, is a binding agent that binds human cMET, or a portion thereof (e.g., an extracellular domain of human cMET), with a binding affinity constant (KD) equal to or less than 100 nM, equal to or less than 50 nM, equal to or less than 25 nM, equal to or less than 10 nM, equal to or less than 5 nM, equal to or less than 1 nM, equal to or less than 900 pM, equal to or less than 800 pM, equal to or less than 750 pM, equal to or less than 700 pM, equal to or less than 600 pM, equal to or less than 500 pM, equal to or less than 400 pM, equal to or less than 300 pM, equal to or less than 200 pM, or equal to or less than 100 pM. In some embodiments a binding agent that specifically binds to cMET, or a portion thereof, is a binding agent that binds specifically to cMET, or a portion thereof, derived from a non-human species (e.g., a non-human primate, or rodent; e.g., a mouse or rat), with a binding affinity constant (KD) equal to or less than 100 nM, equal to or less than 50 nM, equal to or less than 25 nM, equal to or less than 10 nM, equal to or less than 5 nM, equal to or less than 1 nM, equal to or less than 900 pM, equal to or less than 800 pM, equal to or less than 750 pM, equal to or less than 700 pM, equal to or less than 600 pM, equal to or less than 500 pM, equal to or less than 400 pM, equal to or less than 300 pM, equal to or less than 200 pM, or equal to or less than 100 pM. In certain embodiments, a binding agent disclosed herein specifically binds human cMET, or a portion thereof, and specifically binds to cMET, or a portion thereof, derived from a non-human primate. In certain embodiments, a binding agent disclosed herein specifically binds human cMET, or a portion thereof, and specifically binds to cMET, or a portion thereof, derived from a rodent (e.g., a mouse or rat). In certain embodiments, a binding agent (i) specifically binds to a human cMET, or portion thereof (e.g., an extracellular domain of human cMET) with a KD of 10 nM or less, or 1 nM or less, and (ii) specifically binds to a rat or mouse cMET, or portion thereof (e.g., an extracellular domain of rat or mouse cMET) with a KD of 100 nM or less, 90 nM or less, 80 nM or less, 70 nM or less, 60 nM or less, 50 nM or less, 40 nM or less, 30 nM or less, 20 nM or less or 10 nM or less.

In some embodiments a binding agent comprises a label. As used herein, the terms "label" or "labeled" refers to incorporation of a detectable marker, e.g., by incorporation of a labeled amino acid or attachment to a polypeptide of biotin moieties that can be detected by labeled avidin (e.g., streptavidin containing a fluorescent marker or enzymatic activity that can be detected by optical or colorimetric methods). In certain embodiments, a label or marker can be attached to a binding agent to generate a therapeutic or diagnostic agent. A binding agent can be attached covalently or non-covalently to any suitable label or marker. Various methods of labeling polypeptides and glycoproteins are known to those skilled in the art and can be used. Non-limiting examples of labels for polypeptides include, but are not limited to, the following: radioisotopes or radionuclides (e.g., $^{3}$H, $^{14}$C, $^{15}$N, $^{35}$S, $^{90}$Y, $^{99}$Tc, $^{125}$I, $^{131}$I), fluorescent labels, enzymatic labels (e.g., horseradish peroxidase, (β-galactosidase, luciferase, alkaline phosphatase), chemiluminescent labels, a metallic label, a chromophore, an electrochemiluminescent label, a phosphorescent label, a quencher (e.g., a fluorophore quencher), a fluorescence resonance energy transfer (FRET) pair (e.g., donor and acceptor), a dye, an enzyme substrate, a small molecule, a mass tag, quantum dots, nanoparticles, biotinyl groups, predetermined polypeptide epitopes recognized by a secondary reporter (e.g., leucine zipper pair sequences, binding sites for secondary antibodies, metal binding domains, epitope tags), the like or combinations thereof.

In some embodiments a binding agent comprises a suitable carrier. A binding agent can be attached covalently or non-covalently to a suitable carrier. Non-limiting examples of a carrier include agents or molecules that alter or extend the in vivo half-life of a binding agent, polyethylene glycol, glycogen (e.g., by glycosylation of a binding agent), a dextran, a carrier or vehicle described in U.S. Pat. No. 6,660,843, the like or combinations thereof.

In some embodiments a binding agent comprises a suitable therapeutic agent. A binding agent can be attached covalently or non-covalently to any suitable therapeutic agent. Non-limiting examples of a therapeutic agent include a medication, toxin, radioisotope, ligand, receptor, cytokine, antibody, anti-neoplastic agent, inhibitor (e.g., a receptor antagonist, an enzyme inhibitor), a cytokine or an agent disclosed in U.S. Pat. No. 6,660,843, which is incorporated herein by reference, the like or combinations thereof. Non-limiting examples of anti-neoplastic agents include an auristatin (e.g., monomethyl auristatin E (MMAE), monomethyl auristatin F (MMAF), and the like), a dolastatin, a maytansine, a tubulysin, an irinotecan or derivative or metabolite thereof (e.g., SN38), a calicheamicin, a pyrrolobenzodiazepine (PBD), a duocarmycin, a doxorubicin, a *pseudomonas* exotoxin A (e.g., PE38), derivatives thereof, the like or combinations thereof. Accordingly, in certain embodiments, a binding agent disclosed herein comprises an anti-neoplastic agent.

In some embodiments a label, therapeutic agent or carrier is bound to a binding agent by use of a suitable linker. Non-limiting examples of a suitable linker include silanes, thiols, phosphonic acid, polyethylene glycol (PEG), amino acids and peptides, polymers thereof, derivatives thereof, the like and combinations thereof. Methods of attaching two or more molecules using a linker are to those skilled in the art and are sometimes referred to as "crosslinking."

In some embodiments a label, therapeutic agent, carrier or linker is attached to a suitable thiol group of a binding agent (e.g., a thiol group of a cysteine residue). Any suitable amino acid residue of a constant region or framework region of a binding agent can be substituted with an amino acid residue containing a thiol group (e.g., a cysteine) for the purpose of attaching a label, therapeutic agent, carrier or linker. Non-limiting examples of amino acids that can be substituted with a thiol containing amino acid residue include A118, S119, S239, V282, T289, N361, and V422 of an IgG2, S115, S252, V289, T306, and N384 of an IgG1, or a corresponding position in an IgG1, IgG2, IgG3 or IgG4. Other non-limiting examples of attaching a label, therapeutic agent, carrier and/or linker to a binding agent include reacting an amine with an N-hydroxysuccinimide (NHS) ester, an imidoester, a pentafluorophenyl (PFP) ester, a hydroxymethyl phosphine, an oxirane or any other carbonyl compound; reacting a carboxyl with a carbodiimide; reacting a sulfhydryl with a maleimide, a haloacetyl, a pyridyldisulfide, and/or a vinyl sulfone; reacting an aldehyde with a hydrazine; reacting any non-selective group with diazirine and/or aryl azide; reacting a hydroxyl with isocyanate; reacting a hydroxylamine with a carbonyl compound; the like and combinations thereof.

In certain embodiments, a binding agent comprises one or more functional characteristics. Accordingly, a binding agent can be described structurally and functionally (e.g., by what it does, or by what it is capable of doing). Binding agents disclosed herein can bind specifically to an extracellular portion of cMET, for example, an extracellular portion of cMET present on the surface of a cell. In some embodiments a cell is a human cancer cell or human neoplastic cell that expresses cMET. In certain embodiments, upon binding cMET on the surface of a cell, certain binding agents disclosed herein induce internalization of cMET. In some embodiments, a binding agent binds specifically to cMET, or a portion thereof, and induces degradation of cMET on a cell (e.g., on a cancer cell). Internalization and/or degradation of cell surface bound receptors induced by binding of a ligand or binding agent is a known biological process. The ability of a binding agent to induce cMET internalization and/or degradation is easily observed, without undue experimentation, by use of a suitable experimental assay. Accordingly, in some embodiments, a binding agent binds specifically to cMET, or a portion thereof, on a cell surface and induces internalization and/or degradation of cMET.

In some embodiments, a binding agent binds specifically to cMET, or a portion thereof, and induces or promotes signaling (e.g., tyrosine kinase activity). In certain embodiments a binding agent binds specifically to cMET on a cell surface and does not detectably induce or promote signaling (e.g., tyrosine kinase activity). Accordingly, in certain embodiments, an anti-cMET binding agent disclosed herein does not have detectable cMET agonist activity. In certain embodiments, an anti-cMET binding agent lacks agonistic activity upon binding cMET on a cell surface and/or fails to induce or promote detectable tyrosine kinase activity upon binding to cMET on a cell surface. In some embodiments, an anti-cMET binding agent is a cMET antagonist. In certain embodiments, an anti-cMET binding agent decreases, inhibits, reduces, blocks or prevents signaling through a cMET receptor and/or decreases, inhibits, reduces, blocks or prevents a cMET receptor from inducing or promoting detectable tyrosine kinase activity. In some embodiments, an anti-cMET binding agent disclosed herein decreases, inhibits, reduces, prevents or blocks cMET from binding to its native cognate ligand (e.g., hepatocyte growth factor, or an isoform thereof).

In certain embodiments, contacting a cell of a subject with a binding agent disclosed herein induces or promotes death of the cell. In certain embodiments, contacting a cell of a subject with a binding agent disclosed herein induces or promotes cell-death by apoptosis or necrosis of a cell expressing cMET. In certain embodiments, contacting a cell of a subject with a binding agent disclosed herein induces or promotes death of the cell by an ADCC, ADCP or complement-dependent cellular cytotoxicity (CDCC) process.

In certain embodiments, contacting a cell of a subject with a binding agent disclosed herein decreases, inhibits, or reduces mitosis of the cell. In certain embodiments, contacting a cell of a subject with a binding agent disclosed herein decreases, inhibits, or reduces metastasis of the cell.

In some embodiments, presented herein is a composition or pharmaceutical composition comprising one or more binding agents that binds specifically to cMET, or a portion thereof (e.g., an extracellular domain of cMET, or a portion thereof).

A pharmaceutical composition can be formulated for a suitable route of administration. In some embodiments a pharmaceutical composition is formulated for subcutaneous (s.c.), intradermal, intramuscular, intraperitoneal and/or intravenous (i.v.) administration. In certain embodiments, a pharmaceutical composition can contain formulation materials for modifying, maintaining, or preserving, for example, the pH, osmolarity, viscosity, clarity, color, isotonicity, odor, sterility, stability, rate of dissolution or release, adsorption or penetration of the composition. In certain embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates (e.g., phosphate buffered saline) or suitable organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counter ions (such as sodium); solvents (such as glycerin, propylene glycol or polyethylene glycol); diluents; excipients and/or pharmaceutical adjuvants (Remington's Pharmaceutical Sciences, 18th Ed., A. R. Gennaro, ed., Mack Publishing Company (1995)).

In certain embodiments, a pharmaceutical composition comprises a suitable excipient, non-limiting example of which include anti-adherents (e.g., magnesium stearate), a binder, fillers, monosaccharides, disaccharides, other carbohydrates (e.g., glucose, mannose or dextrins), sugar alcohols (e.g., mannitol or sorbitol), coatings (e.g; cellulose, hydroxypropyl methylcellulose (HPMC), microcrystalline cellulose, synthetic polymers, shellac, gelatin, corn protein zein, enterics or other polysaccharides), starch (e.g., potato, maize or wheat starch), silica, colors, disintegrants, flavors, lubricants, preservatives, sorbents, sweeteners, vehicles, suspending agents, surfactants and/or wetting agents (such as pluronics, PEG, sorbitan esters, polysorbates such as polysorbate 20, polysorbate 80, triton, tromethamine, lecithin, cholesterol, tyloxapal), stability enhancing agents (such as sucrose or sorbitol), and tonicity enhancing agents (such as alkali metal halides, sodium or potassium chloride, mannitol, sorbitol), and/or any excipient disclosed in Remington's Pharmaceutical Sciences, 18th Ed., A. R. Gennaro, ed., Mack Publishing Company (1995). The term "binder" as used herein refers to a compound or ingredient that helps keeps a pharmaceutical mixture combined. Suitable binders for making pharmaceutical formulations and are often used in the preparation of pharmaceutical tablets, capsules and granules are known to those skilled in the art. For clarification, the term "binding agent" as used herein does not refer to a "binder" that is used in certain pharmaceutical formulations. Although a pharmaceutical composition, in certain embodiments, may comprise a binding agent that specifically binds cMET as well as a binder.

In some embodiments a pharmaceutical composition comprises a suitable pharmaceutically acceptable additive and/or carrier. Non-limiting examples of suitable additives include a suitable pH adjuster, a soothing agent, a buffer, a sulfur-containing reducing agent, an antioxidant and the like. Non-limiting examples of a sulfur-containing reducing agent includes those having a sulfhydryl group such as N-acetylcysteine, N-acetylhomocysteine, thioctic acid, thiodiglycol, thioethanolamine, thioglycerol, thiosorbitol, thioglycolic acid and a salt thereof, sodium thiosulfate, glutathione, and a C1-C7 thioalkanoic acid. Non-limiting examples of an antioxidant include erythorbic acid, dibutylhydroxytoluene, butylhydroxyanisole, alpha-tocopherol, tocopherol acetate, L-ascorbic acid and a salt thereof, L-ascorbyl palmitate, L-ascorbyl stearate, sodium bisulfite, sodium sulfite, triamyl gallate and propyl gallate, as well as chelating agents such as disodium ethylenediaminetetraacetate (EDTA), sodium pyrophosphate and sodium metaphosphate. Furthermore, diluents, additives and excipients may comprise other commonly used ingredients, for example, inorganic salts such as sodium chloride, potassium chloride, calcium chloride, sodium phosphate, potassium phosphate and sodium bicarbonate, as well as organic salts such as sodium citrate, potassium citrate and sodium acetate.

The pharmaceutical compositions used herein can be stable over an extended period of time, for example on the order of months or years. In some embodiments a pharmaceutical composition comprises one or more suitable preservatives. Non limiting examples of preservatives include benzalkonium chloride, benzoic acid, salicylic acid, thimerosal, phenethyl alcohol, methylparaben, propylparaben, chlorhexidine, sorbic acid, hydrogen peroxide, the like and/or combinations thereof. A preservative can comprise a quaternary ammonium compound, such as benzalkonium chloride, benzoxonium chloride, benzethonium chloride, cetrimide, sepazonium chloride, cetylpyridinium chloride, or domiphen bromide (BRADOSOL®). A preservative can comprise an alkyl-mercury salt of thiosalicylic acid, such as thimerosal, phenylmercuric nitrate, phenylmercuric acetate or phenylmercuric borate. A preservative can comprise a paraben, such as methylparaben or propylparaben. A preservative can comprise an alcohol, such as chlorobutanol, benzyl alcohol or phenyl ethyl alcohol. A preservative can comprise a biguanide derivative, such as chlorohexidine or polyhexamethylene biguanide. A preservative can comprise sodium perborate, imidazolidinyl urea, and/or sorbic acid. A preservative can comprise stabilized oxychloro complexes, such as known and commercially available under the trade name PURITE®. A preservative can comprise polyglycol-polyamine condensation resins, such as known and commercially available under the trade name POLYQUART® from Henkel KGaA. A preservative can comprise stabilized hydrogen peroxide. A preservative can be benzalkonium chloride. In some embodiments a pharmaceutical composition is free of preservatives.

In some embodiments a composition, pharmaceutical composition or binding agent is substantially free of blood, or a blood product contaminant (e.g., blood cells, platelets, polypeptides, minerals, blood borne compounds or chemicals, and the like). In some embodiments a composition, pharmaceutical composition or binding agent is substantially free of serum and serum contaminants (e.g., serum proteins, serum lipids, serum carbohydrates, serum antigens and the like). In some embodiments a composition, pharmaceutical composition or binding agent is substantially free a pathogen (e.g., a virus, parasite or bacteria). In some embodiments a composition, pharmaceutical composition or binding agent is substantially free of endotoxin. In some embodiments a composition, pharmaceutical composition or binding agent is sterile. In certain embodiments, a composition or pharmaceutical composition comprises a binding agent that specifically binds an extracellular domain of cMET and a diluent (e.g., phosphate buffered saline). In certain embodiments, a composition or pharmaceutical composition comprises a binding agent that specifically binds an extracellular domain of cMET and an excipient, (e.g., sodium citrate dehydrate, or polyoxyethylene-sorbitan-20 mono-oleate (polysorbate 80)).

The pharmaceutical compositions described herein may be configured for administration to a subject in any suitable form and/or amount according to the therapy in which they are employed. For example, a pharmaceutical composition configured for parenteral administration (e.g., by injection or infusion), may take the form of a suspension, solution or emulsion in an oily or aqueous vehicle and it may contain formulation agents, excipients, additives and/or diluents such as aqueous or non-aqueous solvents, co-solvents, suspending solutions, preservatives, stabilizing agents and or dispersing agents. In some embodiments a pharmaceutical composition suitable for parental administration may contain one or more excipients. In some embodiments a pharmaceutical composition is lyophilized to a dry powder form. In some embodiments a pharmaceutical composition is lyophilized to a dry powder form, which is suitable for reconstitution with a suitable pharmaceutical solvent (e.g., water, saline, an isotonic buffer solution (e.g., PBS), and the like). In certain embodiments, reconstituted forms of a lyophilized pharmaceutical composition are suitable for parental administration (e.g., intravenous administration) to a mammal.

In some embodiments a pharmaceutical compositions described herein may be configured for topical administration and may include one or more of a binding and/or lubricating agent, polymeric glycols, gelatins, cocoa-butter or other suitable waxes or fats. In some embodiments a pharmaceutical composition described herein is incorporated into a topical formulation containing a topical carrier that is generally suited to topical drug administration and comprising any suitable material known to those skilled in the art. In certain embodiments, a topical formulation of a pharmaceutical composition is formulated for administration of a binding agent from a topical patch.

In certain embodiments, an optimal pharmaceutical composition will be determined by one skilled in the art depending upon, for example, the intended route of administration, delivery format and desired dosage (see e.g., Remington's Pharmaceutical Sciences, supra). In certain embodiments, such compositions may influence the physical state, stability, rate of in vivo release and rate of in vivo clearance of the antibodies of the invention.

In some embodiments a composition, pharmaceutical composition or binding agent described herein is used to treat a subject having or suspected of having a neoplastic disorder or cancer. In certain embodiments, a binding agent or pharmaceutical composition described herein is used in treating a neoplastic disorder or cancer in a subject, wherein the binding agent specifically binds to an extracellular domain of human cMET. Is some embodiments, presented herein is a method of treating a subject having or suspected of having a neoplastic disorder or cancer. In certain embodiments, a method of treating a subject having or suspected of having a neoplastic disorder or cancer comprises administering a therapeutically effective amount of a composition, pharmaceutical composition or binding agent described herein to the subject. In certain embodiments, a method of treatment comprises contacting a cell (e.g., one or more cells) of a subject with a therapeutically effective amount of a composition, pharmaceutical composition or binding agent described herein. In certain embodiments, a method of treatment comprises contacting a cell (e.g., one or more cells) of a subject with a therapeutically effective amount of a binding agent that specifically binding to an extracellular portion of human cMET, or variant thereof. The cell of a subject is often a cell that expresses an extracellular portion of cMET. A cell of a subject may be found inside a subject (e.g., in vivo) or outside the subject (e.g., in vitro or ex vivo).

A composition, pharmaceutical composition or binding agent disclosed herein can be used to treat a suitable neoplastic order or cancer involving a cell type that expresses cMET. Non-limiting examples of a neoplastic disorder or cancer that can be treated by a method herein includes a lung carcinoma, breast carcinoma, ovarian carcinoma, kidney carcinoma, colorectal carcinoma, gastric carcinoma, thyroid carcinoma, pancreas carcinoma, neuroblastoma, or a squamous cell carcinoma of the head and neck, cervical cancer, hepatocellular cancer, sarcomas, mesothelioma, glioblastoma, multiple myeloma, melanoma, prostate and esophageal carcinoma. In certain embodiments a neoplastic cell of a cancer or neoplastic order can be quickly assayed for expression of cMET using a suitable anti-cMET binding agent, or a novel binding agent described herein by using a suitable method (e.g., whole cell ELISA, FACs, any suitable immunoassay, and the like).

Any suitable method of administering a composition, pharmaceutical composition or binding agent to a subject can be used. The exact formulation and route of administration for a composition for use according to the methods of the invention described herein can be chosen by the individual physician in view of the patient's condition. See, e.g., Fingl et al. 1975, in "The Pharmacological Basis of Therapeutics," Ch. 1, p. 1; which is incorporated herein by reference in its entirety. Any suitable route of administration can be used for administration of a pharmaceutical composition or a binding agent described herein. Non-limiting examples of routes of administration include topical or local (e.g., transdermally or cutaneously, (e.g., on the skin or epidermis), in or on the eye, intranasally, transmucosally, in the ear, inside the ear (e.g., behind the ear drum)), enteral (e.g., delivered through the gastrointestinal tract, e.g., orally (e.g., as a tablet, capsule, granule, liquid, emulsification, lozenge, or combination thereof), sublingual, by gastric feeding tube, rectally, and the like), by parenteral administration (e.g., parenterally, e.g., intravenously, intra-arterially, intramuscularly, intraperitoneally, intradermally, subcutaneously, intracavity, intracranial, intra-articular, into a joint space, intracardiac (into the heart), intracavernous injection, intralesional (into a skin lesion), intraosseous infusion (into the bone marrow), intrathecal (into the spinal canal), intra-uterine, intravaginal, intravesical infusion, intravitreal), the like or combinations thereof.

In some embodiments a composition herein is provided to a subject. A composition that is provided to a subject is sometimes provided to a subject for self-administration or for administration to a subject by another (e.g., a non-medical professional). For example a composition described herein can be provided as an instruction written by a medical practitioner that authorizes a patient to be provided a composition or treatment described herein (e.g., a prescription). In another example, a composition can be provided to a subject where the subject self-administers a composition orally, intravenously or by way of an inhaler, for example.

Alternately, one can administer compositions for use according to the methods of the invention in a local rather than systemic manner, for example, via direct application to the skin, mucous membrane or region of interest for treating, including using a depot or sustained release formulation.

In some embodiments a pharmaceutical composition comprising a binding agent can be administered alone (e.g., as a single active ingredient (AI or e.g., as a single active pharmaceutical ingredient (API)). In other embodiments, a pharmaceutical composition comprising a binding agent can be administered in combination with one or more additional AIs/APIs, for example, as two separate compositions or as a single composition where the one or more additional AIs/APIs are mixed or formulated together with the binding agent in a pharmaceutical composition.

A pharmaceutical composition can be manufactured by any suitable manner, including, e.g., by means of conventional mixing, dissolving, granulating, dragee-making, levigating, emulsifying, encapsulating, entrapping or tableting processes.

In some embodiments a pharmaceutical composition comprising a binding agent is administered at a suitable frequency or interval as needed to obtain an effective therapeutic outcome. An effective therapeutic outcome can be determined by monitoring the number, viability, growth, mitosis, or metastasis of neoplastic or cancerous cells in a subject affected with a neoplastic disorder or cancer. Accordingly, in certain embodiments, a decrease in the number, viability, growth, mitosis, or metastasis of neoplastic or cancerous cells in a subject is considered an effective therapeutic outcome. In some embodiments, a pharmaceutical composition comprising a binding agent can be administered hourly, once a day, twice a day, three times a day, four times a day, five times a day, and/or at regular intervals, for example, every day, every other day, three times a week, weekly, every other week, once a month and/or simply at a frequency or interval as needed or recommended by a medical professional.

In some embodiments, an amount of a binding agent in a composition is an amount needed to obtain an effective therapeutic outcome. In certain embodiments, the amount of a binding agent in a composition (e.g., a pharmaceutical composition) is an amount sufficient to prevent, treat, reduce the severity of, delay the onset of, and/or alleviate a symptom of a neoplastic disorder or cancer, as contemplated herein.

A "therapeutically effective amount" means an amount sufficient to obtain an effective therapeutic outcome and/or an amount necessary sufficient to prevent, treat, reduce the severity of, delay the onset of, and/or alleviate a symptom of a neoplastic disorder or cancer. In certain embodiments, a "therapeutically effective amount" means an amount sufficient to terminate the grow of, and/or slow the growth of a neoplasm or cancer. In certain embodiments, a "therapeutically effective amount" means an amount sufficient to inhibit the replication of, and/or induce the death of one or more neoplastic cells. Determination of a therapeutically effective amount is well within the capability of those skilled in the art, especially in light of the detailed disclosure provided herein.

In some embodiments, an amount of a binding agent in a composition is an amount that is at least a therapeutically effective amount and an amount low enough to minimize unwanted adverse reactions. The exact amount of a binding agent or combinations of active agents required will vary from subject to subject, depending on age, weight, and general condition of a subject, the severity of the condition being treated, and the particular combination of drugs administered. Thus, it is not always possible to specify an exact therapeutically effective amount to treat a neoplastic disorder in a diverse group of subjects. As is well known, the specific dosage for a given patient under specific conditions and for a specific disease will routinely vary, but determination of the optimum amount in each case can readily be accomplished by simple routine procedures. Thus, a therapeutically effective amount of a binding agent used to treat a neoplastic disorder may be determined by one of ordinary skill in the art using routine experimentation.

In certain embodiments, an amount of a binding agent in a composition is administered at a suitable therapeutically effective amount or a dose (e.g., at a suitable volume and concentration, which sometimes depends, in part, on a particular route of administration). Within certain embodiments, a binding agent (e.g., a binding agent in a composition) can be administered at a dose from about 0.01 mg/kg (e.g., per kg body weight of a subject) to 500 mg/kg, 0.1 mg/kg to 500 mg/kg, 0.1 mg/kg to 400 mg/kg, 0.1 mg/kg to 300 mg/kg, 0.1 mg/kg to 200 mg/kg, 0.1 mg/kg to 150 mg/kg, 0.1 mg/kg to 100 mg/kg, 0.1 mg/kg to 75 mg/kg, 0.1 mg/kg to 50 mg/kg, 0.1 mg/kg to 25 mg/kg, 0.1 mg/kg to 10 mg/kg, 0.1 mg/kg to 5 mg/kg or 0.1 mg/kg to 1 mg/kg. In some aspects the amount of a binding agent can be about 10 mg/kg, 9 mg/kg, 8 mg/kg, 7 mg/kg, 6 mg/kg, 5 mg/kg, 4 mg/kg, 3 mg/kg, 2 mg/kg, 1 mg/kg, 0.9 mg/kg, 0.8 mg/kg, 0.7 mg/kg, 0.6 mg/kg, 0.5 mg/kg, 0.4 mg/kg, 0.3 mg/kg, 0.2 mg/kg, or 0.1 mg/kg. In some embodiments a therapeutically effective amount of a binding agent is between about 0.1 mg/kg to 500 mg/kg, or between about 1 mg/kg and about 300 mg/kg. Volumes suitable for intravenous administration are well known.

In some embodiments a binding agent is used to detect cMET, in vitro or in vivo. In some embodiments a binding agent is used to detect cMET on a cell surface and/or to determine the presence or absence of a neoplastic cell (e.g., a malignant cell), where the cell expresses cMET. In some embodiments a binding agent is used to determine if a subject has a neoplastic disorder or cancer. In some embodiments a method of detecting cMET comprises determining the presence or absence of cMET on a cell in a sample, (e.g., a sample obtained directly or indirectly from a subject).

Any suitable method can be used to detect and/or quantitate the presence, absence and/or amount of a binding agent specifically bound to cMET, or a portion thereof, non-limiting examples of such methods can be found in Immunology, Werner Luttmann; Academic Press, 2006 and/or Medical Detection and Quantification of Antibodies to Biopharmaceuticals: Practical and Applied Considerations, Michael G. Tovey; John Wiley & Sons, Jul. 12, 2011. Additional non-limiting examples of methods that can be used to detect and/or quantitate the presence, absence and/or amount of a binding agent specifically bound to cMET, or a portion thereof, include use of a competitive immunoassay, a non-competitive immuno assay, western blots, a radioimmunoassay, an ELISA (enzyme linked immunosorbent assay), a competition or sandwich ELISA, a sandwich immunoassay, an immunoprecipitation assay, an immunoradiometric assay, a fluorescent immunoassay, a protein A immunoassay, a precipitin reaction, a gel diffusion precipitin reaction, an immunodiffusion assay, an agglutination assay, a complement fixation assay, an immunohistochemical assay, a Western blot assay, an immunohistological assay, an immunocytochemical assay, a dot blot assay, a fluorescence polarization assay, a scintillation proximity assay, a homogeneous time resolved fluorescence assay, an IAsys analysis, a BIAcore analysis, the like or a combination thereof.

A pharmaceutical composition comprising an amount or dose of a binding agent can, if desired, be provided in a kit, pack or dispensing device, which can contain one or more doses of a binding agent. The pack can for example comprise metal or plastic foil, such as a blister pack. The pack or dispenser device can be accompanied by instructions for administration. The pack or dispenser can also be accompanied with a notice associated with the container in a form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert.

In some embodiments a kit or pack comprises an amount of a binding agent sufficient to treat a patient for 1 day to 1 year, 1 day to 180 days, 1 day to 120 days, 1 day to 90 days, 1 day to 60 days, 1 day to 30 days, or any day or number of days there between, 1-4 hours, 1-12 hours, or 1-24 hours.

A kit optionally includes a product label or packaging inserts including a description of the components or instructions for use in vitro, in vivo, or ex vivo, of the components therein. Exemplary instructions include instructions for a diagnostic method, treatment protocol or therapeutic regimen. In certain embodiments, a kit comprises packaging material, which refers to a physical structure housing components of the kit. The packaging material can maintain the components sterilely, and can be made of material commonly used for such purposes (e.g., paper, corrugated fiber, glass, plastic, foil, ampules, vials, tubes, etc.). Product labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, optical disk such as CD- or DVD-ROM/RAM, DVD, MP3, magnetic tape, or an electrical storage media such as RAM and ROM or hybrids of these such as magnetic/optical storage media, FLASH media or memory type cards. Product labels or inserts can include identifying information of one or more components therein, dose amounts, clinical pharmacology of the active ingredient(s) including mechanism of action, pharmacokinetics (PK) and pharmacodynamics (PD). Product labels or inserts can include information identifying manufacturer information, lot numbers, manufacturer location, date, information on an indicated condition, disorder, disease or symptom for which a kit component may be used. Product labels or inserts can include instructions for the clinician or for a subject for using one or more of the kit components in a method, treatment protocol or therapeutic regimen. Instructions can include dosage amounts, frequency or duration, and instructions for practicing any of the methods, treatment protocols or therapeutic regimes set forth herein. Kits of the invention therefore can additionally include labels or instructions for practicing any of the methods and uses of the invention described herein. Product labels or inserts can include information on potential adverse side effects and/or warnings.

In certain embodiments, a kit comprises one or more controls having a known amount of cMET. In some embodiments, a kit comprises cells expressing cMET. The cells in the kit can be maintained under appropriate storage conditions until the cells are ready to be used.

In some embodiments, a kit is a diagnostic kits comprising a binding agent. A binding agent comprised in a diagnostic kit can take any suitable form. In some embodiments, a diagnostic comprises a binding agent and a detectable label. In certain embodiments, for example, a diagnostic kit comprises or consists of a stick test, including necessary reagents to perform the method of the invention and to produce, for example, a colorimetric result which can be compared against a color chart or standard curve. A diagnostic kit can also comprise components necessary for detecting a binding agent that specifically binds to cMET, for example a secondary antibody.

Example 1

Antibody Generation

Figure 2:
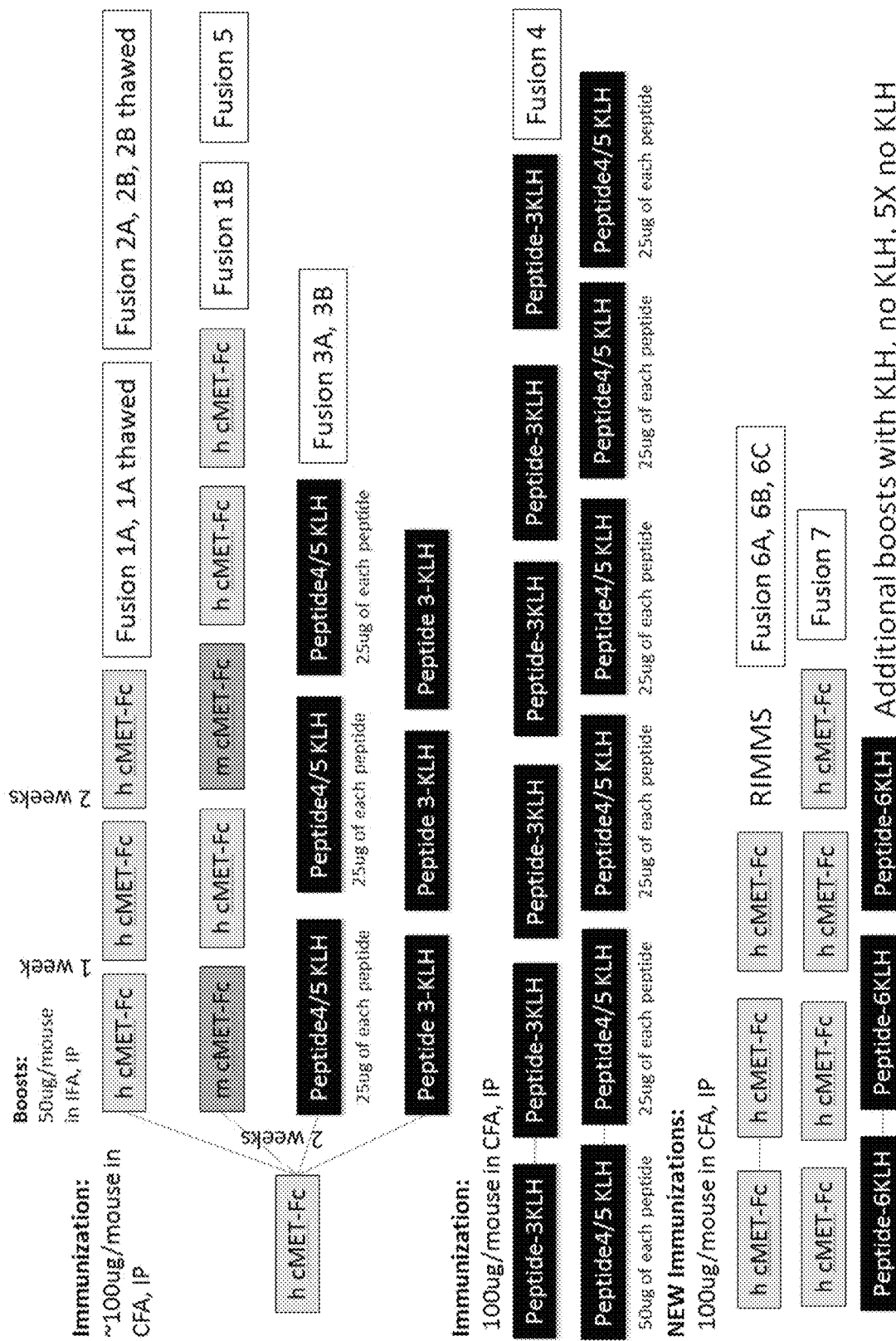
FIG. 2 shows an immunization scheme used to generate monoclonal antibodies (exemplary binding agents) that bind specifically to cMET. Mice were initially immunized by intraperitoneal injection (i.p.) with 100 µg of a human cMET-Fc fusion protein (cMET-Fc), or 50 to 100 µg of a KLH conjugated cMET peptide in Freund's Complete Adjuvant (CFA) as indicated. cMET-Fc comprises the extracellular domain of human cMET fused to an Fc portion of an antibody. cMET peptides were strategically selected from a portion of the cMET extracellular domain. Immunized mice received one or more booster immunization comprising 25 or 50 Mg of cMET-Fc or peptide in Incomplete Freund's adjuvant (IFA) as indicated. Some mice received repetitive immunizations at multiple sites (RIMMS). Immunizations included Met-Fc fusions, peptides, traditional and RIMMS. Spleens of immunized mice were obtained and fused to a suitable fusion partner. Over 20,000 hybridoma clones were obtained and screened.
Figure 3:
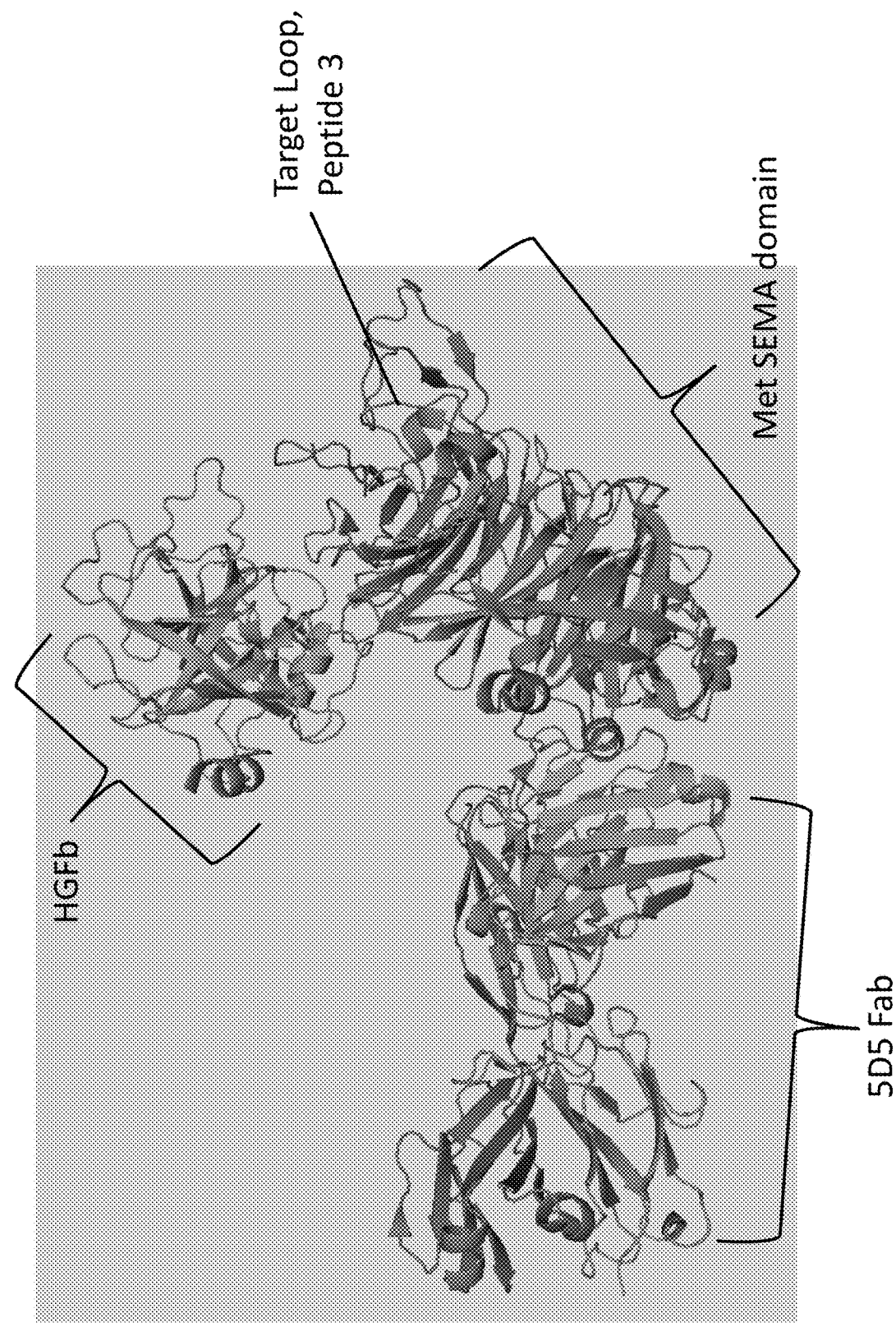
FIG. 3 shows a 3D structure of the MET SEMA domain bound with a Fab of an agonist Met-mAb antibody (5D5 Fab) and HGF beta subunit (HGFβ). The bottom arrow indicates the position of a portion of cMET used to design peptide 3.
Figure 5:
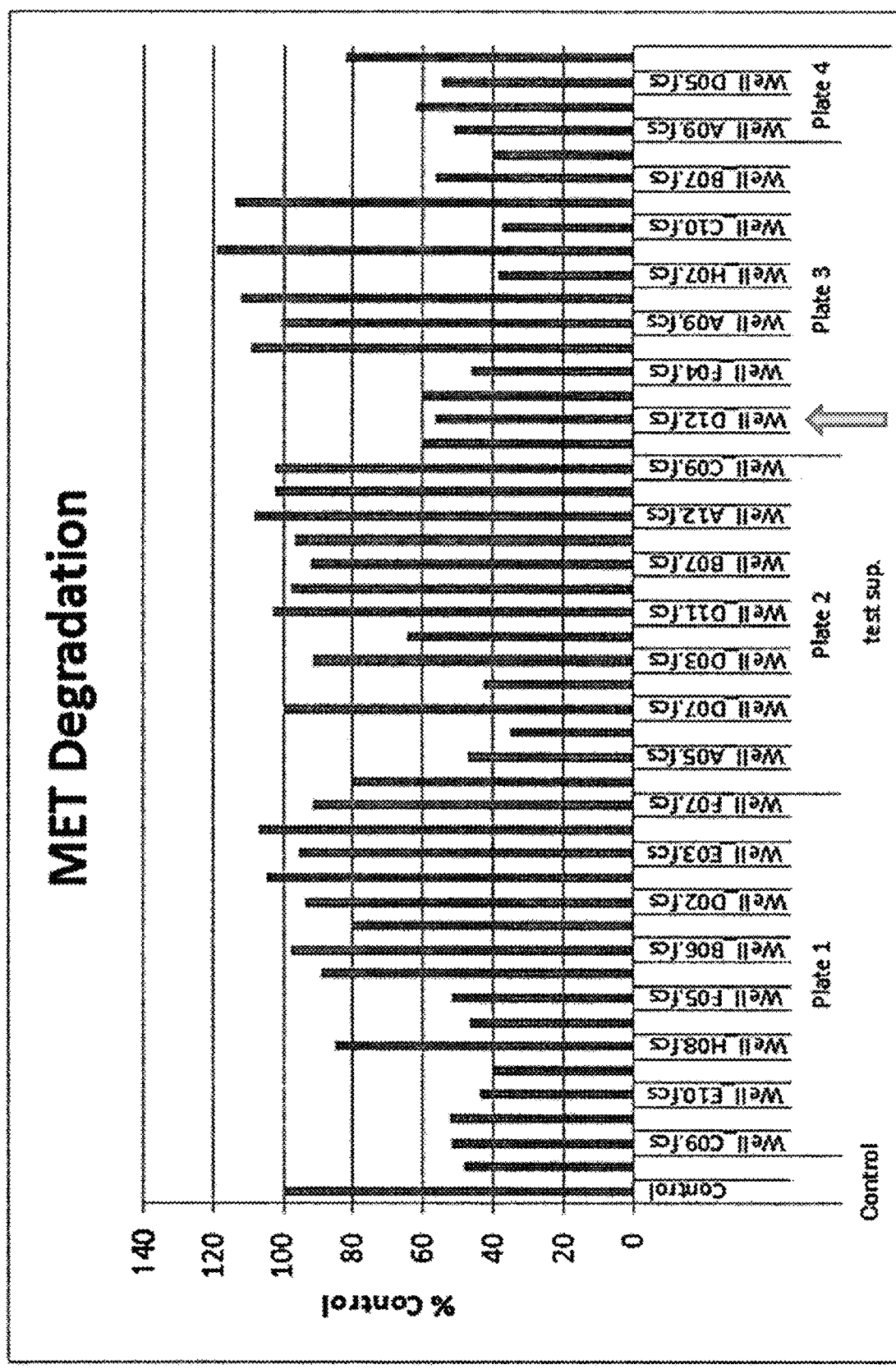
FIG. 5 shows the results of a MET degradation assay. Anti-cMet antibodies isolated from the indicated wells (x-axis) were tested and selected for their ability to induce degradation of cMET on human cancer cell lines as measured by Mesoscale (MSD) cMet protein quantification. Relative values of Met degradation are indicated on the y-axis as % control (percent of control). Values lower than 100% control (negative control level) indicate internalization and degradation of cMet. Degradation indicates not just internalization but lysosomal trafficking, an important property for an antibody drug conjugate. The arrow indicates the results for a lead hybridoma F6B1P3D12.
Figure 6:
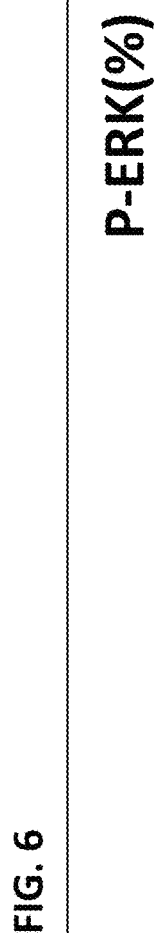
FIG. 6 shows the results of a phospho-ERK assay (P-ERK assay) that measures agonist activity of anti-cMET antibodies by indirectly measuring the phosphorylation of ERK induced by binding of an anti-cMET antibody to cMET on a cell surface. The amount of phosphorylated ERK (shown as % of control, y-axis) detected in cell lysates after treatment of viable cells with an anti-cMET antibody is shown. Anti-cMet antibodies produced from various anti-cMET hybridomas (x-axis) were tested at 6 ug/ml or 30 ug/ml (as indicated on x-axis), and selected according to their inability to induce significant phosphorylation of ERK (i.e., their ability not to induce proliferation, i.e., absence of agonist activity). A lead monoclonal antibody (mAb) P3D12 is indicated by the arrow.
Figure 7A:
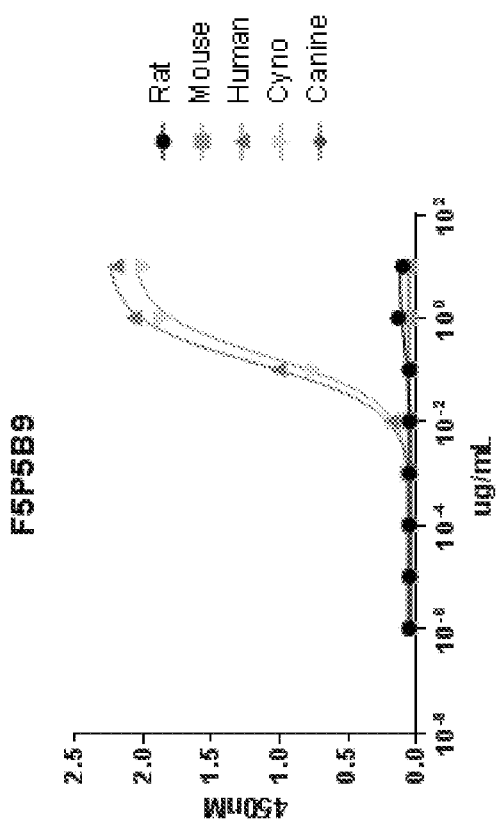
FIGS. 7A-7F show results of certain cMet mAbs that were assayed by ELISA for binding to human, monkey (Cynomolgus Macaque, "Cyno"), canine, rat, and mouse cMet. All monoclonal antibodies bound human and monkey cMet. P3D12 demonstrated significant cross-reactivity with rat cMet. Various concentrations of each antibody are indicated on the x-axis. Relative amounts bound are indicated on the y-axis (OD450 nm).
Figure 7B:
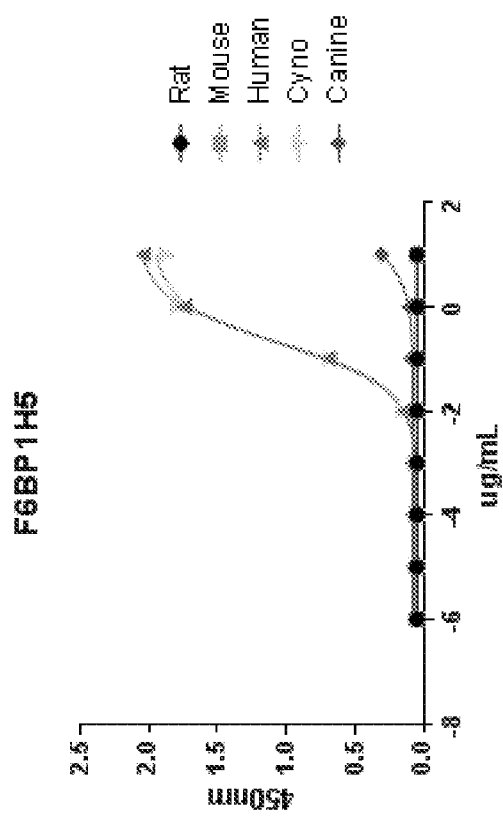
Figure 7C:
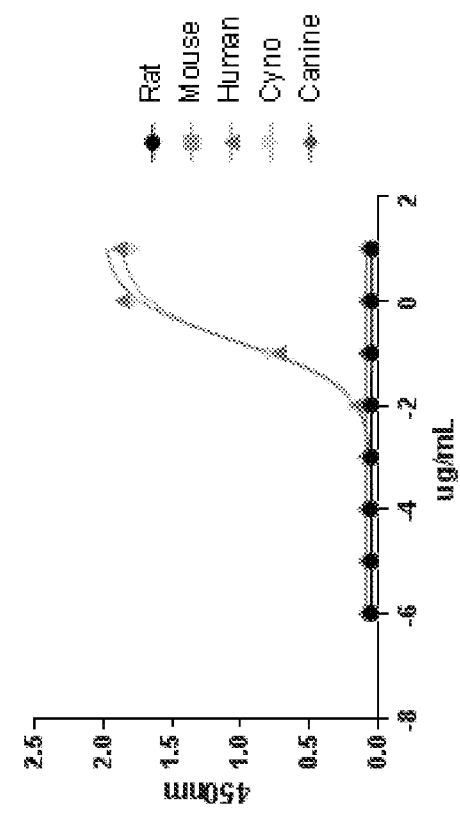
Figure 7D:
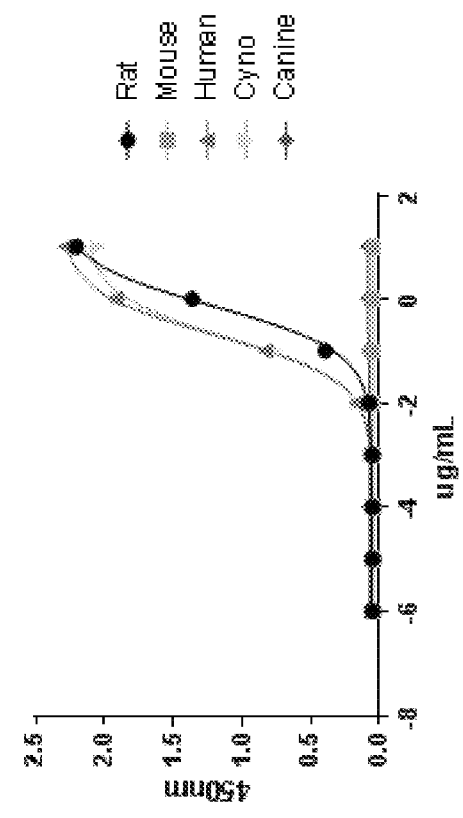
Figure 7E:
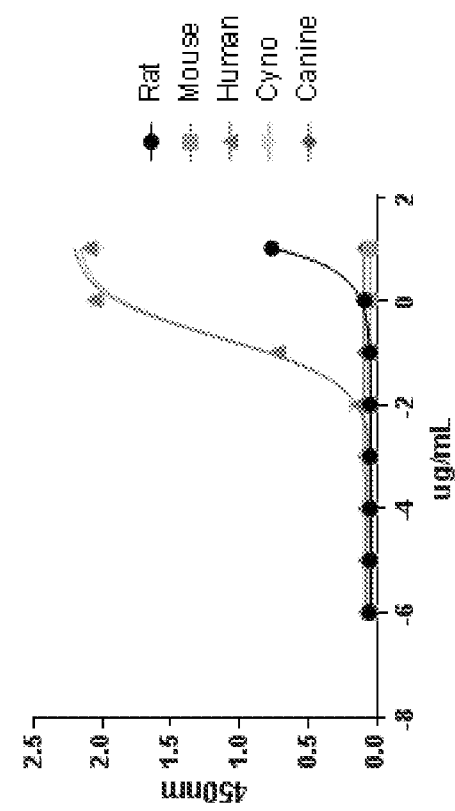
Figure 7F:
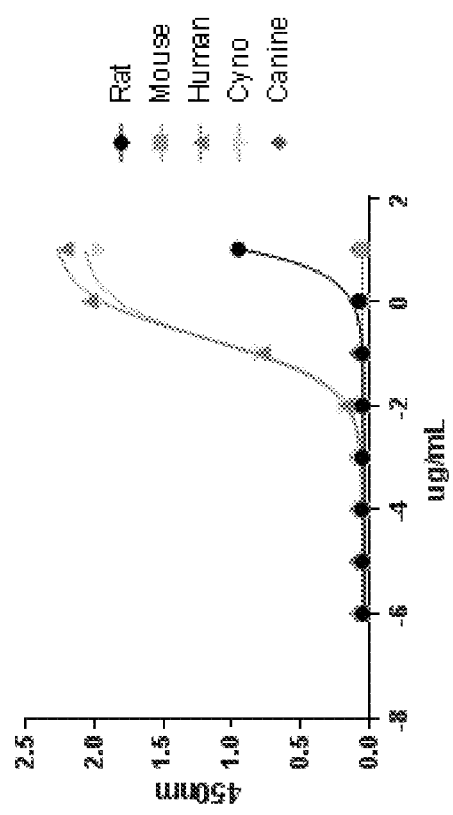

To induce an antibody response against cMET, mice were immunized with cMET-Fc or cMET peptide as described in FIGS. 1 and 2. In some embodiments peptide derived from strategic regions were selected for immunization. FIG. 3 illustrates an example of a structural loop on MET that inspired the design of peptide 3. Spleens from immunized mice were obtained and splenocytes were fused to a suitable fusion partner to produce hybridomas using a standard protocol. Hybridoma clones were isolated and hybridoma media was tested for binding to MET and/or for the ability to induce internalization of cMET on human cancer cell lines as measured by flow cytometry (FIG. 4). Selected hybridoma antibodies were selected for their ability to induce MET degradation (FIG. 5) or inability to induce phosphorylation of ERK (FIG. 6).

Figure 9A:
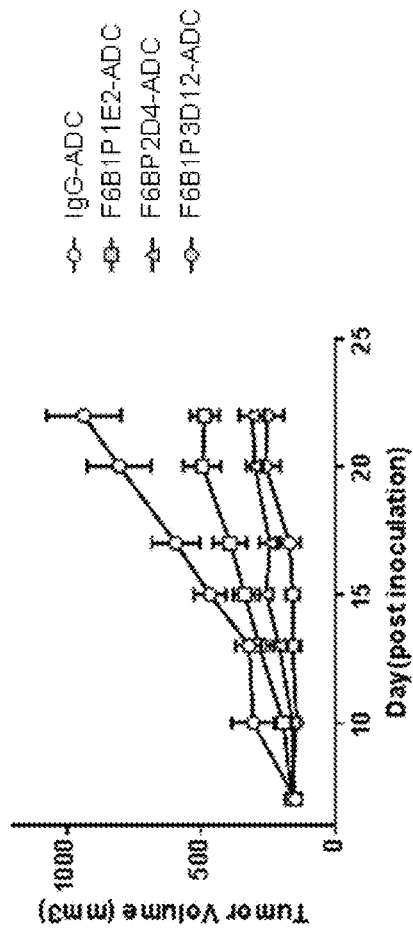
FIGS. 9A and 9B show the results of an in vivo xenograft mouse model evaluating the efficacy of the indicated anti-cMET antibody drug conjugates (ADC) using the MKN45 tumor model (a cMet+gastric cancer model) in nude mice. Animals were treated once with ADCs at 2.5 mg/kg (9A) or 5.0 mg/kg (9B). The efficacy of each drug conjugated anti-cMET binding agent is compared to PBS or an unrelated non-targeting monoclonal antibody (IgG-ADC). Tumor volume (y-axis) was measured at various time points after inoculation (y-axis, Days (post inoculation)). Inhibition of tumor growth indicates positive efficacy. Anti-cMET binding agents and the non-targeting monoclonal antibody (IgG) were conjugated to monomethyl auristatin F (MMAF).
Figure 9B:
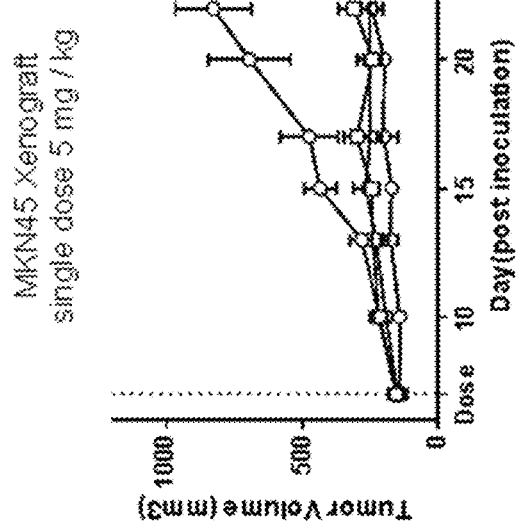
Figure 10:
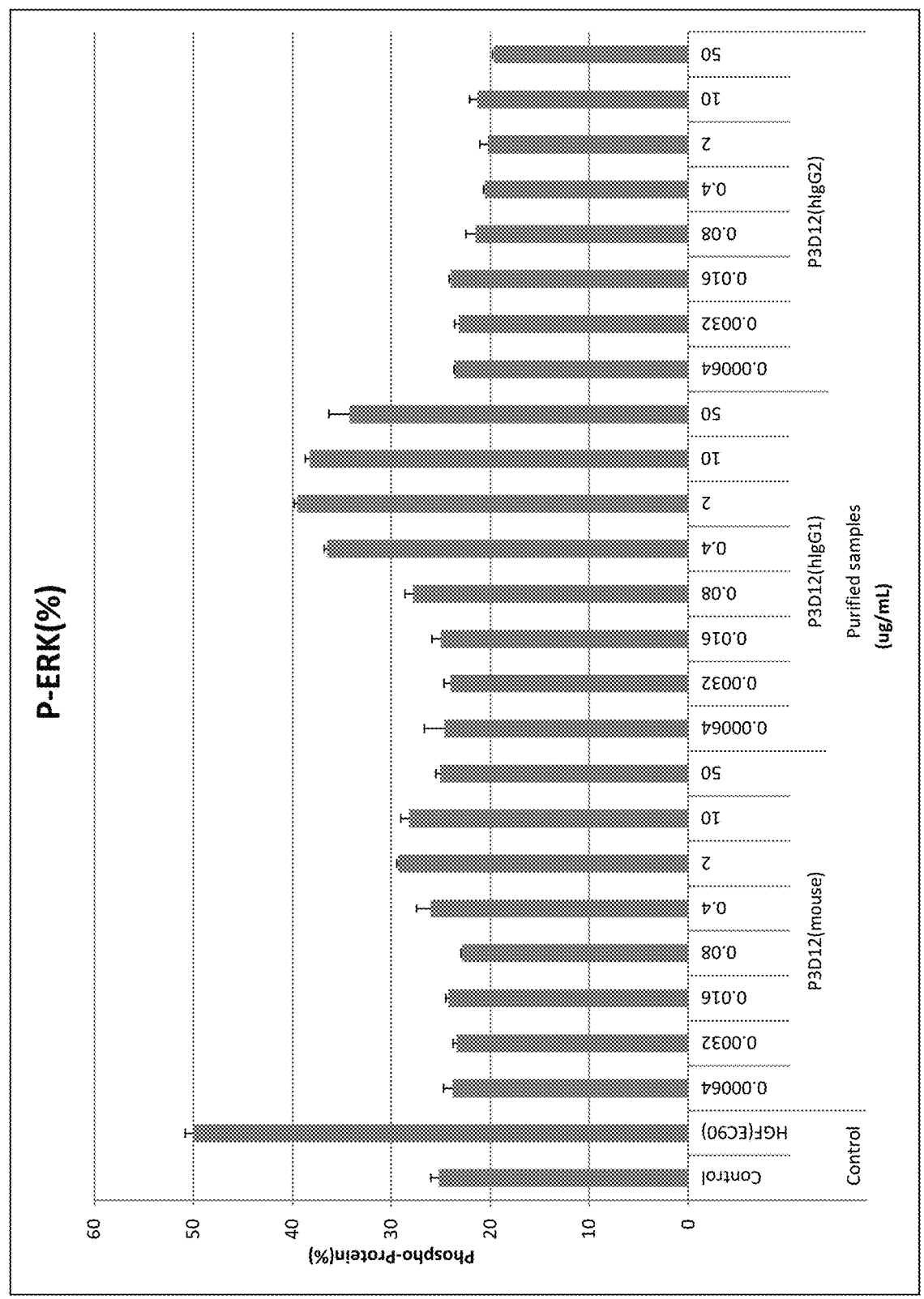
FIG. 10 shows the results of a phospho-ERK assay (P-ERK assay) that measures agonist activity of anti-cMET antibodies by indirectly measuring the phosphorylation of ERK induced by binding of an anti-cMET antibody to cMET on a cell surface. The amount of phosphorylated ERK (shown as % of control, y-axis) detected in cell lysates after treatment of viable cells with an anti-cMET antibody is shown. The constant regions of the heavy and light chains of an isolated mouse monoclonal antibody designated as P3D12 were replaced with antibody constant regions of a human IgG1 (P3D12(hIgG1)), or a human IgG2 (P3D12(hIgG2)) as indicated on the x-axis. Each antibody was tested at 0.00064 ug/ml, 0.0032 ug/ml, 0.016 ug/ml, 0.08 ug/ml, 0.4 ug/ml, 2 ug/ml, 10 ug/ml and 50 ug/ml as indicated on the x-axis. "Control" indicates an untreated negative control. HGF(EC90) is a positive control and indicates cells treated with Hepatocyte Growth Factor (HGF), the natural ligand of cMet receptor. This data indicates that the human IgG2 isotype does not display detectable agonist activity.
Figure 11:
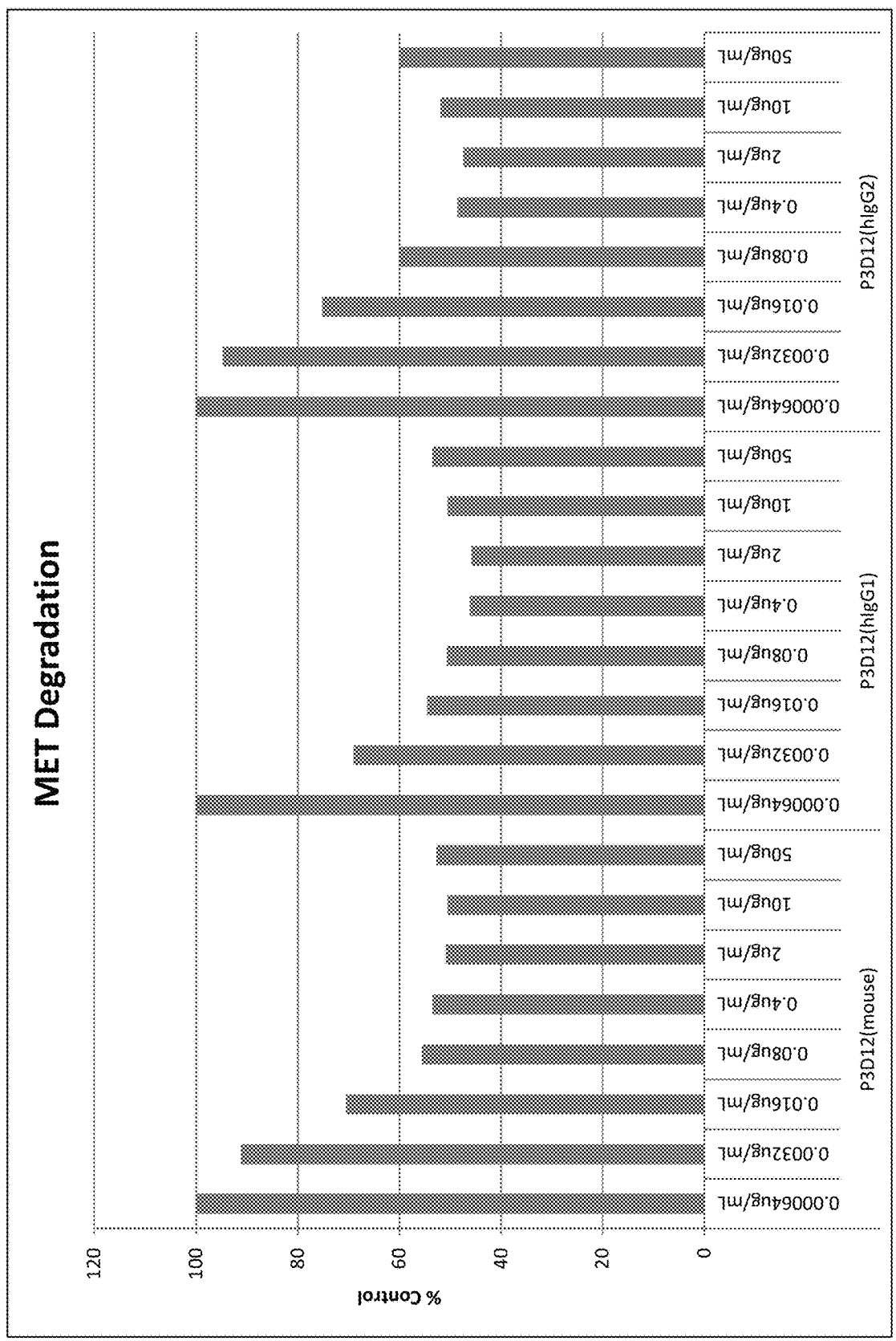
FIG. 11 shows the results of a MET degradation assay. Degradation is a measure of internalization of the cMET receptor upon antibody binding. Chimeric anti-cMet antibodies were tested for their ability to induce degradation of cMET on human cancer cell lines as measured by Mesoscale (MSD) cMet protein quantification. Relative values of Met degradation are indicated on the y-axis as % control (percent of control). Values lower than 100% control indicate internalization and degradation of cMet. Chimeric antibodies were generated by replacing the constant regions of the heavy and light chains of an isolated mouse monoclonal antibody designated as P3D12 (P3D12(mouse)) with antibody constant regions of a human IgG (P3D12(hIgG1)), or a human IgG2 (P3D12(hIgG2)) as indicated on the x-axis. Each antibody was tested at 0.00064 ug/ml, 0.0032 ug/ml, 0.016 ug/ml, 0.08 ug/ml, 0.4 ug/ml, 2 ug/ml, 10 ug/ml and 50 ug/ml as indicated on the x-axis. Chimeric cMet antibodies of P3D12 showed similar internalization/degradation activity as the parental mouse P3D12 antibody.
Figure 12:
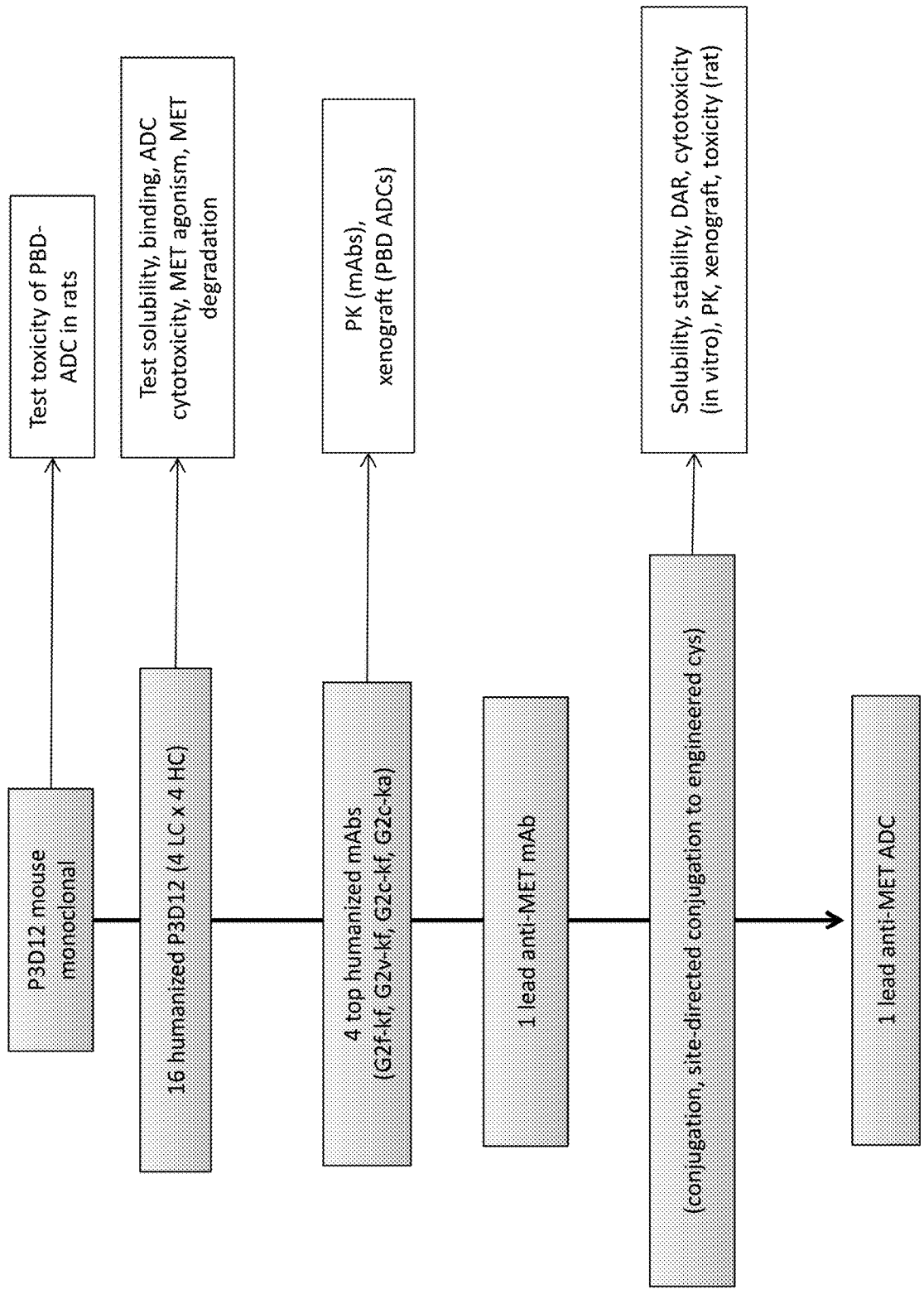
FIG. 12 shows a flow chart of process development for testing and selection of lead anti-cMET monoclonal binding agents.
Figure 15:
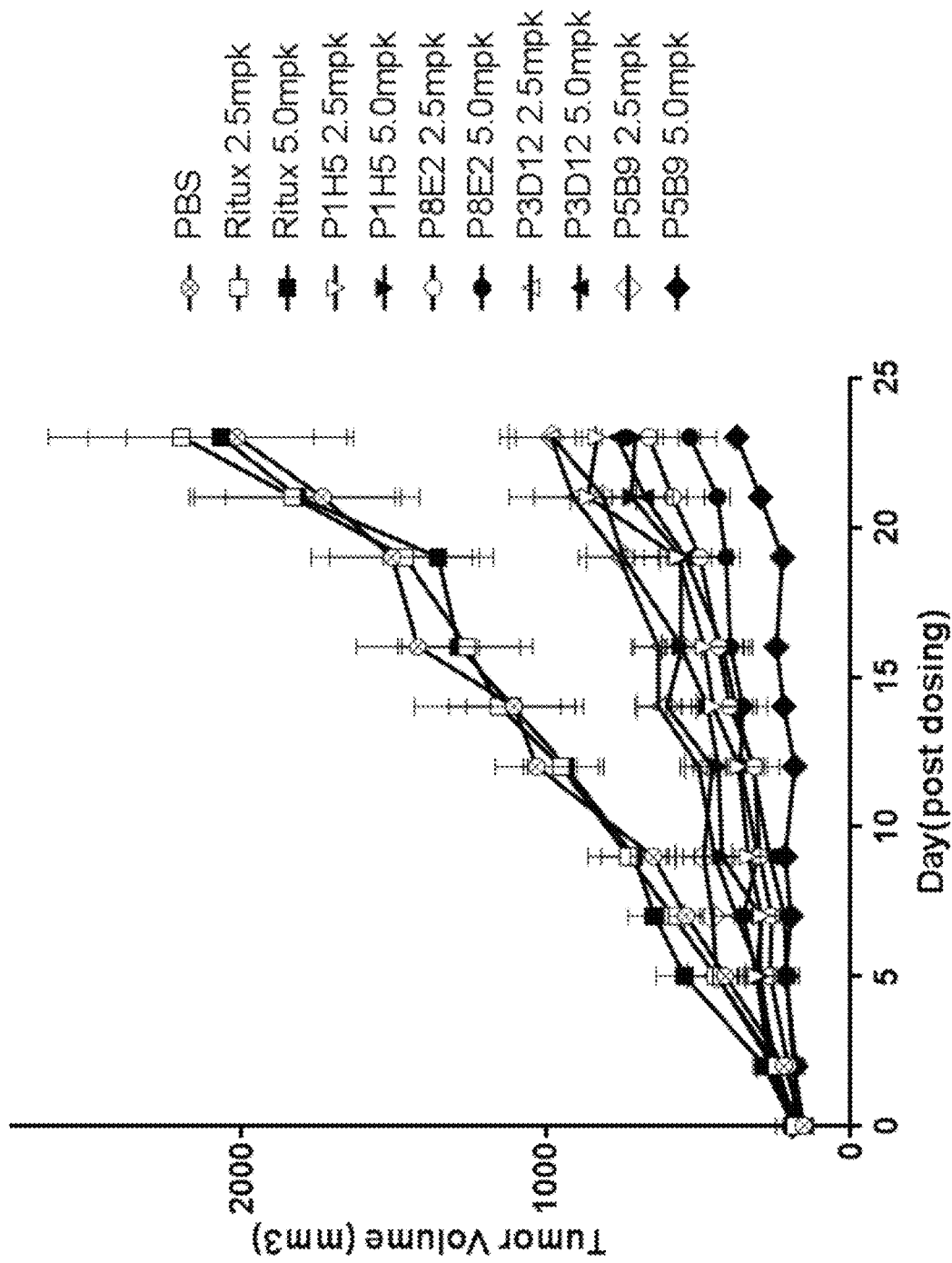
FIG. 15 shows the results of an in vivo xenograft mouse model testing the efficacy of the indicated humanized anti-cMET antibody drug conjugates (ADC) at 2.5 mg/kg (2.5 mpk), or at 5 mg/kg (5 mpk) as demonstrated using an MKN45 tumor model (a cMet+gastric cancer model). Animals were treated once with the indicated ADCs at 2.5 or 5.0 mg/kg. The efficacy of each anti-cMET binding agent is compared to PBS or the non-targeting monoclonal antibody Rituximab (Retux), which is an anti-cancer monoclonal antibody that targets CD20, which is primarily found on the surface of immune system B cells. Tumor volume (y-axis) was measured at various time points (y-axis) after inoculation. Inhibition of tumor growth indicates positive efficacy. Anti-cMET binding agents were conjugated to monomethyl auristatin F (MMAF).
Figure 16:
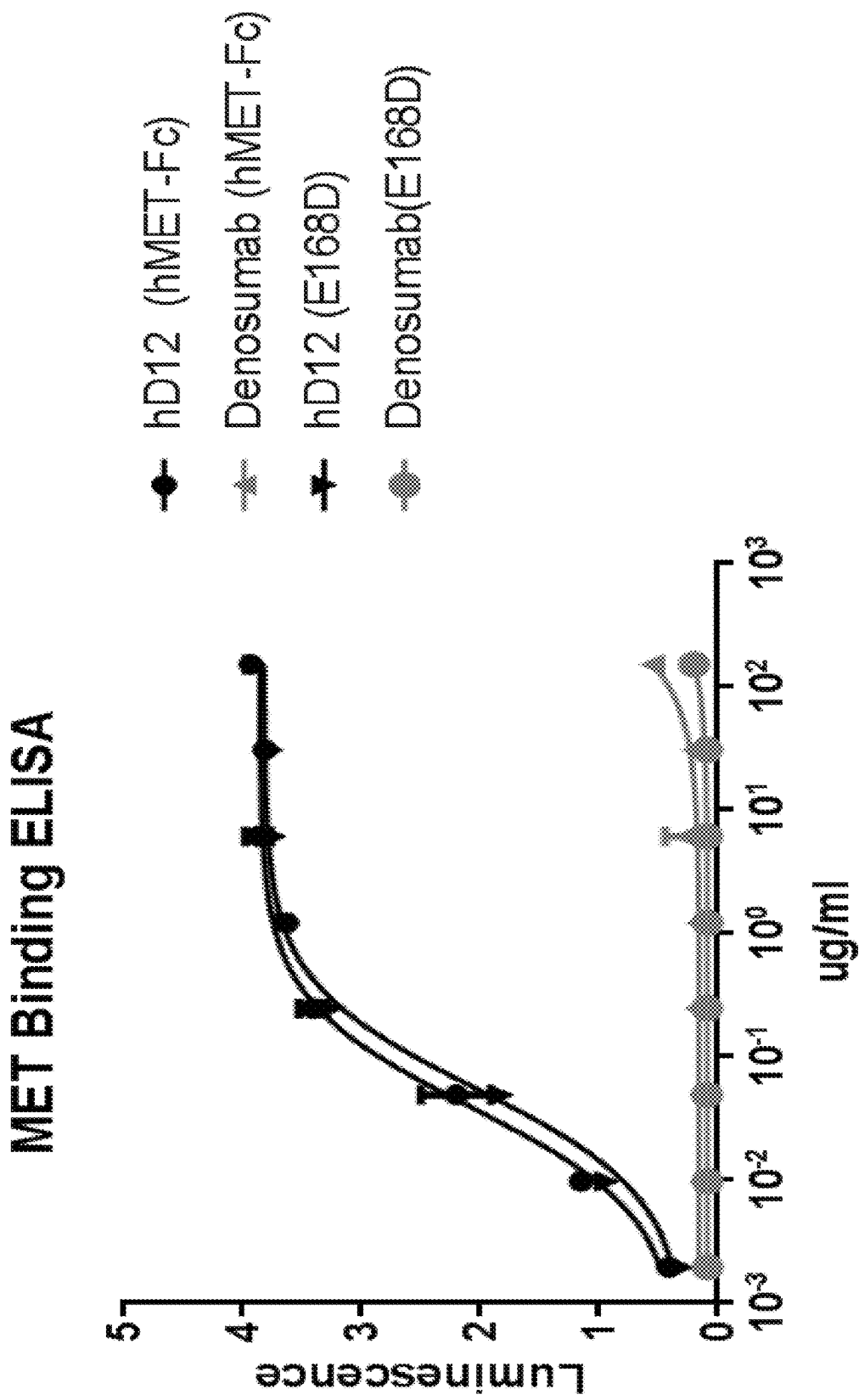
FIG. 16 shows binding of anti-cMET monoclonal binding agents hD12 and MET IgG2 to cMET-Fc and mutant cMET (E168D) Fc recombinant fusion proteins. The E168D mutation is a somatic mutation found in small cell lung cancer (SCLC). The mutation is located in the Sema domain and leads to constitutive activation of the cMet receptor. Abundance of somatic mutations of cMet are very low. E168D occurs in 0.8% to 3% of SCLC patients. A binding ELISA was performed with human cMET or E168D cMET extracellular domains fused to human IgG1 Fc. cMET proteins were coated on a plate overnight and the samples titrated and detected with a goat anti-human IgG (H+L)-HRP. EC50s were determined using sigmoidal dose response fit.

Additional assays were performed to select ideal anti-cMET antibody candidates. For example, anti-cMET antibodies were tested for species cross-reactivity by determining the ability of an antibody to bind to human cMET, monkey cMET (e.g., *Macaca fascicularis*, i.e., Cynomolgus macaque), rat cMET and mouse cMET as measured by ELISA (FIG. 7 & Table 1). In vivo half-life and other pharmacokinetic characteristics were also evaluated (data not shown). Potency and specificity of antibody drug conjugates (ADC) was also determined on high, medium and negative cMET expressing cell lines using anti-cMET antibodies that were conjugated to MMAF)(FIGS. 9 and 15, Tables 11 and 12). ADCs were tested for efficacy in vivo using an MKN45 Xenograft model.

TABLE 11

| In vitro Ranking | Antibody | Avg. Cytotoxicity EC50, pM SNU16 cells (Met medium) | Avg. Cytotoxicity EC50, pM SNU620 cells (Met high) | Met Binding KD (pM) SPR w/hMet-Fc | Met Degradation (pM) MSD | Cell Proliferation (Agonism) ERK Phospho Assay | Cross-reactivity NHP | Rat | Mouse |
|---|---|---|---|---|---|---|---|---|---|
|  | 5D5 |  |  | 800 |  | Yes/Strong | Yes | No | No |
|  | ABF46 | 450 | 67 | 700 | 10,000 | NO | Yes | No | No |
| 1 | F6B1P3D12 | 25 | 60 | 750 | 140 | NO | Yes | Yes | No |
| 2 | F6BP2D4 | 60 | 33 | 480 | 3,000 | NO | Yes | No | No |
| 2 | F6B1P1E2 | 70 | 55 | 890 | 1,920 | Very low | Yes | Low | No |
| 3 | F6AP12F12 | 180 | 97 | 110 | 450 | NO | Not tested | Not tested | Not tested |
| 3 | F5P5B9 | 20 | 3 | 80 | 255 | Very low | Yes | No | No |
| 3 | F6AP8E2 | 351 | 102 | 160 | 7,000 | Very low at high concentrations | Yes | No | No |
| 3 | F6BP1H5/H6 | 80 | 63 | 340 | 3,000 | Maybe at high concentrations | Yes | No | No |

SPR = Surface Plasmon Resonance
MSD = Meso Scale Discovery Platform
NHP = Non-human Primate (i.e., Cynomolgus Macaque)
5D5 = agonist positive control
ABF46 = MET ADC, positive control Example 2

Summary of Characteristics of Selected Humanized Monoclonal Binding Agents.

Humanized and isotype switched monoclonal binding agents were generated which comprise the heavy chain CDRs and light chain CDRs of the mouse monoclonal antibody P3D12. Sixteen different heavy chain (HC) and light chain (LC) combinations were tested for solubility in PBS, binding to human cMET, binding to rat cMET, binding affinity to human and rat cMET as determined by surface plasmon resonance (SPR), the presence of agonistic activity and cMET degradation reported as Meso Scale Discovery platform (MSD). The results are summarized in Table 12 below.

TABLE 12

| Rank | HC | LC | Clone | Solubility in PBS | ELISA hMET vs parental | ELISA rMET vs parental | vc-MMAF ADC IC50, pM, SNU-16 (n = 1) | SPR kD, nM, hMET-Fc | SPR kD, nM, rMET-Fc | pERK (MET agonism MSD) | MET degradation equal to parental? (MSD) |
|---|---|---|---|---|---|---|---|---|---|---|---|
| | VH-abb/sdr | VH-abb/sdr | G2aka | | 0.9 | 1.1 | 352 | 0.9 | 26 | negative | yes |
| | | VH-fra | G2akf | | 1.0 | 0.5 | 368 | 0.6 | 23 | negative | yes |
| | | VH-ven | G2akv | Insoluble | 1.8 | 1.3 | | | | negative | yes |
| | | VH-cdr | G2akc | | 1.3 | 0.7 | 352 | 0.7 | 38 | negative | yes |
| | VH-fra | VH-abb/sdr | G2fka | | 1.8 | 3.8 | | | | negative | yes |
| 3 | | VH-fra | G2fkf | | 1.7 | 1.4 | 266 | 0.4 | 30 | negative | yes |
| | | VH-ven | G2fkv | Insoluble | 1.7 | 1.2 | | | | negative | yes |
| | | VH-cdr | G2fkc | | 1.7 | 2.3 | | | | negative | yes |
| | VH-ven | VH-abb/sdr | G2vka | | 0.9 | 2.7 | | | | negative | yes |
| 2 | | VH-fra | G2vkf | | 1.1 | 1.0 | 380 | 0.3 | 8 | negative | yes |
| | | VH-ven | G2vkv | Insoluble | 1.8 | 1.6 | | | | negative | yes |
| | | VH-cdr | G2vkc | | 1.1 | 1.9 | | | | negative | yes |
| 4 | VH-cdr | VH-abb/sdr | G2cka | | 1.3 | 2.7 | 238 | 0.4 | 29 | negative | yes |
| 1 | | VH-fra | G2ckf | | 0.7 | 0.9 | 302 | 0.3 | 7 | negative | yes |
| | | VH-ven | G2ckv | Insoluble | 1.1 | 1.0 | | | | negative | yes |
| | | VH-cdr | G2ckc | | 1.0 | 2.0 | 159 | 0.9 | 31 | negative | yes |
| | Chimeric P3D12 | | | | | | 249 | 0.7 | 30 | | |
| | Mouse P3D12 | | | | | | 42 | 0.9 | 16 | | |

Example 3

A human subject presents with multiple metastatic carcinomas of 2 cm or larger, present in liver and lung. A biopsy is performed to determine if the cells of the carcinoma express cMET on their cell surface. The presence of cell surface cMET expression is confirmed from the biopsy results.

The human subject is administered a binding agent that specifically binds to the extracellular domain of human cMET. The binding agent optionally comprises human kappa and IgG heavy-chain constant regions, the light chain variable region of SEQ ID NO: 41 and the heavy chain variable regions of SEQ ID NO:98. The binding agent can be administered at a dose of 30 mg/kg, intravenously, in a volume of 300 ml over a period of 2 hours, once a day for six weeks. The presence, size and viability of the tumor is determined by follow-up biopsy and ultrasound. The subject is determined to be in remission after six weeks of treatment.

Example 4

A human subject presents with multiple metastatic carcinomas of 2 cm or larger, present in liver and lung. A biopsy is performed to determine if the cells of the carcinoma express cMET on their cell surface. The presence of cell surface cMET expression is confirmed from the biopsy results.

The human subject is administered a binding agent that specifically binds to the extracellular domain of human cMET. The binding agent optionally comprises human kappa and IgG2a heavy-chain constant regions, the humanized light chain variable region of SEQ ID NO: 48 and the humanized heavy chain variable region of SEQ ID NO: 107. The binding agent is optionally conjugated to MMAF. The binding agent is administered at a dose of 1 mg/kg, intravenously, in a volume of 300 ml over a period of 2 hours, once a day for six weeks. The presence, size and viability of the tumor is determined by follow-up biopsy and ultrasound. The subject is determined to be in remission after six weeks of treatment.

Example 5 cMET Sequences

SEQ ID NO: 109 (Human cMET-UniProtKB-P08581 (MET_HUMAN))
*Residue E168 and N375 are bolded and underlined.
MKAPAVLAPGILVLLFTLVQRSNGECKEALAKSEMNVNMKYQLPNFTAETP
IQNVILHEHHIFLGATNYIYVLNEEDLQKVAEYKTGPVLEHPDCFPCQDCSSK
ANLSGGVWKDNINMALVVDTYYDDQLISCGSVNRGTCQRHVFPHNHTADI
QSEVHCIFSPQIEEPSQCPDCVVSALGAKVLSSVKDRFINFFVGNTINSSYFPD
HPLHSISVRRLKETKDGFMFLTDQSYIDVLPEFRDSYPIKYVHAFESNNFIYFL
TVQRETLDAQTFHTRIIRFCSINSGLHSYMEMPLECILTEKRKKRSTKKEVFNI
LQAAYVSKPGAQLARQIGASLNDDILFGVFAQSKPDSAEPMDRSAMCAFPIK
YVNDFFNKIVNKNNVRCLQHFYGPNHEHCFNRTLLRNSSGCEARRDEYRTE
FTTALQRVDLFMGQFSEVLLTSISTFIKGDLTIANLGTSEGRFMQVVVSRSGP
STPHVNFLLDSHPVSPEVIVEHTLNQNGYTLVITGKKITKIPLNGLGCRHFQSC
SQCLSAPPFVQCGWCHDKCVRSEECLSGTWTQQICLPAIYKVFPNSAPLEGG
TRLTICGWDFGFRRNNKFDLKKTRVLLGNESCTLTLSESTMNTLKCTVGPA cMET Sequences

MNKHFNMSIIISNGHGTTQYSTFSYVDPVITSISPKYGPMAGGTLLTLTGNYL
NSGNSRHISIGGKTCTLKSVSNSILECYTPAQTISTEFAVKLKIDLANRETSIFS
YREDPIVYEIHPTKSFISGGSTITGVGKNLNSVSVPRMVINVHEAGRNFTVAC
QHRSNSEIICCTTPSLQQLNLQLPLKTKAFFMLDGILSKYFDLIYVHNPVFKPF
EKPVMISMGNENVLEIKGNDIDPEAVKGEVLKVGNKSCENIHLHSEAVLCTV
PNDLLKLNSELNIEWKQAISSTVLGKVIVQPDQNFTGLIAGVVSISTALLLLLG
FFLWLKKRKQIKDLGSELVRYDARVHTPHLDRLVSARSVSPTTEMVSNESV
DYRATFPEDQFPNSSQNGSCRQVQYPLTDMSPILTSGDSDISSPLLQNTVHID
LSALNPELVQAVQHVVIGPSSLIVHFNEVIGRGHFGCVYHGTLLDNDGKKIH
CAVKSLNRITDIGEVSQFLTEGIIMKDFSHPNVLSLLGICLRSEGSPLVVLPYM
KHGDLRNFIRNETHNPTVKDLIGFGLQVAKGMKYLASKKFVHRDLAARNC
MLDEKFTVKVADFGLARDMYDKEYYSVHNKTGAKLPVKWMALESLQTQK
FTTKSDVWSFGVLLWELMTRGAPPYPDVNTFDITVYLLQGRRLLQPEYCPDP
LYEVMLKCWHPKAEMRPSFSELVSRISAIFSTFIGEHYVHVNATYVNVKCVA
PYPSLLSSEDNADDEVDTRPASFWETS

SEQ ID NO: 110 (Rat cMET-UniProtKB-P97523 (MET_RAT))
MKAPTALAPGILLLLLTLAQRSHGECKEALVKSEMNVNMKYQLPNFTAETPI
HNVVLPGHHIYLGATNYIYVLNDKDLQKVSEFKTGPVVEHPDCFPCQDCSS
KANVSGGVWKDNVMALLVDTYYDDQLISCGSVNRGTCQRHVLPPDNAA
DIQSEVHCMFSPLAEEESGQCPDCVVSALGAKVLLSEKDRFINFFVGNTINSS
YPPDYSLHSISVRRLKETQDGFKFLTDQSYIDVLPEFRDSYPIKYIHAFESNHFI
YFLTVQKETLDAQTFHTRIIRFCSVDSGLHSYMEMPLECILTEKRRKRSTREE
VFNILQAAYVSKPGANLAKQIGASPYDDILYGVFAQSKPDSAEPMNRSAVCA
FPIKYVNDFFNKIVNKNNVRCLQHFYGPNHEHCFNRTLLRNSSGCEVRSDEY
RTEFTTALQRVDLFMGRLNHVLLTSISTFIKGDLTIANLGTSEGRFMQVVLSR
TAHFTPHVNFLLDSYPSPEVIVEHPSNQNGYTLVVTGKKITKIPLNGLGCGH
FQSCSQCLSPPYFIQCGWCHNRCVHSNECPSGTWTQEICLPAVYKVFPTSAPL
EGGTMLTICGWDFGFKKNNKFDLRKTKVLLGNESCTLTLSESTTNTLKCTV
GPAMSEHFNVSVIVSNSRETTQYSAFSYVDPVITSISPRYGPHAGGTLLTLTG
KYLNSGNSRHISIGGKTCTLKSVSDSILECYTPGHTVSAEFPVKLKIDLADRV
TSSFSYREDPVVSEIFIPTKSFISGGSTITGIGKNLNSVSTPKLVIEVHDVGVNYT
VACQHRSSSEIICCTTPSLRQLDLQLPLKTKAFFLLDGILSKHFDLTYVHDPMF
KPFEKPVMISMGNENVVEIKGDDIDPEAVKGEVLKVGNKSCENLHWHSEAL
LCTVPSDLLKLNGGELNIEWKQAVSSTVLGKVIVQPDQNFAGLIIGAVSISVV
VLLVSGLFLWLRKRKHKDLGSELVRYDARVHTPHLDRLVSARSVSPTTEMV
SNESVDYRATFPEDQFPNSSQNGACRQVQYLLTDLSPILTSGDSDISSPLLQN
TVHIDLSALNPELVQAVPHVVIGPSSLIVHFNEVIGRGHFGCVYHGTLLDSDG
KKIHCAVKSLNRITDIEEVSQFLTEGIIMKDFSHPNVLSLLGICLRSEGSPLVVL
PYMKHGDLRNFIRNETHNPTVKDLIGFGLQVAKGMKYLVSKKFVHRDLAA
RNCMLDEKFTVKVADFGLARDMYDKEYYSVHNKTGAKLPVKWMALESLQ
TQKFTTKSDVWSFGVLLWELMTRGAPPYPDVNTFDITIYLLQGRRLLQPEYC
PDALYEVMLKCWHPKAEMRPSVSELVSRISSIFSTFIGEHYVHVNATYVNVK
CVAPYPSLLPSQDNIDGEANT SEQ ID NO: 111 (Mouse cMET-UniProtKB-P16056 (MET_MOUSE))
MKAPTVLAPGILVLLLSLVQRSHGECKEALVKSEMNVNMKYQLPNFTAETPI
QNVVLHGHHIYLGATNYIYVLNDKDLQKVSEFKTGPVLEHPDCLPCRDCSS
KANSSGGVWKDNINMALLVDTYYDDQLISCGSVNRGTCQRHVLPPDNSADI
QSEVHCMFSPEEESGQCPDCVVSALGAKVLLSEKDRFINFFVGNTINSSYPPG
YSLHSISVRRLKETQDGFKFLTDQSYIDVLPEFLDSYPIKYIHAFESNHFIYFLT
VQKETLDAQTFHTRIIRFCSVDSGLHSYMEMPLECILTEKRRKRSTREEVFNI
LQAAYVSKPGANLAKQIGASPSDDILFGVFAQSKPDSAEPVNRSAVCAFPIK
YVNDFFNKIVNKNNVRCLQHFYGPNHEHCFNRTLLRNSSGCEARSDEYRTE
FTTALQRVDLFMGRLNQVLLTSISTFIKGDLTIANLGTSEGRFMQVVLSRTAH
LTPHVNFLLDSHPSPEVIVEHPSNQNGYTLVVTGKKITKIPLNGLGCGHFQS
CSQCLSAPYFIQCGWCHNQCVRFDECPSGTWTQEICLPAVYKVFPTSAPLEG
GTVLTICGWDFGFRKNNKFDLRKTKVLLGNESCTLTLSESTTNTLKCTVGPA
MSEHFNVSVIISNSRETTQYSAFSYVDPVITSISPRYGPQAGGTLLTLTGKYLN
SGNSRHISIGGKTCTLKSVSDSILECYTPAQTTSDEFPVKLKIDLANRETSSFSY
REDPVVYEIHPTKSFISGGSTITGIGKTLNSVSLPKLVIDVHEVGVNYTVACQ
HRSNSEIICCTTPSLKQLGLQLPLKTKAFFLLDGILSKHFDLTYVHNPVFEPFE
KPVMISMGNENVVEIKGNNIDPEAVKGEVLKVGNQSCESLHWHSGAVLCTV
PSDLLKLNSELNIEWKQAVSSTVLGKVIVQPDQNFAGLIIGAVSISVVVLLLS
GLFLWMRKRKHKDLGSELVRYDARVHTPHLDRLVSARSVSPTTEMVSNES
VDYRATFPEDQFPNSSQNGACRQVQYPLTDLSPILTSGDSDISSPLLQNTVHI
DLSALNPELVQAVQHVVIGPSSLIVHFNEVIGRGHFGCVYHGTLLDNDGKKI
HCAVKSLNRITDIEEVSQFLTEGIIMKDFSHPNVLSLLGICLRSEGSPLVVLPY
MKHGDLRNFIRNETHNPTVKDLIGFGLQVAKGMKYLASKKFVHRDLAARN
CMLDEKFTVKVADFGLARDMYDKEYYSVHNKTGAKLPVKWMALESLQTQ
KFTTKSDVWSFGVLLWELMTRGAPPYPDVNTFDITIYLLQGRRLLQPEYCPD
ALYEVMLKCWHPKAEMRPSFSELVSRISSIFSTFIGEHYVHVNATYVNVKCV
APYPSLLPSQDNIDGEGNT SEQ ID NO: 112 (Dog cMET)
MKAPAVLAPGILVLLFTLVQKSYGECKEALVKSEMNVNMKYQLPNFTAETP
IQNVVLHKHHIYLGAVNYIYVLNDKDLQKVAEYKTGPVLEHPDCSPCQDCS cMET Sequences

```
HKANLSGGVWEDNINMALLVDTYYDDQLISCGSVHRGTCQRHILPPSNIADI
QSEVHCMYSSQADEEPSQCPDCVVSALGTKVLISEKDRFINFFVGNTINSSDH
PDHSLHSISVRRLKETQDGFKFLTDQSYIDVLPEFRDSYPIKYVHAFESNHFIY
FLTVQRETLDAQTFHTRIIRFCSVDSGLHSYMEMPLECILTEKRRKRSTREEV
FNILQAAYVSKPGAHLAKQIGANLNDDILYGVFAQSKPDSAEPMNRSAVCA
FPIKYVNEFFNKIVNKNNVRCLQHFYGPNHEHCFNRTLLRNSSGCEARNDEY
RTEFTTALQRVDLFMGQFNQVLLTSISTFIKGDLTIANLGTSEGRFMQVVVSR
SGLSTPHVNFRLDSHPVSPEAIVEHPLNQNGYTLVVTGKKITRIPLNGLGCEH
FQSCSQCLSAPPFVQCGWCHDRCVHLEECPTGAWTQEVCLPAIYEVFPTSAP
LEGGTVLTVCGWDFGFRRNNKFDLKKTKVFLGNESCTLTLSESTTNMLKCT
VGPAVNEHFNISIIISNGRGTAQYSTFSYVDPIITSISPSYGPKNGGTLLTLTGK
YLNSGNSRHISMGGKTCTLKSVSDSILECYTPAQATATEFPIKLKIDLANREM
NSFSYQEDPIVYAIHPTKSFISGGSTITAVGKNLNSVSVLRMVIDVHETRRNFT
VACQHRSNSEIICCTTPSLQQLNLQLPLKTKAFFMLDGIHSKYFDLIYVHNPV
FKPFEKPVMISIGNENVLEIKGNDIDPEAVKGEVLKVGNKSCETIYSDSKAVL
CKVPNDLLKLNNELNIEWKQAVSSTVLGKVIVQPDQNFTGLIAGVISISTIVL
LLLGLFLWLKRKKQIKDLGSELVRYDARVHTPHLDRLVSARSVSPTTEMVS
NESVDYRATFPEDQFPNSSQNGSCRQVQYPLTDLSPMLTSGDSDISSPLLQNT
VHIDLSALNPELVQAVQHVVIGPSSLIVHFNEVIGRGHFGCVYHGTLLDNDD
KKIHCAVKSLNRITDIGEVSQFLTEGIIMKDFSHPNVLSLLGICLRSEGSPLVV
LPYMKHGDLRNFIRNETHNPTVKDLIGFGLQVAKGMKYLASKKFVHRDLA
ARNCMLDEKFTVKVADFGLARDMYDKEYYSVHNKTGAKLPVKWMALESL
QTQKFTTKSDVWSFGVLLWELMTRGAPPYPDVNTFDITVYLLQGRRLLQPE
YCPDPLYEVMLKCWHPRAELRPSFSELVSRISAIFSTFIGEHYVHVNATYVNV
KCVAPYPSLLSSQDNIDGEGDT

SEQ ID NO: 113 (Macaca mulatta, Rhesus cMET-NCBI Reference
Sequence: NP_001162100.1)
MKAPAVLVPGILVLLFTLVQRSNGECKEALAKSEMNVNMKYQLPNFTAETA
IQNVILHEHHIFLGATNYIYVLNEEDLQKVAEYKTGPVLEHPDCFPCQDCSSK
ANLSGGVWKDNINMALVVDTYYDDQLISCGSVNRGTCQRHVFPHNHTADI
QSEVHCIFSPQIEEPNQCPDCVVSALGAKVLSSVKDRFINFFVGNTINSSYFPH
HPLHSISVRRLKETKDGFMPLTDQSYIDVLPEFRDSYPIKYIHAFESNNFIYFL
TVQRETLNAQTFHTRIIRFCSLNSGLHSYMEMPLECILTEKRKKRSTKKEVFN
ILQAAYVSKPGAQLARQIGASLNDDILFGVFAQSKPDSAEPMDRSAMCAFPI
KYVNDFFNKIVNKNNVRCLQHFYGPNHEHCFNRTLLRNSSGCEARRDEYRA
EFTTALQRVDLFMGQFSEVLLTSISTFVKGDLTIANLGTSEGRFMQVVVSRSG
PSTPHVNFLLDSHPVSPEVIVEHPLNQNGYTLVVTGKKITKIPLNGLGCRHFQ
SCSQCLSAPPFVQCGWCHDKCVRSEECPSGTWTQQICLPAIYKVFPTSAPLEG
GTRLTICGWDFGFRRNNKFDLKKTRVLLGNESCTLTLSESTMNTLKCTVGPA
MNKHFNMSIIISNGHGTTQYSTFSYVDPIITSISPKYGPMAGGTLLTLTGNYLN
SGNSRHISIGGKTCTLKSVSNSILECYTPAQTISTEFAVKLKIDLANRETSIFSY
REDPIVYEIHPTKSFISGGSTITGVGKNLHSVSVPRMVINVHEAGRNFTVACQ
HRSNSEIICCTTPSLQQLNLQLPLKTKAFFMLDGILSKYFDLIYVHNPVFKPFE
KPVMISMGNENVLEIKGNDIDPEAVKGEVLKVGNKSCENIHLHSEAVLCTVP
NDLLKLNSELNIEWKQAISSTVLGKVIVQPDQNFTGLIAGVVSISIALLLLGL
FLWLKKRKQIKDLGSELVRYDARVHTPHLDRLVSARSVSPTTEMVSNESVD
YRATFPEDQFPNSSQNGSCRQVQYPLTDMSPILTSGDSDISSPLLQNTVHIDLS
ALNPELVQAVQHVVIGPSSLIVHFNEVIGRGHFGCVYHGTLLDNDGKKIHCA
VKSLNRITDIGEVSQFLTEGIIMKDFSHPNVLSLLGICLRSEGSPLVVLPYMKH
GDLRNFIRNETHNPTVKDLIGFGLQVAKGMKYLASKKFVHRDLAARNCML
DEKFTVKVADFGLARDMYDKEYYSVHNKTGAKLPVKWMALESLQTQKFT
TKSDVWSFGVLLWELMTRGAPPYPDVNTFDITVYLLQGRRLLQPEYCPDPL
YEVMLKCWHPKAEMRPSFSELVSRISAIFSTFIGEHYVHVNATYVNVKCVAP
YPSLLSSEDNADDEVDT
``` cMET Sequences

Example 6

Embodiments

A1. A binding agent that specifically binds to cMET, or a portion thereof, wherein the binding agent comprises a CDR-L1, CDR-L2 and a CDR-L3, each independently selected from a light chain variable domain selected from Table 4 or Table 5.

A2. A binding agent that specifically binds to cMET, or a portion thereof, wherein the binding agent comprises a CDR-H1, CDR-H2 and a CDR-H3, each independently selected from a heavy chain variable domain selected from Table 9 or Table 10.

A3. A binding agent that specifically binds to cMET, or a portion thereof, wherein the binding agent comprises (i) a CDR-L1, CDR-L2 and a CDR-L3, each independently selected from a light chain variable domain selected from Table 4 or Table 5 and (ii) a CDR-H1, CDR-H2 and a CDR-H3, each independently selected from a heavy chain variable domain selected from Table 9 or Table 10.

A4. A binding agent that specifically binds to CMET, or a portion thereof, wherein the binding agent comprises three CDRs of a light chain variable domain selected from the CDRs of Tables 1, 2 and 3, and three CDRs of a heavy chain variable domain selected from the CDRs of Tables 4, 5 and 6.

A5. A binding agent that specifically binds to CMET, or a portion thereof, wherein the binding agent comprises a CDR-L1 selected from Table 1, a CDR-L2 selected from Table 2, a CDR-L3 selected from Table 3, a CDR-H1 selected from Table 4, a CDR-H2 selected from Table 5 and a CDR-H3 selected from Table 6.

A6. A binding agent that specifically binds to CMET, or a portion thereof, wherein the binding agent comprises a CDR-L1 that is at least 80% identical to a CDR selected from Table 1, a CDR-L2 that is at least 80% identical to a CDR selected from Table 2, a CDR-L3 that is at least 80% identical to a CDR selected from Table 3, a CDR-H1 that is at least 80% identical to a CDR selected from Table 4, a CDR-H2 that is at least 80% identical to a CDR selected from Table 5 and a CDR-H3 that is at least 80% identical to a CDR selected from Table 6.

A7. The binding agent of any one of embodiments A1 to A6, wherein the binding agent is a recombinant monoclonal antibody.

A8. A pharmaceutical composition comprising: a binding agent of any one of embodiments A1 to A7; and a pharmaceutical acceptable excipient, diluent, additive or carrier.

A9. The pharmaceutical composition of embodiment A8, wherein the binding agent comprises a constant region of an $IgG_1$, $IgG_2$, $IgG_3$, or $IgG_4$.

A10. The pharmaceutical composition of embodiment A8 or A9, wherein the binding agent comprises a constant region of an IgD, IgE, IgA or IgM.

A11. The pharmaceutical composition of any one of embodiments A8 to A10, wherein the binding agent is humanized.

B1. A recombinant monoclonal antibody comprising: a CDR-L1 that is at least 80% identical to a CDR selected from Table 1, a CDR-L2 that is at least 80% identical to a CDR selected from Table 2, a CDR-L3 that is at least 80% identical to a CDR selected from Table 3, a CDR-H1 that is at least 80% identical to a CDR selected from Table 4, a CDR-H2 that is at least 80% identical to a CDR selected from Table 5 and a CDR-H3 that is at least 80% identical to a CDR selected from Table 6, wherein the antibody specifically binds to an extracellular domain of human cMET.

B2. The antibody of embodiment B1, wherein the antibody is humanized, chimeric or CDR grafted.

C1. An antibody binding agent, pharmaceutical composition or antibody of any one of embodiments A1 to A11, B1, and B2, for use in treating a neoplastic disorder or cancer in a subject.

D1. A binding agent comprising:
a CDR-L1, a CDR-L2 and a CDR-L3 which are three polypeptide sequences of a light chain complementarity determining region (CDR-L), wherein the CDR-L1 is selected from SEQ ID Nos 1-15, the CDR-L2 is selected from SEQ ID Nos 16-25 and the CDR-L3 is selected from SEQ ID Nos 26-36, and wherein the binding agent specifically binds to an extracellular domain of mesenchymal epithelial transition factor (cMET).

D2. A binding agent comprising:
a CDR-H1, a CDR-H2 and a CDR-H3 which are three polypeptide sequences of a heavy chain complementarity determining region (CDR-H), wherein the CDR-H1 is selected from SEQ ID Nos 50-61, the CDR-H2 is selected from SEQ ID Nos 62-78 and the CDR-H3 is selected from SEQ ID Nos 79-93, and wherein the binding agent specifically binds to an extracellular domain of mesenchymal epithelial transition factor (cMET).

D3. A binding agent comprising:
a CDR-L1 selected from SEQ ID NOs. 1-15, a CDR-L2 selected from SEQ ID NOs. 16-25, a CDR-L3 selected from SEQ ID NOs. 26-36, a CDR-H1 selected from SEQ ID Nos 50-61, a CDR-H2 selected from SEQ ID Nos 62-78, and a CDR-H3 selected from SEQ ID Nos 79-93, wherein the binding agent specifically binds to an extracellular domain of mesenchymal epithelial transition factor (cMET).

D4. The binding agent of embodiment 1 or 3, wherein the CDR-L1 is selected from SEQ ID NOs 2, 4, 6, 8, 10, 12 and 14.

D5. The binding agent of embodiment 1, 3 or 4, wherein the CDR-L2 is selected from SEQ ID NOs 17, 19, 21, 23 and 25.

D6. The binding agent of embodiment 1, 3, 4 or 5, wherein the CDR-L3 is selected from SEQ ID NOs 27, 29, 31, 33 and 35.

D7. The binding agent of embodiment 2 or 3, wherein the CDR-H1is selected from SEQ ID NOs 51, 53, 55, 57 and 59.

D8. The binding agent of embodiment 2, 3 or 7, wherein the CDR-H2 selected from SEQ ID Nos 62-78 is selected from SEQ ID NOs 63, 65, 67, 69, 73 and 75.

D9. The binding agent of embodiment 2, 3 or 8, wherein the CDR-H3 is selected from SEQ ID NOs 80, 82, 84, 86, 88, 91 and 93.

D10. The binding agent of any one of embodiments 1 to 9, wherein the binding agent is an antibody, or a binding fragment thereof.

D11. The binding agent of embodiment 10, wherein the binding agent is a monoclonal antibody, or binding fragment thereof.

D12. The binding agent of any one of embodiments 1 to 11, wherein the binding agent comprises a constant region of an IgG1, IgG2, IgG3, or IgG4.

D13. The binding agent of any one of embodiments 1 to 11, wherein the binding agent comprises a constant region of an IgD, IgE, IgA or IgM.

D14. The binding agent of any one of embodiments 1 to 13, wherein the binding agent is humanized.

D15. The binding agent of any one of embodiments 1 to 13, wherein the binding agent comprises at least one humanized or human framework region.

D16. The binding agent of embodiment 15, wherein the binding agent comprises at least three humanized or human framework regions.

D17. The binding agent of any one of embodiments 1 to 13, wherein the binding agent comprises at least one mouse framework region.

D18. The binding agent of embodiment 17, wherein the binding agent comprises at least three mouse framework regions.

D19. The binding agent of any one of embodiments 1 to 18, wherein the binding agent is a Fab, Fab', F(ab')2, Fv or scFV fragment of an antibody.

D20. The binding agent of any one of embodiments 1 to 19, wherein the binding agent consists of a single chain polypeptide.

D21. The binding agent of any one of embodiments 1 to 13, wherein the binding agent comprises a variable light chain region having an amino acid sequence selected from SEQ ID NOS 37-44.

D22. The binding agent of any one of embodiments 1 to 13, wherein the binding agent comprises a variable heavy chain region having an amino acid sequence selected from SEQ ID NOS 94-103.

D23. The binding agent of any one of embodiments 1 to 13, wherein the binding agent comprises a light chain sequence selected from SEQ ID NOS 45-49.

D24. The binding agent of any one of embodiments 1 to 13, wherein the binding agent comprises a heavy chain sequence selected from SEQ ID NOS 104-108.

D25. The binding agent of embodiment 23 or 24, wherein the light chain sequence selected from SEQ ID NOS 45-49 and/or the heavy chain sequence selected from SEQ ID NOS 104-108 comprises one to five amino acid modifications selected from an amino acid addition, an amino acid deletion and an amino acid substitution.

D26. The binding agent of any one of embodiments 1 to 25, wherein the binding agent induces internalization of cMET on a human cancer cell.

D27. The binding agent of any one of embodiments 1 to 25, wherein the binding agent induces degradation of cMET on a human cancer cell.

D28. The binding agent of any one of embodiments 1 to 25, wherein the binding agent is not a cMET agonist.

D29. The binding agent of any one of embodiments 1 to 28, wherein the binding agent binds specifically to a mammalian cMET.

D30. The binding agent of embodiment 29, wherein the mammalian cMET is a human cMET, monkey cMET or rat cMET.

D31. The binding agent of embodiment 30, wherein the binding agent binds specifically to a human cMET, monkey cMET and rat cMET.

D32. The binding agent of embodiment 30, wherein the binding agent binds specifically to human cMET.

D33. The binding agent of any one of embodiments 1 to 32, wherein the binding agent specifically binds to the extracellular domain of a wild type cMET.

D34. The binding agent of any one of embodiments 1 to 32, wherein the binding agent specifically binds to the extracellular domain of a cMET variant.

D35. The binding agent of embodiment 34, wherein the cMET variant comprises an E168D or an N375S variant of cMET.

D36. The binding agent of any one of embodiments 1 to 34, wherein the binding agent specifically binds the extracellular domain of human cMET with a KD of 10 nM or less.

D37. The binding agent of embodiment 36, wherein the binding agent specifically binds the extracellular domain of human cMET with a KD of 1 nM or less.

D38. The binding agent of any one of embodiments 1 to 37, wherein the binding agent comprises an anti-neoplastic agent.

D39. A composition comprising a first binding agent that is the binding agent of any one of embodiments 1 to 38, and a second binding agent that does not bind specifically to cMET.

D40. The composition of embodiment 39, wherein a first binding agent is the binding agent that specifically binds to the extracellular domain of cMET and the second binding agent is conjugated to the first binding agent.

D41. A method of treating a subject having a neoplastic disorder or cancer comprising:
a) providing a subject having, or suspected of having, a neoplastic disorder; and
b) administering a therapeutically effective amount of the binding agent of any one of embodiments 1 to 38 or the composition of any one of embodiments 39 to 40 to the subject.

D42. The method of embodiment 41, wherein the binding agent specifically binds to the extracellular domain of cMET expressed on one or more cells of the subject.

D43. The method of embodiment 41 or 42, wherein the binding agent inhibits mitosis of, and/or induces death of the one or more cells expressing cMET.

D44. The method of any one of embodiments 41 to 43, wherein the neoplastic disorder or cancer comprises a lung carcinoma, breast carcinoma, ovarian carcinoma, kidney carcinoma, colorectal carcinoma, gastric carcinoma, thyroid carcinoma, pancreas carcinoma, neuroblastoma, or a squamous cell carcinoma of the head and neck, cervical cancer, hepatocellular cancer, sarcomas, mesothelioma, glioblastoma, multiple myeloma, melanoma, prostate and esophageal carcinoma.

D45. A pharmaceutical composition comprising the binding agent of any one of embodiments 1 to 38, and a pharmaceutically acceptable excipient, diluent, additive or carrier.

D46. The pharmaceutical composition of embodiment 45, wherein the additive comprises a preservative.

D47. The pharmaceutical composition of embodiment 45 or 46, wherein the diluent comprises phosphate buffered saline.

D48. The pharmaceutical composition of any one of embodiments 45 to 47, wherein the excipient comprises sodium citrate dehydrate or polyoxyethylene-sorbitan-20 mono-oleate (polysorbate 80).

D49. The pharmaceutical composition any one of embodiments 45 to 48, wherein the carrier comprises a recombinant protein.

D50. The pharmaceutical composition of any one of embodiments 45 to 49, wherein the composition is sterile.

D51. The pharmaceutical composition of any one of embodiments 45 to 50, wherein the composition is formulated as a sterile, lyophilized powder suitable for intravenous administration to a mammal.

The entirety of each patent, patent application, publication or any other reference or document cited herein hereby is incorporated by reference. In case of conflict, the specification, including definitions, will control.

Citation of any patent, patent application, publication or any other document is not an admission that any of the foregoing is pertinent prior art, nor does it constitute any admission as to the contents or date of these publications or documents.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All of the features disclosed herein may be combined in any combination. Each feature disclosed in the specification may be replaced by an alternative feature serving a same, equivalent, or similar purpose. Thus, unless expressly stated otherwise, disclosed features (e.g., antibodies) are an example of a genus of equivalent or similar features.

As used herein, all numerical values or numerical ranges include integers within such ranges and fractions of the values or the integers within ranges unless the context clearly indicates otherwise. Further, when a listing of values is described herein (e.g., about 50%, 60%, 70%, 80%, 85% or 86%) the listing includes all intermediate and fractional values thereof (e.g., 54%, 85.4%). Thus, to illustrate, reference to 80% or more identity, includes 81%, 82%, 83%, 84%, 85%, 86%, 87%, 88%, 89%, 90%, 91%, 92%, 93%, 94% etc., as well as 81.1%, 81.2%, 81.3%, 81.4%, 81.5%, etc., 82.1%, 82.2%, 82.3%, 82.4%, 82.5%, etc., and so forth.

Reference to an integer with more (greater) or less than includes any number greater or less than the reference number, respectively. Thus, for example, a reference to less than 100, includes 99, 98, 97, etc. all the way down to the number one (1); and less than 10, includes 9, 8, 7, etc. all the way down to the number one (1).

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth.

Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, 1,000-1,500, 1,500-2,000, 2,000-2,500, 2,500-3,000, 3,000-3,500, 3,500-4,000, 4,000-4,500, 4,500-5,000, 5,500-6,000, 6,000-7,000, 7,000-8,000, or 8,000-9,000, includes ranges of 10-50, 50-100, 100-1,000, 1,000-3,000, 2,000-4,000, etc.

Modifications can be made to the foregoing without departing from the basic aspects of the technology. Although the technology has been described in substantial detail with reference to one or more specific embodiments, those of ordinary skill in the art will recognize that changes can be made to the embodiments specifically disclosed in this application, yet these modifications and improvements are within the scope and spirit of the technology.

The invention is generally disclosed herein using affirmative language to describe the numerous embodiments and aspects. The invention also specifically includes embodiments in which particular subject matter is excluded, in full or in part, such as substances or materials, method steps and conditions, protocols, or procedures. For example, in certain embodiments or aspects of the invention, materials and/or method steps are excluded. Thus, even though the invention is generally not expressed herein in terms of what the invention does not include aspects that are not expressly excluded in the invention are nevertheless disclosed herein.

The technology illustratively described herein suitably can be practiced in the absence of any element(s) not specifically disclosed herein. Thus, for example, in each instance herein any of the terms "comprising," "consisting essentially of," and "consisting of" can be replaced with either of the other two terms. The terms and expressions which have been employed are used as terms of description and not of limitation, and use of such terms and expressions do not exclude any equivalents of the features shown and described or segments thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. The term, "substantially" as used herein refers to a value modifier meaning "at least 95%", "at least 96%", "at least 97%", "at least 98%", or "at least 99%" and may include 100%. For example, a composition that is substantially free of X, may include less than 5%, less than 4%, less than 3%, less than 2%, or less than 1% of X, and/or X may be absent or undetectable in the composition.

Thus, it should be understood that although the present technology has been specifically disclosed by representative embodiments and optional features, modification and variation of the concepts herein disclosed can be resorted to by those skilled in the art, and such modifications and variations are considered within the scope of this technology.

The invention claimed is:

1. A binding agent comprising:
a CDR-L1 selected from SEQ ID NOs: 1-15,
a CDR-L2 selected from SEQ ID NOs: 16-25,
a CDR-L3 selected from SEQ ID NOs: 26-36,
a CDR-H1 selected from SEQ ID NOs: 50-61,
a CDR-H2 selected from SEQ ID NOs: 62-78, and
a CDR-H3 selected from SEQ ID NOs: 79-93
wherein the binding agent specifically binds to an extracellular domain of mesenchymal epithelial transition factor (cMET).

2. The binding agent of claim 1, wherein the binding agent is an antibody, or a binding fragment thereof.

3. The binding agent of claim 2, which is selected from the group consisting of:
(i) a binding agent comprising
a CDR-L1 of SEQ ID NO: 1 or 2,
a CDR-L2 of SEQ ID NO: 16 or 17,
a CDR-L3 of SEQ ID NO: 26 or 27,
a CDR-H1 of SEQ ID NO: 50 or 51,
a CDR-H2 of SEQ ID NO: 62 or 53, and
a CDR-H3 of SEQ ID NO: 79 or 80;
(ii) a binding agent comprising
a CDR-L1 of SEQ ID NO: 3 or 4,
a CDR-L2 of SEQ ID NO: 18 or 19,
a CDR-L3 of SEQ ID NO: 28 or 29,
a CDR-H1 of SEQ ID NO: 52 or 53,
a CDR-H2 of SEQ ID NO: 64 or 65, and
a CDR-H3 of SEQ ID NO: 81 or 82;
(iii) a binding agent comprising
a CDR-L1 of SEQ ID NO: 5 or 6,
a CDR-L2 of SEQ ID NO: 20 or 21,
a CDR-L3 of SEQ ID NO: 30 or 31,
a CDR-H1 of SEQ ID NO: 54 or 55,
a CDR-H2 of SEQ ID NO: 66 or 67, and
a CDR-H3 of SEQ ID NO: 83 or 84;
(iv) a binding agent comprising
a CDR-L1 of SEQ ID NO: 7 or 8,
a CDR-L2 of SEQ ID NO: 22 or 23,
a CDR-L3 of SEQ ID NO: 34 or 35,
a CDR-H1 of SEQ ID NO: 56 or 57,
a CDR-H2 of SEQ ID NO: 68 or 69, and
a CDR-H3 of SEQ ID NO: 85 or 86;

(v) a binding agent comprising
   a CDR-L1 of SEQ ID NO: 9 or 10,
   a CDR-L2 of SEQ ID NO: 24 or 25,
   a CDR-L3 of SEQ ID NO: 34 or 35
   a CDR-H1 of SEQ ID NO: 58 or 59
   a CDR-H2 of SEQ ID NO: 70 or 71, and
   a CDR-H3 of SEQ ID NO: 87 or 88;
(vi) a binding agent comprising
   a CDR-L1 of SEQ ID NO: 11 or 12,
   a CDR-L2 of SEQ ID NO: 24 or 25,
   a CDR-L3 of SEQ ID NO: 34 or 35,
   a CDR-H1 of SEQ ID NO: 58 or 59,
   a CDR-H2 of SEQ ID NO: 74 or 75, and
   a CDR-H3 of SEQ ID NO: 90 or 91; and
(vii) a binding agent comprising
   a CDR-L1 of SEQ ID NO: 11 or 12,
   a CDR-L2 of SEQ ID NO: 24 or 25,
   a CDR-L3 of SEQ ID NO: 34 or 35,
   a CDR-H1 of SEQ ID NO: 58 or 59
   a CDR-H2 of SEQ ID NO: 72 or 73, and
   a CDR-H3 of SEQ ID NO: 88 or 89.

4. The binding agent of claim 3, wherein
the CDR-L1 is SEQ ID NO: 9 or 10,
the CDR-L2 is SEQ ID NO: 24 or 25,
the CDR-L3 is SEQ ID NO: 34 or 35,
the CDR-H1 is SEQ ID NO: 58 or 59,
the CDR-H2 is SEQ ID NO: 70 or 71, and
the CDR-H3 is SEQ ID NO: 87 or 88.

5. The binding agent of claim 2, wherein the binding agent comprises a light chain having a sequence selected from SEQ ID NOs: 46-49.

6. The binding agent of claim 2, wherein the binding agent comprises a heavy chain having a sequence selected from SEQ ID NOs: 105-108.

7. The binding agent of claim 2, wherein the binding agent has a light chain having a sequence selected from SEQ ID NOs: 46-49 which comprises zero to five amino acid modifications selected from an amino acid addition, an amino acid deletion and an amino acid substitution the and a heavy chain having a sequence selected from SEQ ID NOs: 105-108 which comprises ene zero to five amino acid modifications selected from an amino acid addition, an amino acid deletion and an amino acid substitution.

8. The binding agent of claim 7, wherein the binding agent has a light chain having a sequence comprising SEQ ID NO: 47 and a heavy chain having a sequence comprising SEQ ID NO: 108.

9. The binding agent of claim 7, wherein the binding agent has a light chain having a sequence comprising SEQ ID NO: 47 and a heavy chain having a sequence comprising SEQ ID NO: 106.

10. The binding agent of claim 7, wherein the binding agent has a light chain having a sequence comprising SEQ ID NO: 47 and a heavy chain having a sequence comprising SEQ ID NO: 105.

11. The binding agent of claim 1, wherein the binding agent induces internalization of cMET on a human cancer cell.

12. The binding agent of claim 1, wherein the binding agent induces degradation of cMET on a human cancer cell.

13. The binding agent of claim 1, wherein the binding agent comprises an anti-neoplastic agent.

14. A composition comprising a first binding agent that is the binding agent of claim 3, and a second binding agent that does not bind specifically to cMET.

15. The composition of claim 14, wherein the first binding agent is the binding agent that specifically binds to the extracellular domain of cMET and the second binding agent is conjugated to the first binding agent.

16. A pharmaceutical composition comprising the binding agent of claim 1, and a pharmaceutically acceptable excipient, diluent, additive or carrier.

17. A method of treating a subject having or suspected of having a neoplastic disorder or cancer comprising:
   a) providing a subject having, or suspected of having, a neoplastic disorder or cancer; and
   b) administering a therapeutically effective amount of the binding agent of claim 1 to the subject.

18. The method of claim 17, wherein the binding agent specifically binds to the extracellular domain of cMET expressed on one or more cells of the subject.

19. The method of claim 18, wherein the binding agent inhibits mitosis of, and/or induces death of the one or more cells expressing cMET.

20. The method of claim 17, wherein the neoplastic disorder or cancer is selected from the group consisting of lung carcinoma, breast carcinoma, ovarian carcinoma, kidney carcinoma, colorectal carcinoma, gastric carcinoma, thyroid carcinoma, pancreas carcinoma, neuroblastoma, or a squamous cell carcinoma of the head and neck, cervical cancer, hepatocellular cancer, sarcomas, mesothelioma, glioblastoma, multiple myeloma, melanoma, prostate and esophageal carcinoma.

* * * * *

UNITED STATES PATENT AND TRADEMARK OFFICE
CERTIFICATE OF CORRECTION

PATENT NO. : 11,299,547 B2
APPLICATION NO. : 16/334326
DATED : April 12, 2022
INVENTOR(S) : Julia Coronella et al.

Page 1 of 1

It is certified that error appears in the above-identified patent and that said Letters Patent is hereby corrected as shown below:

In the Claims

In Column 137, Line 66:
Replace "a CDR-H2 of SEQ ID NO: 62 or 53"
With --a CDR-H2 of SEQ ID NO: 62 or 63--

Signed and Sealed this
Third Day of June, 2025

Coke Morgan Stewart
*Acting Director of the United States Patent and Trademark Office*